(12) United States Patent
Madlambayan et al.

(10) Patent No.: US 7,795,024 B2
(45) Date of Patent: Sep. 14, 2010

(54) APPARATUS AND METHODS FOR AMPLIFICATION OF BLOOD STEM CELL NUMBERS

(75) Inventors: Gerard Madlambayan, Toronto (CA); Peter Zandstra, Toronto (CA)

(73) Assignee: Insception Bioscience, Inc., Mississauga, Ontario (CA)

(*) Notice: Subject to any disclaimer, the term of this patent is extended or adjusted under 35 U.S.C. 154(b) by 607 days.

(21) Appl. No.: 10/555,604

(22) PCT Filed: May 3, 2004

(86) PCT No.: PCT/IB2004/001724

§ 371 (c)(1),
(2), (4) Date: Dec. 8, 2006

(87) PCT Pub. No.: WO2004/096975

PCT Pub. Date: Nov. 11, 2004

(65) Prior Publication Data
US 2007/0160582 A1 Jul. 12, 2007

Related U.S. Application Data

(60) Provisional application No. 60/557,426, filed on Mar. 29, 2004, provisional application No. 60/554,833, filed on Mar. 19, 2004, provisional application No. 60/467,589, filed on May 2, 2003.

(51) Int. Cl.
*C12N 5/00* (2006.01)
*C12N 5/02* (2006.01)

(52) U.S. Cl. .......................... 435/377; 435/2; 435/7.21; 435/7.23; 435/7.24; 435/372; 435/373; 435/374; 435/384; 435/395; 436/63; 436/64; 436/175; 436/177; 436/178; 422/62; 422/101

(58) Field of Classification Search .................... 435/2, 435/372, 374, 377, 395, 402, 403, 7.21, 7.23, 435/7.243, 373, 384; 436/64, 177, 178, 63, 436/175; 422/44, 62, 68.1, 101
See application file for complete search history.

(56) References Cited

U.S. PATENT DOCUMENTS 5,759,793 A    6/1998  Schwartz et al.
5,837,444 A   11/1998  Shah
5,925,567 A    7/1999  Kraus (Continued)

OTHER PUBLICATIONS

Madlambayan et al., Manipulation of endogenous factor production enables in vitro stem and progenitor cell expansion: effects if cell selection and medium supplementation, Biosciences Information Service, Philadelphia, PA (Nov. 16, 2002) (Abstract).*

(Continued)

*Primary Examiner*—Gailene R Gabel
(74) *Attorney, Agent, or Firm*—Foley & Lardner LLP; Michel Morency; James F. Ewing

(57) ABSTRACT

The present invention provides an apparatus and methods for expansion of hematopoietic stem cell numbers. The stem cells are cultured and differentiated cells and endogenous growth factors are removed (depleted), permitting long term culture and expansion of the stem cells. The hematopoietic stem cells are used in numerous therapeutic procedures.

16 Claims, 18 Drawing Sheets

U.S. PATENT DOCUMENTS 6,338,942 B2 * 1/2002 Kraus et al. ..................... 435/2

OTHER PUBLICATIONS

Bhatia et al., Purification of primitive human hematopoietic cells capable of repopulating immune-deficient mice, Proc. Natl. Acad. Sci. USA 94: 5320-5325 (May 1997).*

Database Biosis (Online) Biosciences Information Service, Phladelphia, PA; Nov. 16, 2002, Madlambayan, Gerard J. et al., "Manipulation of endogenous factor production enables in vitro stem and progenitor cell expansion: effects of cell selection and medium supplementation" XP002313137 Database Accession No. PREV200300356575.

Bertolini, F., Battaglia, M., Pedrazzoli, P., Da Prada, G. A., Lanza, A., Soligo, D., Caneva, L., Sarina, B., Murphy, S., Thomas, T. & della Cuna, G. R. Megakaryocytic progenitors can be generated ex vivo and safely administered to autologous peripheral blood progenitor cell transplant recipients. Blood vol. 89, No. 8 2679-88—(1997).

Brugger, W., Heimfeld, S., Berenson, R. J., Mertelsmann, R. & Kanz, L. Reconstitution of hematopoiesis after high-dose chemotherapy by autologous progenitor cells generated ex vivo. N. Engl J Med vol. 333, No. 5 283-7—(1995).

Williams, S. F., Lee, W. J., Bender, J. G., Zimmerman, T., Swinney, P., Blake, M., Carreon, J., Schilling, M., Smith, S., Williams, D. E., Oldham, F. & Van Epps, D. Selection and expansion of peripheral blood CD34+ cells in autologous stem cell transplantation for breast cancer. Blood vol. 87, No. 5 1687-91—(1996).

Williams, D. A. Ex vivo expansion of hematopoietic stem and progenitor cells—robbing Peter to pay Paul? Blood vol. 81, No. 12 3169-72—(1993).

Gan, O. I., Murdoch, B., Larochelle, A. & Dick, J. E. Differential maintenance of primitive human SCID-repopulating cells, clonogenic progenitors, and long-term culture-initiating cells after incubation on human bone marrow stromal cells. Blood vol. 90, No. 2 641-50—(1997).

Bhatia, M., Wang, J. C., Kapp, U., Bonnet, D. & Dick, J. E. Purification of primitive human hematopoietic cells capable of repopulating immune-deficient mice. Proc Natl Acad Sci U S A vol. 94, No. 10—5320-5. (1997).

Ueda, T., Tsuji, K., Yoshino, H., Ebihara, Y., Yagasaki, H., Hisakawa, H., Mitsui, T., Manabe, A., Tanaka, R., Kobayashi, K., Ito, M., Yasukawa, K. & Nakahata, T. Expansion of human NOD/SCID-repopulating cells by stem cell factor, Flk2/Flt3 ligand, thrombopoietin, IL-6, and soluble IL-6 receptor [see comments]. J Clin Invest vol. 105, No. 7 1013-21—(2000).

McNiece, I. K., Almeida-Porada, G., Shpall, E. J. & Zanjani, E. Ex vivo expanded cord blood cells provide rapid engraftment in fetal sheep but lack long-term engrafting potential. Exp Hematol vol. 30, 612-6—(2002).

Conneally, E., Cashman, J., Petzer, A. & Eaves, C. Expansion in vitro of transplantable human cord blood stem cells demonstrated using a quantitative assay of their lympho-myeloid repopulating activity in nonobese diabetic-scid/scid mice. Proc Natl Acad Sci U S A vol. 94, No. 18—9836-41 (1997).

Glimm, H. & Eaves, C. J. Direct evidence for multiple self-renewal divisions of human in vivo repopulating hematopoietic cells in short-term culture. Blood vol. 94, No. 7 2161-8—(1999).

Denning-Kendall, P. A., Evely, R., Singha, S., Chapman, M., Bradley, B. A. & Hows, J. M. In vitro expansion of cord blood does not prevent engraftment of severe combined immunodeficient repopulating cells. Br J Haematol vol. 116, 218-28—2002).

Dick, J. E., Magli, M. C., Huszar, D., Phillips, R. A. & Bernstein, A. Introduction of a selectable gene into primitive stem cells capable of long-term reconstitution of the hemopoietic system of W/Wv mice. Cell vol. 42, 71-9.—(1985).

Osawa, M., Hanada, K., Hamada, H. & Nakauchi, H. Long-term lymphohematopoietic reconstitution by a single CD34-low/negative hematopoietic stem cell. Science vol. 273, 242-5. (1996).

Szilvassy, S. J., Humphries, R. K., Lansdorp, P. M., Eaves, A. C. & Eaves, C. J. Quantitative assay for totipotent reconstituting hematopoietic stem cells by a competitive repopulation strategy. Proc Natl Acad Sci U S A 87, 8736-40. (1990).

Guenechea, G., Gan, O. I., Dorrell, C. & Dick, J. E. Distinct classes of human stem cells that differ in proliferative and self-renewal potential. Nat Immunol vol. 2, No. 1 75-82.—(2001).

Keller, G. & Snodgrass, R. Life span of multipotential hematopoietic stem cells in vivo. J Exp Med vol. 171, 1407-18.—(1990).

Lemischka, I. R., Raulet, D. H. & Mulligan, R. C. Developmental potential and dynamic behavior of hematopoietic stem cells. Cell vol. 45, 917-27.—(1986).

Pawliuk, R., Eaves, C. & Humphries, R. K. Evidence of both ontogeny and transplant dose-regulated expansion of hematopoietic stem cells in vivo. Blood vol. 88, No. 8 2852-8—(1996).

Iscove, N. N. & Nawa, K. Hematopoietic stem cells expand during serial transplantation in vivo without apparent exhaustion. Curr Biol Vol. 7, No. 10 805-8—(1997).

Grotendorst, G. R., Smale, G. & Pencev, D. Production of transforming growth factor beta by human peripheral blood monocytes and neutrophils. J Cell Physiol vol. 140, 396-402—(1989).

Cluitmans, F. H., Esendam, B. H., Landegent, J. E., Willemze, R. & Falkenburg, J. H. Constitutive in vivo cytokine and hematopoietic growth factor gene expression in the bone marrow and peripheral blood of healthy individuals. Blood vol. 85, No. 8 2038-44—(1995).

Wickenhauser, C., Lorenzen, J., Thiele, J., Hillienhof, A., Jungheim, K., Schmitz, B., Hansmann, M. L. & Fischer, R. Secretion of cytokines (interleukins-1 alpha, -3, and -6 and granulocyte-macrophage colony-stimulating factor) by normal human bone marrow megakaryocytes. Blood vol. 85, No. 3 685-91—(1995).

Sautois, B., Fillet, G. & Beguin, Y. Comparative cytokine production by in vitro stimulated mononucleated cells from cord blood and adult blood. Exp Hematol vol. 25, 103-8—(1997).

Scapini, P., Lapinet-Vera, J. A., Gasperini, S., Calzetti, F., Bazzoni, F. & Cassatella, M. A. The neutrophil as a cellular source of chemokines. Immunol Rev vol. 177, 195-203—(2000).

Phillips, R. L., Ernst, R. E., Brunk, B., Ivanova, N., Mahan, M. A., Deanehan, J. K., Moore, K. A., Overton, G. C. & Lemischka, I. R. The genetic program of hematopoietic stem cells. Science vol. 288, p. 1635-40. (2000).

Majka, M., Janowska-Wieczorek, A., Ratajczak, J., Ehrenman, K., Pietrzkowski, Z., Kowalska, M. A., Gewirtz, A. M., Emerson, S. G. & Ratajczak, M. Z. Numerous growth factors, cytokines, and chemokines are secreted by human CD34(+) cells, myeloblasts, erythroblasts, and megakaryoblasts and regulate normal hematopoiesis in an autocrine/paracrine manner. Blood vol. 97, No. 10 3075-3085.—(2001).

Hariharan, D., Ho, W., Cutilli, J., Campbell, D. E. & Douglas, S. D. C-C chemokine profile of cord blood mononuclear cells: selective defect in Rantes production. Blood vol. 95, No. 2 715-8—2000).

Hornung, F., Scala, G. & Lenardo, M. J. Tnf-alpha-induced secretion of C-C chemokines modulates C-C chemokine receptor 5 expression on peripheral blood lymphocytes. J Immunol vol. 164, 6180-7—(2000).

Bluman, E. M., Bartynski, K. J., Avalos, B. R. & Caligiuri, M. A. Human natural killer cells produce abundant macrophage inflammatory protein-1 alpha in response to monocyte-derived cytokines. J Clin Invest vol. 97, No. 12 2722-7—(1996).

Dao, M. A., Hwa, J. & Nolta, J. A. Molecular mechanism of transforming growth factor beta-mediated cell-cycle modulation in primary human CD34(+) progenitors. Blood vol. 99, No. 2 499-506—(2002).

Broxmeyer, H. E., Sherry, B., Cooper, S., Lu, L., Maze, R., Beckmann, M. P., Cerami, A. & Ralph, P. Comparative analysis of the human macrophage inflammatory protein family of cytokines (chemokines) on proliferation of human myeloid progenitor cells. Interacting effects involving suppression, synergistic suppression, and blocking of suppression. J Immunol vol. 150, No. 8 3448-58—(1993).

Veiby, O. P., Jacobsen, F. W., Cui, L., Lyman, S. D. & Jacobsen, S. E. The flt3 ligand promotes the survival of primitive hemopoietic progenitor cells with myeloid as well as B lymphoid potential. Suppression of apoptosis and counteraction by TNF-alpha and TGF-beta. J Immunol vol. 157, 2953-60.—(1996).

Yonemura, Y., Ku, H., Hirayama, F., Souza, L. M. & Ogawa, M. Interleukin 3 or interleukin 1 abrogates the reconstituting ability of hematopoietic stem cells. Proc Natl Acad Sci U S A vol. 93, No. 9—4040-4 (1996).

Fukuda, T., Kamishima, T., Tsuura, Y., Suzuki, T., Kakihara, T., Naito, M., Kishi, K., Matsumoto, K., Shibata, A. & Seito, T. Expression of the c-kit gene product in normal and neoplastic mast cells but not in neoplastic basophil/mast cell precursors from chronic myelogenous leukaemia. J Pathol vol. 177, 139-46—(1995).

Lyman, S. D. & Jacobsen, S. E. c-kit ligand and Flt3 ligand: stem/progenitor cell factors with overlapping yet distinct activities. Blood vol. 91, No. 4 1101-34.—(1998).

Metcalf, D. & Nicola, N. A. Direct proliferative actions of stem cell factor on murine bone marrow cells in vitro: effects of combination with colony-stimulating factors. Proc Natl Acad Sci U S A 88, 6239-43 (1991).

Rappold, I., Ziegler, B. L., Kohler, I., Marchetto, S., Rosnet, O., Birnbaum, D., Simmons, P. J., Zannettino, A. C., Hill, B., Neu, S., Knapp, W., Alitalo, R., Alitalo, K., Ullrich, A., Kanz, L. & Buhring, H. J. Functional and phenotypic characterization of cord blood and bone marrow subsets expressing FLT3 (CD135) receptor tyrosine kinase. Blood vol. 90, No. 1 111-25—(1997).

Methia, N., Louache, F., Vainchenker, W. & Wendling, F. Oligodeoxynucleotides antisense to the proto-oncogene c-mpl specifically inhibit in vitro megakaryocytopoiesis. Blood vol. 82, No. 5 1395-401—(1993).

Sato, N., Caux, C., Kitamura, T., Watanabe, Y., Arai, K., Banchereau, J. & Miyajima, A. Expression and factor-dependent modulation of the interleukin-3 receptor subunits on human hematopoietic cells. Blood vol. 82, No. 3 752-61—(1993).

Wognum, A. W., de Jong, M. O. & Wagemaker, G. Differential expression of receptors for hemopoietic growth factors on subsets of CD34+ hemopoietic cells. Leuk Lymphoma vol. 24, 11-25—(1996).

Debili, N., Masse, J. M., Katz, A., Guichard, J., Breton-Gorius, J. & Vainchenker, W. Effects of the recombinant hematopoietic growth factors interleukin-3, interleukin-6, stem cell factor, and leukemia inhibitory factor on the megakaryocytic differentiation of CD34+ cells. Blood vol. 82, No. 1 84-95—(1993).

Lindemann, A., Herrmann, F., Oster, W., Haffner, G., Meyenburg, W., Souza, L. M. & Mertelsmann, R. Hematologic effects of recombinant human granulocyte colony-stimulating factor in patients with malignancy. Blood vol. 74, No. 8 2644-51—(1989).

Metcalf, D. Control of granulocytes and macrophages: molecular, cellular, and clinical aspects. Science vol. 254, 529-33—(1991).

Cashman, J. D., Clark-Lewis, I., Eaves, A. C. & Eaves, C. J. Differentiation stage-specific regulation of primitive human hematopoietic progenitor cycling by exogenous and endogenous inhibitors in an in vivo model. Blood vol. 94, No. 11 3722-9—(1999).

Dao, M. A., Taylor, N. & Nolta, J. A. Reduction in levels of the cyclin-dependent kinase inhibitor p27(kip-1) coupled with transforming growth factor beta neutralization induces cell-cycle entry and increases retroviral transduction of primitive human hematopoietic cells. Proc Natl Acad Sci U S A vol. 95, No. 22—13006-11 (1998).

Eaves, C. J., Cashman, J. D., Kay, R. J., Dougherty, G. J., Otsuka, T., Gaboury, L. A., Hogge, D. E., Lansdorp, P. M., Eaves, A. C. & Humphries, R. K. Mechanisms that regulate the cell cycle status of very primitive hematopoietic cells in long-term human marrow cultures. Ii. Analysis of positive and negative regulators produced by stromal cells within the adherent layer. Blood vol. 78, No. 1 110-7—(1991).

Batard, P., Monier, M. N., Fortunel, N., Ducos, K., Sansilvestri-Morel, P., Phan, T., Hatzfeld, A. & Hatzfeld, J. A. TGF-(beta)1 maintains hematopoietic immaturity by a reversible negative control of cell cycle and induces CD34 antigen up-modulation. J Cell Sci vol. 113, 383-90—(2000).

Cashman, J. D., Eaves, C. J., Sarris, A. H. & Eaves, A. C. MCP-1, not MIP-1alpha, is the endogenous chemokine that cooperates with TGF-beta to inhibit the cycling of primitive normal but not leukemic (CML) progenitors in long-term human marrow cultures. Blood vol. 92, No. 7 2338-44.—(1998).

Guba, S. C., Sartor, C. I., Gottschalk, L. R., Jing, Y. H., Mulligan, T. & Emerson, S. G. Bone marrow stromal fibroblasts secrete interleukin-6 and granulocyte-macrophage colony-stimulating factor in the absence of inflammatory stimulation: demonstration by serum-free bioassay, enzyme-linked immunosorbent assay, and reverse transcriptase polymerase chain reaction. Blood vol. 80, No. 5 1190-8—(1992).

Cashman, J., Clark-Lewis, I., Eaves, A. & Eaves, C. Stromal-derived factor 1 inhibits the cycling of very primitive human hematopoietic cells in vitro and in NOD/SCID mice. Blood vol. 99, No. 3 792-9—(2002).

Fortunel, N., Hatzfeld, J., Kisselev, S., Monier, M. N., Ducos, K., Cardoso, A., Batard, P. & Hatzfeld, A. Release from quiescence of primitive human hematopoietic stem/progenitor cells by blocking their cell-surface TGF-beta type II receptor in a short-term in vitro assay. Stem Cells 18, 102-11 (2000).

Sutherland, H. J., Eaves, C. J., Eaves, A. C., Dragowska, W. & Lansdorp, P. M. Characterization and partial purification of human marrow cells capable of initiating long-term hematopoiesis in vitro. Blood vol. 74, No. 5 1563-70—(1989).

Sutherland, H. J., Lansdorp, P. M., Henkelman, D. H., Eaves, A. C. & Eaves, C. J. Functional characterization of individual human hematopoietic stem cells cultured at limiting dilution on supportive marrow stromal layers. Proc Natl Acad Sci U S A 87, 3584-8 (1990).

Sutherland, H. J., Eaves, C. J., Lansdorp, P. M., Thacker, J. D. & Hogge, D. E. Differential regulation of primitive human hematopoietic cells in long-term cultures maintained on genetically engineered murine stromal cells. Blood vol. 78, No. 3 666-72—(1991).

Hogge, D. E., Lansdorp, P. M., Reid, D., Gerhard, B. & Eaves, C. J. Enhanced detection, maintenance, and differentiation of primitive human hematopoietic cells in cultures containing murine fibroblasts engineered to produce human steel factor, interleukin-3, and granulocyte colony-stimulating factor. Blood vol. 88, No. 10 3765-73.—(1996).

Till, J. E. & Mc, C. E. A direct measurement of the radiation sensitivity of normal mouse bone marrow cells. Radiat Res 14, 213-222 (1961).

Horn, P. A., Thomasson, B. M., Wood, B. L., Andrews, R. G., Morris, J. C. & Kiem, H. P. Distinct hematopoietic stem/progenitor cell populations are responsible for repopulating NOD/SCID mice compared with nonhuman primates. Blood vol. 102, No. 13 4329-35—(2003).

Nolta, J. A., Hanley, M. B. & Kohn, D. B. Sustained human hematopoiesis in immunodeficient mice by cotransplantation of marrow stroma expressing human interleukin-3: analysis of gene transduction of long-lived progenitors. Blood vol. 83, No. 10 3041-51—(1994).

McCune, J. M., Namikawa, R., Kaneshima, H., Shultz, L. D., Lieberman, M. & Weissman, I. L. The SCID-hu mouse: murine model for the analysis of human hematolymphoid differentiation and function. Science 241, 1632-9 (1988).

Zanjani, E. D. The human sheep xenograft model for the study of the in vivo potential of human HSC and in utero gene transfer. Stem Cells 18, 151 (2000).

Lapidot, T., Pflumio, F., Doedens, M., Murdoch, B., Williams, D. E. & Dick, J. E. Cytokine stimulation of multilineage hematopoiesis from immature human cells engrafted in Scid mice. Science vol. 255, 1137-41—(1992).

Kamel-Reid, S. & Dick, J. E. Engraftment of immune-deficient mice with human hematopoietic stem cells. Science vol. 242, 1706-9. (1988).

Dick, J. E. Normal and leukemic human stem cells assayed in Scid mice. Semin Immunol vol. 8, pp. 197-206—(1996).

Hogan, C. J., Shpall, E. J., McNulty, O., McNiece, I., Dick, J. E., Shultz, L. D. & Keller, G. Engraftment and development of human CD34(+)-enriched cells from umbilical cord blood in NOD/LtSz-scid/scid mice. Blood vol. 90, No. 1 85-96—(1997).

Cashman, J. D., Lapidot, T., Wang, J. C., Doedens, M., Shultz, L. D., Lansdorp, P., Dick, J. E. & Eaves, C. J. Kinetic evidence of the regeneration of multilineage hematopoiesis from primitive cells in normal human bone marrow transplanted into immunodeficient mice. Blood vol. 89, No. 12 4307-16—(1997).

Wang, J. C., Doedens, M. & Dick, J. E. Primitive human hematopoietic cells are enriched in cord blood compared with adult bone marrow or mobilized peripheral blood as measured by the quantitative in vivo SCID-repopulating cell assay. Blood vol. 89, No. 11 3919-24—(1997).

Krause, D. S., Fackler, M. J., Civin, C. I. & May, W. S. CD34: structure, biology, and clinical utility. Blood vol. 87, No. 1 1-13. —(1996).

Sauvageau, G., Lansdorp, P. M., Eaves, C. J., Hogge, D. E., Dragowska, W. H., Reid, D. S., Largman, C., Lawrence, H. J. & Humphries, R. K. Differential expression of homeobox genes in functionally distinct CD34+ subpopulations of human bone marrow cells. Proc Natl Acad Sci U S A vol. 91, No. 25—12223-7 (1994).

Goodell, M. A., Brose, K., Paradis, G., Conner, A. S. & Mulligan, R. C. Isolation and functional properties of murine hematopoietic stem cells that are replicating in vivo. J Exp Med vol. 183, 1797-806—(1996).

Goodell, M. A., Rosenzweig, M., Kim, H., Marks, D. F., DeMaria, M., Paradis, G., Grupp, S. A., Sieff, C. A., Mulligan, R. C. & Johnson, R. P. Dye efflux studies suggest that hematopoietic stem cells expressing low or undetectable levels of CD34 antigen exist in multiple species. Nat Med vol. 3, No. 12 1337-45—(1997).

Bhatia, M., Bonnet, D., Murdoch, B., Gan, O. I. & Dick, J. E. A newly discovered class of human hematopoietic cells with SCID-repopulating activity [see comments]. Nat Med vol. 4, No. 9 1038-45—(1998).

Zanjani, E. D., Almeida-Porada, G., Livingston, A. G., Flake, A. W. & Ogawa, M. Human bone marrow CD34- cells engraft in vivo and undergo multilineage expression that includes giving rise to CD34+ cells. Exp Hematol vol. 26, 353-60—(1998).

Baume, C. M., Weissman, I. L., Tsukamoto, A. S., Buckle, A. M. & Peault, B. Isolation of a candidate human hematopoietic stem-cell population. Proc Natl Acad Sci U S A vol. 89, No. 7—2804-8. (1992).

Craig, W., Kay, R., Cutler, R. L. & Lansdorp, P. M. Expression of Thy-1 on human hematopoietic progenitor cells. J Exp Med vol. 177, 1331-42. (1993).

Uchida, N., Aguila, H. L., Fleming, W. H., Jerabek, L. & Weissman, I. L. Rapid and sustained hematopoietic recovery in lethally irradiated mice transplanted with purified Thy-1.110 Lin-Sca-1+ hematopoietic stem cells. Blood vol. 83, No. 12 3758-79—(1994).

Pasino, M., Lanza, T., Marotta, F., Scarso, L., De Biasio, P., Amato, S., Corcione, A., Pistoia, V. & Mori, P. G. Flow cytometric and functional characterization of AC133+ cells from human umbilical cord blood. Br J Haematol vol. 108, 793-800.—(2000).

Handgretinger, R., Gordon, P. R., Leimig, T., Chen, X., Buhring, H. J., Niethammer, D. & Kuci, S. Biology and plasticity of CD133+ hematopoietic stem cells. Ann N Y Acad Sci vol. 996, 141-51—(2003).

de Wynter, E. A., Buck, D., Hart, C., Heywood, R., Coutinho, L. H., Clayton, a., Rafferty, J. A., Burt, D., Guenechea, G., Bueren, J. A., Gagen, D., Fairbairn, L. J., Lord, B. I. & Testa, N. G. CD34+AC133+ cells isolated from cord blood are highly enriched in long-term culture-initiating cells, NOD/SCID-repopulating cells and dendritic cell progenitors. Stem Cells 16, 387-96 (1998).

Ziegler, B. L., Valtieri, M., Porada, G. A., De Maria, R., Muller, R., Masella, B., Gabbianelli, M., Casella, I., Pelosi, E., Bock, T., Zanjani, E. D. & Peschle, C. KDR receptor: a key marker defining hematopoietic stem cells. Science vol. 285, p. 1553-8 (1999).

Srour, E. F., Brandt, J. E., Briddell, R. A., Leemhuis, T., van Besien, K. & Hoffman, R. Human CD34+ HLA-DR- bone marrow cells contain progenitor cells capable of self-renewal, multilineage differentiation, and long-term in vitro hematopoiesis. Blood Cells 17, 287-95 (1991).

Mayani, H. & Lansdorp, P. M. Proliferation of individual hematopoietic progenitors purified from umbilical cord blood. Exp Hematol 23, 1453-62 (1995).

Audet, J., Zandstra, P. W., Eaves, C. J. & Piret, J. M. Advances in hematopoietic stem cell culture. Curr Opin Biotechnol vol. 9, 146-51—(1998).

Ihle, J. N. Cytokine receptor signalling. Nature vol. 377, 591-4—(1995).

Haylock, D. N., Horsfall, M. J., Dowse, T. L., Ramshaw, H. S., Niutta, S., Protopsaltis, S., Peng, L., Burrell, C., Rappold, I., Buhring, H. J. & Simmons, P. J. Increased recruitment of hematopoietic progenitor cells underlies the ex vivo expansion potential of FLT3 ligand. Blood vol. 90, No. 6 2260-72.—(1997).

Broudy, V. C. Stem cell factor and hematopoiesis. Blood vol. 90, No. 4 1345-64.—(1997).

Kimura, T., Wang, J., Minamiguchi, H., Fujiki, H., Harada, S., Okuda, K., Kaneko, H., Yokota, S., Yasukawa, K., Abe, T. & Sonoda, Y. Signal through gp130 activated by soluble interleukin (IL)-6 receptor (R) and IL-6 or IL-6R/IL-6 fusion protein enhances ex vivo expansion of human peripheral blood-derived hematopoietic progenitors. Stem Cells 18, 444-52 (2000).

Yagi, M., Ritchie, K. A., Sitnicka, E., Storey, C., Roth, G. J. & Bartelmez, S. Sustained ex vivo expansion of hematopoietic stem cells mediated by thrombopoietin. Proc Natl Acad Sci U S A vol. 96, No. 14—8126-31 (1999).

Ikebuchi, K., Wong, G. G., Clark, S. C., Ihle, J. N., Hirai, Y. & Ogawa, M. Interleukin 6 enhancement of interleukin 3-dependent proliferation of multipotential hemopoietic progenitors. Proc Natl Acad Sci U S A 84, 9035-9 (1987).

Neben, S., Donaldson, D., Sieff, C., Mauch, P., Bodine, D., Ferrara, J., Yetz-Aldape, J. & Turner, K. Synergistic effects of interleukin-11 with other growth factors on the expansion of murine hematopoietic progenitors and maintenance of stem cells in liquid culture. Exp Hematol vol. 22, 353-9—(1994).

Ikebuchi, K., Clark, S. C., Ihle, J. N., Souza, L. M. & Ogawa, M. Granulocyte colony-stimulating factor enhances interleukin 3-dependent proliferation of multipotential hemopoietic progenitors. Proc Natl Acad Sci U S A 85, 3445-9 (1988).

Hirayama, F., Katayama, N., Neben, S., Donaldson, D., Nickbarg, E. B., Clark, S. C. & Ogawa, M. Synergistic interaction between interleukin-12 and steel factor in support of proliferation of murine lymphohematopoietic progenitors in culture. Blood vol. 83, No. 1 92-8—(1994).

Bagby, G. C., Jr. Interleukin-1 and hematopoiesis. Blood Rev vol. 3, 152-61—(1989).

Metcalf, D., Burgess, A. W., Johnson, G. R., Nicola, N. A., Nice, E. C., DeLamarter, J., Thatcher, D. R. & Mermod, J. J. In vitro actions on hemopoietic cells of recombinant murine GM-CSF purified after production in *Escherichia coli*: comparison with purified native GM-CSF. J Cell Physiol vol. 128, 421-31—(1986).

Ramsfjell, V., Borge, O. J., Cui, L. & Jacobsen, S. E. Thrombopoietin directly and potently stimulates multilineage growth and progenitor cell expansion from primitive (CD34+ CD38-) human bone marrow progenitor cells: distinct and key interactions with the ligands for c-kit and flt3, and inhibitory effects of TGF-beta and TNF-alpha. J Immunol vol. 158, 5169-77—(1997).

Haylock, D. N., To, L. B., Dowse, T. L., Juttner, C. A. & Simmons, P. J. Ex vivo expansion and maturation of peripheral blood CD34+ cells into the myeloid lineage. Blood vol. 80, No. 6 1405-12—(1992).

Sitnicka, E., Ruscetti, F. W., Priestley, G. V., Wolf, N. S. & Bartelmez, S. H. Transforming growth factor beta 1 directly and reversibly inhibits the initial cell divisions of long-term repopulating hematopoietic stem cells. Blood vol. 88, No. 1 82-8—(1996).

Jacobsen, S. E., Keller, J. R., Ruscetti, F. W., Kondaiah, P., Roberts, A. B. & Falk, L. A. Bidirectional effects of transforming growth factor beta (TGF-beta) on colony-stimulating factor-induced human myelopoiesis in vitro: differential effects of distinct TGF-beta isoforms. Blood vol. 78, No. 9 2239-47—(1991).

Ottmann, O. G. & Pelus, L. M. Differential proliferative effects of transforming growth factor-beta on human hematopoietic progenitor cells. J Immunol vol. 140, No. 8 2661-5—(1988).

Van Ranst, P. C., Snoeck, H. W., Lardon, F., Lenjou, M., Nijs, G., Weekx, S. F., Rodrigus, I., Berneman, Z. N. & Van Bockstaele, D. R. TGF-beta and MIP-1 alpha exert their main inhibitory activity on very primitive CD34+2CD38- cells but show opposite effects on more mature CD34+CD38+ human hematopoietic progenitors. Exp Hematol vol. 24, 1509-15—(1996).

Fortunel, N. O., Hatzfeld, A. & Hatzfeld, J. A. Transforming growth factor-beta: pleiotropic role in the regulation of hematopoiesis. Blood vol. 96, No. 6 2022-36—(2000).

Heinrich, M. C., Dooley, D. C. & Keeble, W. W. Transforming growth factor beta 1 inhibits expression of the gene products for steel factor and its receptor (c-kit). Blood vol. 85, No. 7 1769-80—(1995).

Sansilvestri, P., Cardoso, A. A., Batard, P., Panterne, B., Hatzfeld, A., Lim, B., Levesque, J. P., Monier, M. N. & Hatzfeld, J. Early CD34high cells can be separated into KIThigh cells in which transforming growth factor-beta (TGF-beta) downmodulates c-kit and KITlow cells in which anti-TGF-beta upmodulates c-kit. Blood vol. 86, No. 5 1729-35—(1995).

Fortunel, N., Batard, P., Hatzfeld, A., Monier, M. N., Panterne, B., Lebkowski, J. & Hatzfeld, J. High proliferative potential-quiescent cells: a working model to study primitive quiescent hematopoietic cells. J Cell Sci vol. 111, 1867-75—(1998).

Broxmeyer, H. E., Sherry, B., Lu, L., Cooper, S., Oh, K. O., Tekamp-Olson, P., Kwon, B. S. & Cerami, A. Enhancing and suppressing effects of recombinant murine macrophage inflammatory proteins on colony formation in vitro by bone marrow myeloid progenitor cells. Blood vol. 76, No. 6 1110-6—(1990).

Broxmeyer, H. E. & Kim, C. H. Regulation of hematopoiesis in a sea of chemokine family members with a plethora of redundant activities. Exp Hematol vol. 27, 1113-23—(1999).

Lu, L., Xiao, M., Grigsby, S., Wang, W. X., Wu, B., Shen, R. N. & Broxmeyer, H. E. Comparative effects of suppressive cytokines on isolated single CD34(3+) stem/progenitor cells from human bone marrow and umbilical cord blood plated with and without serum. Exp Hematol vol. 21, 1442-6—(1993).

Cooper, S., Mantel, C. & Broxmeyer, H. E. Myelosuppressive effects in vivo with very low dosages of monomeric recombinant murine macrophage inflammatory protein-1 alpha. Exp Hematol vol. 22, 186-93—(1994).

Lord, B. I., Dexter, T. M., Clements, J. M., Hunter, M. A. & Gearing, A. J. Macrophage-inflammatory protein protects multipotent hematopoietic cells from the cytotoxic effects of hydroxyurea in vivo. Blood vol. 79, No. 10 2605-9—(1992).

Mayani, H., Little, M. T., Dragowska, W., Thornbury, G. & Lansdorp, P. M. Differential effects of the hematopoietic inhibitors MIP-1 alpha, TGF-beta, and TNF-alpha on cytokine-induced proliferation of subpopulations of CD34+ cells purified from cord blood and fetal liver. Exp Hematol vol. 23, 422-7—(1995).

Zandstra, P. W., Eaves, C.J., and Piret, J.M. in Ex Vivo Cell Therapy (ed. Schindhelm, K. a. N., R) 245-272 (Academic Press, San Diego, 1999).

Zandstra, P. W., Conneally, E., Petzer, A. L., Piret, J. M. & Eaves, C. J. Cytokine manipulation of primitive human hematopoietic cell self-renewal. Proc Natl Acad Sci U S A vol. 94, No. 9—4698-703 (1997).

Jo, D. Y., Rafii, S., Hamada, T. & Moore, M. A. Chemotaxis of primitive hematopoietic cells in response to stromal cell-derived factor-1. J Clin Invest vol. 105, No. 1 101-11—(2000).

Rusten, L. S., Smeland, E. B., Jacobsen, F. W., Lien, E., Lesslauer, W., Loetscher, H., Dubois, C. M. & Jacobsen, S. E. Tumor necrosis factor-alpha inhibits stem cell factor-induced proliferation of human bone marrow progenitor cells in vitro. Role of p55 and p75 tumor necrosis factor receptors. J Clin Invest vol. 94, 165-72—(1994).

Jacobsen, S. E., Veiby, O. P., Myklebust, J., Okkenhaug, C. & Lyman, S. D. Ability of flt3 ligand to stimulate the in vitro growth of primitive murine hematopoietic progenitors is potently and directly inhibited by transforming growth factor-beta and tumor necrosis factor-alpha. Blood vol. 87, No. 12 5016-26—(1996).

Jacobsen, F. W., Veiby, 0. P., Stokke, T. & Jacobsen, S. E. TNF-alpha bidirectionally modulates the viability of primitive murine hematopoietic progenitor cells in vitro. J Immunol vol. 157, 1193-9. —(1996).

Nagata, S. & Golstein, P. The Fas death factor. Science vol. 267, 1449-56. (1995).

Glimm, H., Tang, P., Clark-Lewis, I., von Kalle, C. & Eaves, C. Ex vivo treatment of proliferating human cord blood stem cells with stroma-derived factor-1 enhances their ability to engraft NOD/SCID mice. Blood vol. 99, No. 9 3454-7—(2002).

Peled, A., Petit, I., Kollet, O., Magid, M., Ponomaryov, T., Byk, T., Nagler, A., Ben-Hur, H., Many, A., Shultz, L., Lider, O., Alon, R., Zipori, D. & Lapidot, T. Dependence of human stem cell engraftment and repopulation of NOD/SCID mice on CXCR4. Science vol. 283, p. 845-8 (1999).

Rocha, V., Cornish, J., Sievers, E. L., Filipovich, A., Locatelli, F., Peters, C., Remberger, M., Michel, G., Arcese, W., Dallorso, S., Tiedemann, K., Busca, A., Chan, K. W., Kato, S., Ortega, J., Vowels, M., Zander, A., Souillet, G., Oakill, A., Woolfrey, A., Pay, A. L., Green, A., Garnier, F., Ionescu, I., Wernet, P., Sirchia, G., Rubinstein, P., Chevret, S. & Gluckman, E. Comparison of outcomes of unrelated bone marrow and umbilical cord blood transplants in children with acute leukemia. Blood vol. 97, No. 10 2962-71—(2001).

Wagner, J. E., Barker, J. N., DeFor, T. E., Baker, K. S., Blazar, B. R., Eide, C., Goldman, A., Kersey, J., Krivit, W., MacMillan, M. L., Orchard, P. J., Peters, C., Weisdorf, D. J., Ramsay, N. K. & Davies, S. M. Transplantation of unrelated donor umbilical cord blood in 102 patients with malignant and nonmalignant diseases: influence of CD34 cell dose and HLA disparity on treatment-related mortality and survival. Blood vol. 100, No. 5 1611-8—(2002).

Rubinstein, P., Carrier, C., Scaradavou, A., Kurtzberg, J., Adamson, J., Migliaccio, A. R., Berkowitz, R. L., Cabbad, M., Dobrila, N. L., Taylor, P. E., Rosenfield, R. E. & Stevens, C. E. Outcomes among 562 recipients of placental-blood transplants from unrelated donors [see comments]. N. Engl J Med vol. 339, No. 22 1565-77—(1998).

Rogers, I., Sutherland, Holt, D., Macpate, F., Lains, A., Hollowell, S., Cruickshank, B. & Casper, R. F. Human UC-blood banking: impact of blood volume, cell separation and cryopreservation on leukocyte and CD34(+) cell recovery. Cytotherapy vol. 3, No. 4 269-76—(2001).

Mazurier, F., Doedens, M., Gan, O. I. & Dick, J. E. Rapid myeloerythroid repopulation after intrafemoral transplantation of NOD-SCID mice reveals a new class of human stem cells. Nat Med vol. 9, No. 7 959-63—(2003).

Murphy, L. D., Herzog, C. E., Rudick, J. B., Fojo, A. T. & Bates, S. E. Use of the polymerase chain reaction in the quantitation of Mdr-1 gene expression. Biochemistry vol. 29, 10351-6—(1990).

Taswell, C. Limiting dilution assays for the determination of immunocompetent cell frequencies. I. Data analysis. J Immunol vol. 126, No. 4 1614-9—(1981).

Gluckman, E., Rocha, V., Boyer-Chammard, A., Locatelli, F., Arcese, W., Pasquini, R., Ortega, J., Souillet, G., Ferreira, E., Laporte, J. P., Fernandez, M. & Chastang, C. Outcome of cord-blood transplantation from related and unrelated donors. Eurocord Transplant Group and the European Blood and Marrow Transplantation Group. N. Engl J Med vol. 337, No. 6 373-81—(1997).

Wagner, J. E., Rosenthal, J., Sweetman, R., Shu, X. O., Davies, S. M., Ramsay, N. K., McGlave, P. B., Sender, L. & Cairo, M. S. Successful transplantation of HLA-matched and HLA-mismatched umbilical cord blood from unrelated donors: analysis of engraftment and acute graft-versus-host disease. Blood vol. 88, No. 3 795-802—(1996).

Wagner, J. E., Kernan, N. A., Steinbuch, M., Broxmeyer, H. E. & Gluckman, E. Allogeneic sibling umbilical-cord-blood transplantation in children with malignant and non-malignant disease. Lancet vol. 346, 214-9—(1995).

Barker, J. N. & Wagner, J. E. Umbilical-cord blood transplantation for the treatment of cancer. Nat Rev Cancer vol. 3, 526-32—(2003).

Broxmeyer, H. E., Srour, E. F., Hangoc, G., Cooper, S., Anderson, S. A. & Bodine, D. M. High-efficiency recovery of functional hematopoietic progenitor and stem cells from human cord blood cryopreserved for 15 years. Proc Natl Acad Sci U S A vol. 100, No. 2—645-50 (2003).

Broxmeyer, H. E., Hangoc, G., Cooper, S., Ribeiro, R. C., Graves, V., Yoder, M., Wagner, J., Vadhan-Raj, S., Benninger, L., Rubinstein, P. & et al. Growth characteristics and expansion of human umbilical cord blood and estimation of its potential for transplantation in adults. Proc Natl Acad Sci U S A vol. 89, No. 9—4109-13 (1992).

Wagner, J. E., Broxmeyer, H. E., Byrd, R. L., Zehnbauer, B., Schmeckpeper, B., Shah, N., Griffin, C., Emanuel, P. D., Zuckerman, K. S., Cooper, S. & et al. Transplantation of umbilical cord blood after myeloablative therapy: analysis of engraftment [see comments]. Blood vol. 79, No. 7 1874-81—(1992).

Bachier, C. R., Gokmen, E., Teale, J., Lanzkron, S., Childs, C., Franklin, W., Shpall, E., Douville, J., Weber, S., Muller, T., Armstrong, D. & LeMaistre, C. F. Ex-vivo expansion of bone marrow progenitor cells for hematopoietic reconstitution following high-dose chemotherapy for breast cancer. Exp Hematol vol. 27, 615-23—(1999).

McNiece, I., Jones, R., Bearman, S. I., Cagnoni, P., Nieto, Y., Franklin, W., Ryder, J., Steele, A., Stoltz, J., Russell, P., McDermitt, J., Hogan, C., Murphy, J. & Shpall, E. J. Ex vivo expanded peripheral blood progenitor cells provide rapid neutrophil recovery after high-dose chemotherapy in patients with breast cancer. Blood vol. 96, No. 9 3001-7—(2000).

Paquette, R. L., Dergham, S. T., Karpf, E., Wang, H. J., Slamon, D. J., Souza, L. & Glaspy, J. A. Ex vivo expanded unselected peripheral blood: progenitor cells reduce posttransplantation neutropenia, thrombocytopenia, and anemia in patients with breast cancer. Blood vol. 96, No. 7 2385-90—(2000).

Reiffers, J., Cailliot, C., Dazey, B., Attal, M., Caraux, J. & Boiron, J. M. Abrogation of post-myeloablative chemotherapy neutropenia by ex-vivo expanded autologous CD34- positive cells. Lancet vol. 354, 1092-3—(1999).

Stiff, P., Chen, B., Franklin, W., Oldenberg, D., Hsi, E., Bayer, R., Shpall, E., Douville, J., Mandalam, R., Malhotra, D., Muller, T., Armstrong, R. D. & Smith, A. Autologous transplantation of ex vivo expanded bone marrow cells grown from small aliquots after high-dose chemotherapy for breast cancer. Blood vol. 95, No. 6 2169-74—(2000).

Devine, S. M., Lazarus, H. M. & Emerson, S. G. Clinical application of hematopoietic progenitor cell expansion: current status and future prospects. Bone Marrow Transplant vol. 31, 241-52—(2003).

Collins, P. C., Miller, W. M. & Papoutsakis, E. T. Stirred culture of peripheral and cord blood hematopoietic cells offers advantages over traditional static systems for clinically relevant applications. Biotechnol Bioeng vol. 59, 534-43—(1998).

Zandstra, P. W., Eaves, C. J. & Piret, J. M. Expansion of hematopoietic progenitor cell populations in stirred suspension bioreactors of normal human bone marrow cells. Biotechnology (N Y) vol. 12, p. 909-14.—(1994).

Koller, M. R., Bender, J. G., Miller, W. M. & Papoutsakis, E. T. Expansion of primitive human hematopoietic progenitors in a perfusion bioreactor system with IL-3, IL-6, and stem cell factor. Biotechnology (N Y) vol. 11, 358-63—(1993).

Heike, T. & Nakahata, T. Ex vivo expansion of hematopoietic stem cells by cytokines. Biochim Biophys Acta 1592, 313-21 (2002).

Bhatia, M., Bonnet, D., Kapp, U., Wang, J. C., Murdoch, B. & Dick, J. E. Quantitative analysis reveals expansion of human hematopoietic repopulating cells after short-term ex vivo culture. J Exp Med vol. 186, No. 4 619-24—(1997).

Bhardwaj, G., Murdoch, B., Wu, D., Baker, D. P., Williams, K. P., Chadwick, K., Ling, L. E., Karanu, F. N. & Bhatia, M. Sonic hedgehog induces the proliferation of primitive human hematopoietic cells via BMP regulation. Nat Immunol vol. 2, No. 2 172-80—(2001).

Antonchuk, J., Sauvageau, G. & Humphries, R. K. HOXB4-induced expansion of adult hematopoietic stem cells ex vivo. Cell vol. 109, 39-45—(2002).

Reya, T., Duncan, A. W., Ailles, L., Domen, J., Scherer, D. C., Willert, K., Hintz, L., Nusse, R. & Weissman, I. L. A role for Wnt signalling in self-renewal of haematopoietic stem cells. Nature vol. 423, 409-14—(2003).

Mazurier, F., Gan, O. I., McKenzie, J. L., Doedens, M. & Dick, J. E. Lentivector-mediated clonal tracking reveals intrinsic heterogeneity in the human hematopoietic stem cell compartment and culture-induced stem cell impairment. Blood vol. 103, No. 2 545-552—(2004).

Wright, D. E., Wagers, A. J., Gulati, A. P., Johnson, F. L. & Weissman, I. L. Physiological migration of hematopoietic stem and progenitor cells. Science vol. 294, p. 1933-6 (2001).

Schwartz, R. M., Palsson, B. O. & Emerson, S. G. Rapid medium perfusion rate significantly increases the productivity and longevity of human bone marrow cultures. Proc Natl Acad Sci U S A vol. 88, No. 15—6760-4 (1991).

Caldwell, J., Palsson, B. O., Locey, B. & Emerson, S. G. Culture perfusion schedules influence the metabolic activity and granulocyte-macrophage colony-stimulating factor production rates of human bone marrow stromal cells. J Cell Physiol vol. 147, 344-53—(1991).

Koller, M. R., Palsson, M. A., Manchel, I. & Palsson, B. O. Long-term culture-initiating cell expansion is dependent on frequent medium exchange combined with stromal and other accessory cell effects. Blood vol. 86, No. 5 1784-93—(1995).

Pilarski, L.M., Belch, A.R. Circulating Monoclonal B Cells Expressing P Glycoprotein May Be a Reservoir of Multidrug-Resistant Disease in Multiple Myeloma. Blood, vol. 83, No. 3 (Feb. 1), 724-736 (1994).

Civin, C.I. How do we Translate Gene Therapy to Clinical Trials? Stem Cells 18, 150-151 (2000).

Bodine, D.M., Barrette, S., Seidel, N., Orlic, D., Miller A.D. Transduction of Mouse Hematopoietic Stem Cells is More Efficient with 10A1 Retrovirus Vectors than with Amphotropic Vectors. Stem Cells 18, 152-153 (2000).

Kurtzberg, J., Martin, P., Chao, N., Stevens, C., Rubinstein, P. Unrelated Placental Blood in Marrow Transplantation. Stem Cells 18, 153-154 (2000).

Shadduck, R.K., Gilmore, G.L., Lister, J. Stem Cells 18, 154-155 (2000).

Malech, H.L., Use of Serum-Free Medium with Fibronectin Fragment Enhanced Transduction in a System of Gas Permeable Plastic Containers to Achieve High Levels of Retrovirus Transduction at Clinical Scale. Stem Cells 18, 155-156 (2000).

* cited by examiner

Figure 2.
A.
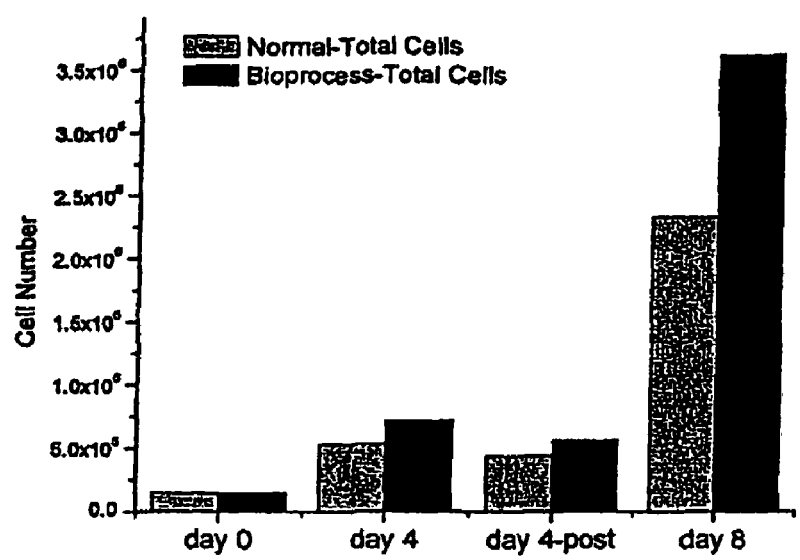
B.
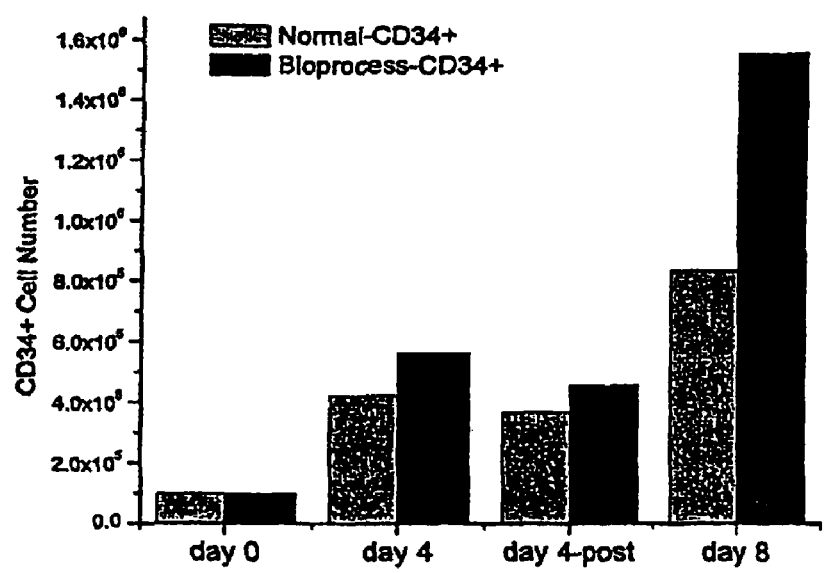

Figure 2.
C.
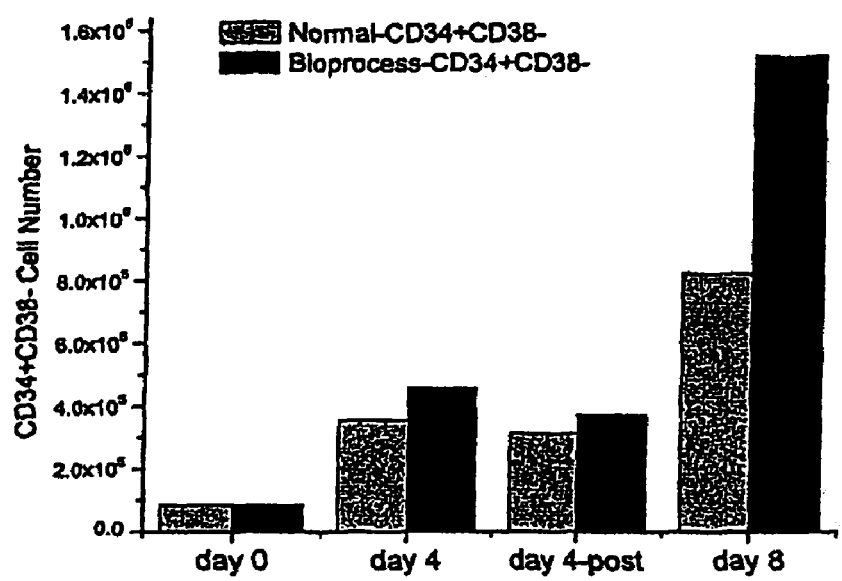
D.
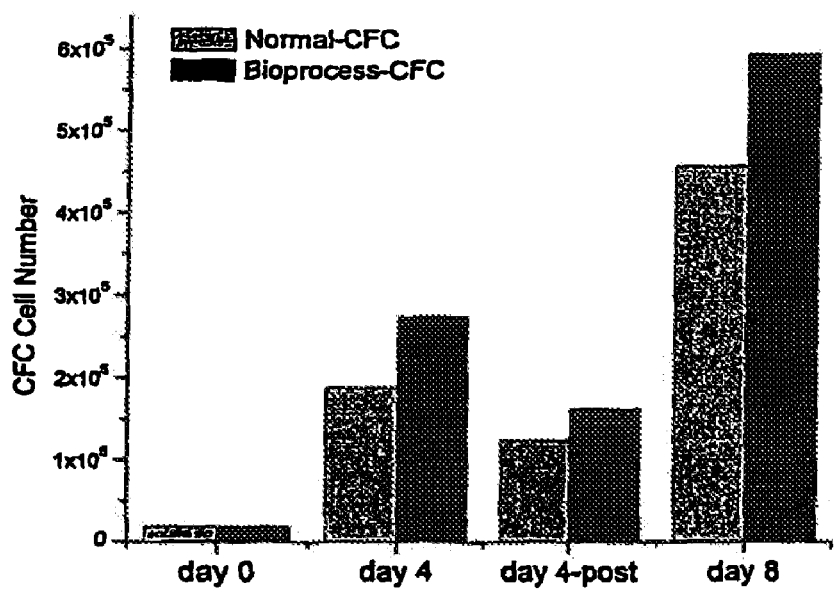

Figure 5.
A.
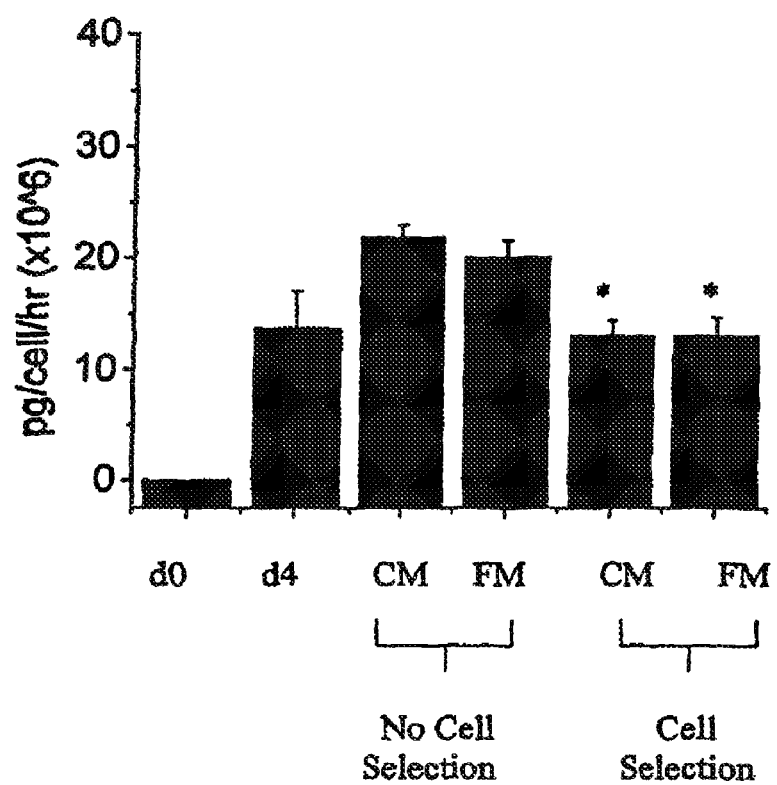
B.
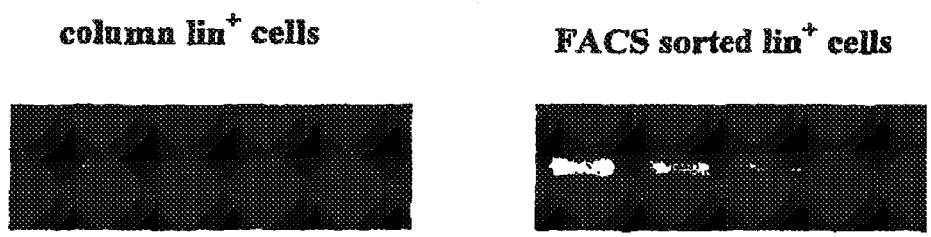

A.
Figure 6.
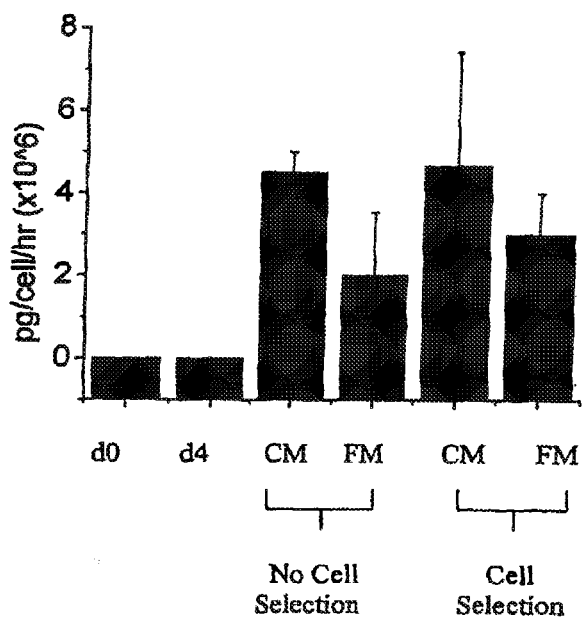
B.
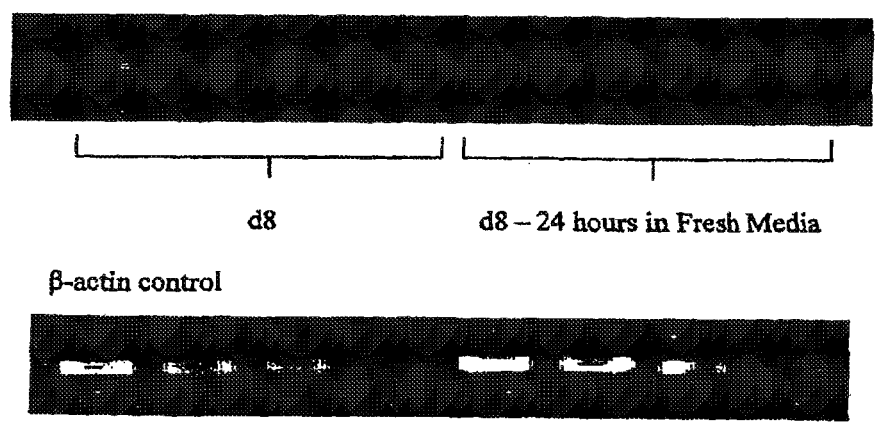

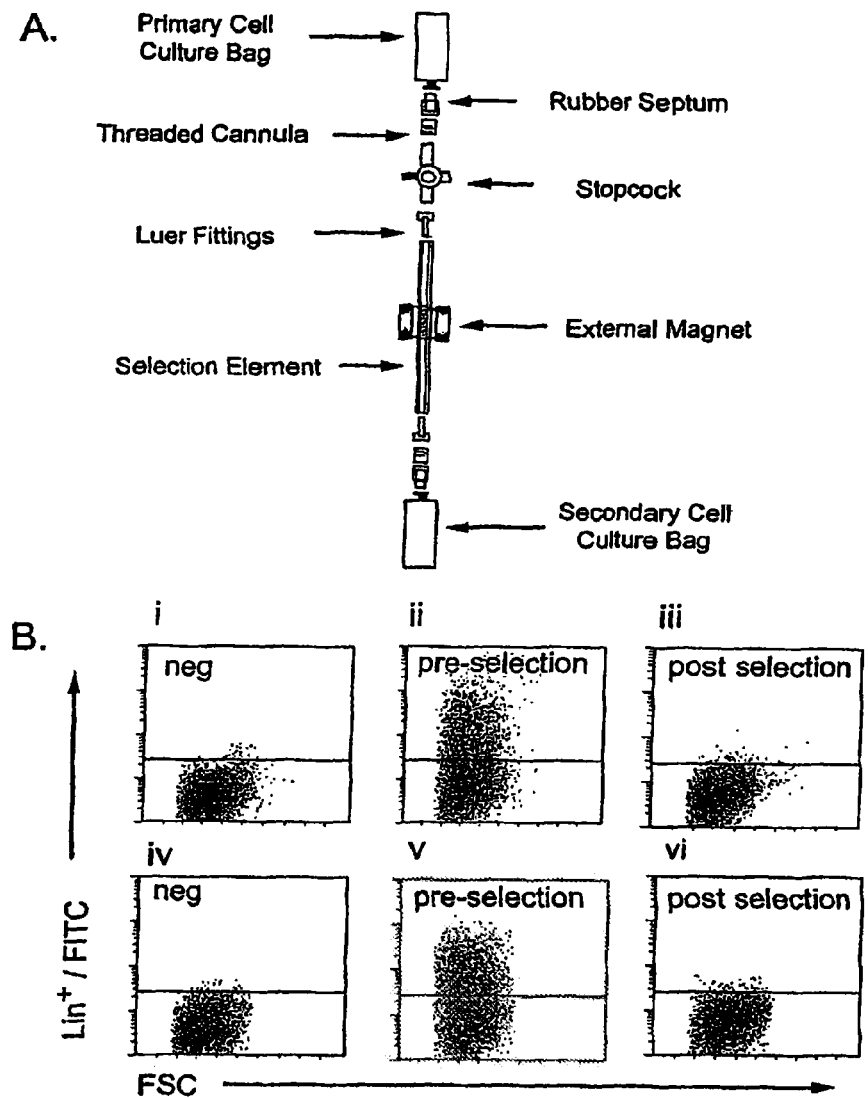

Figure 4.1: (A) A schematic of the closed-system bioprocess. The bioprocess consists of two cell culture bags (3 or 7 ml) which are joined through a subpopulation selection element. The subpopulation selection element is used to remove contaminating lin$^+$ cell from culture. (B) Validation of the subpopulation selection element. Representative flow cytometric plots showing the amount of lin$^+$ cells present pre- (B$ii$) and post-selection. (B$iii$). A negative control is also shown that was not labeled with the lin$^+$ antibody cocktail (B$i$). Comparisons were made to the commercially available StemSep™ column (B $iv$, $ii$, $iii$). The plots demonstrate the successful removal of lin$^+$ cells when cultured cells are passed through the subpopulation selection element.

Figure 11.
A.
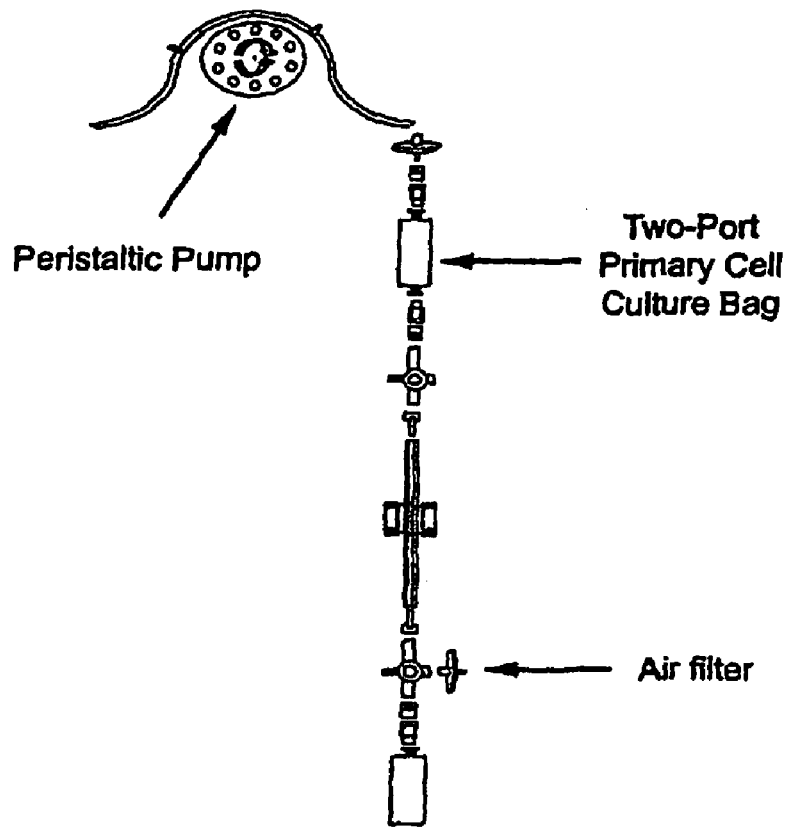
B.
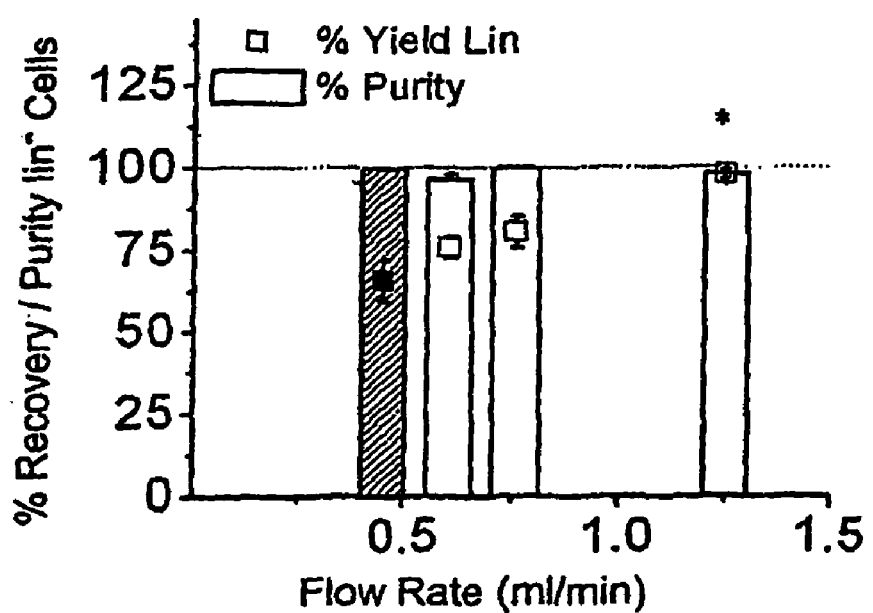

Figure 16.
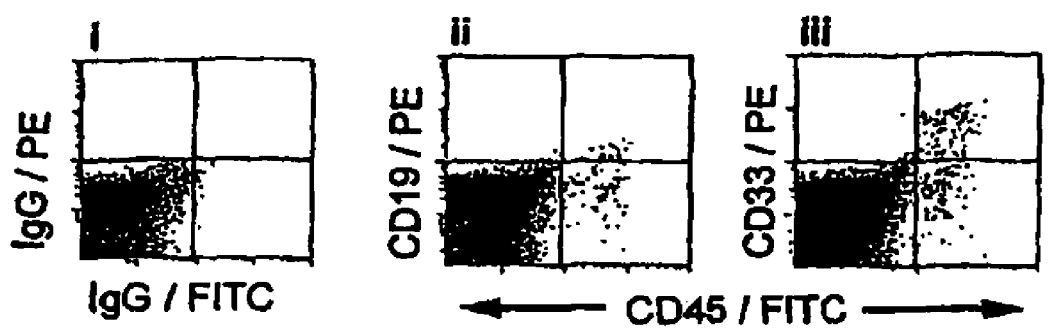
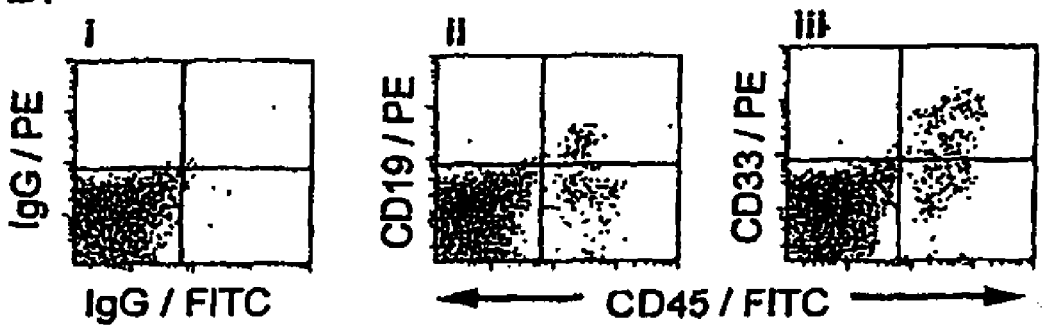

APPARATUS AND METHODS FOR AMPLIFICATION OF BLOOD STEM CELL NUMBERS

RELATED APPLICATIONS

The present application is a national stage application of International Patent Application serial number PCT/IB04/01724, filed on May 3, 2004; which claims the benefit of U.S. Provisional Application No. 60/467,589, filed on May 2, 2003; U.S. Provisional Application No. 60/554,833, filed on Mar. 19, 2004; and U.S. Provisional Application No. 60/557,426, filed on Mar. 29, 2004. The entire contents of each of these applications are hereby incorporated by reference in their entireties.

FIELD OF THE INVENTION

The present invention relates to an apparatus and methods for expanding stem or progenitor cells in a controllable bioprocess system, providing for expansion of the stem or progenitor cells, controlling endogenous factor production, and providing cell populations (mixtures of stem, progenitor, and mature cells) that are useful for transplantation (hematopoietic rescue) and other therapeutic treatments.

BACKGROUND OF INVENTION

Hematopoietic stem cells are rare cells that have been identified in fetal bone marrow, umbilical cord blood, adult bone marrow, and peripheral blood, which are capable of differentiating into each of the myeloerythroid (red blood cells, granulocytes, monocytes), megakaryocyte (platelets) and lymphoid (T-cells, B-cells, and natural killer cells) lineages. In addition these cells are long-lived, and are capable of producing additional stem cells, a process termed self-renewal. Stem cells initially undergo commitment to lineage restricted progenitor cells, which can be assayed by their ability to form colonies in semisolid media. Progenitor cells are restricted in their ability to undergo multi-lineage differentiation and have lost their ability to self-renew. Progenitor cells eventually differentiate and mature into each of the functional elements of the blood. The lifelong maintenance of mature blood cells results from the proliferative activity of a small number of pluripotent hematopoietic stem cells that have a high, but perhaps limited, capacity for self-renewal. In culture, hematopoietic stem cells rapidly commit to differentiated cell types, which irreversibly predominate in the culture. This property, along with their relative scarcity in blood, presents challenges to the creation of long term, stable cultures of pluripotent hematopoietic stem cells.

SUMMARY OF THE INVENTION

The present invention provides for an apparatus and methods for expanding undifferentiated pluripotent cells of the hematopoietic lineage in culture, whereby the cells proliferate in culture with little to no lineage commitment, and differentiation. The undifferentiated hematopoietic cells generally have the phenotypes of CD34+, CD34+Lin−, CD133+, NOD/SCID repopulating cells, and rapid NOD/SCID repopulating cells.

This bioprocess includes in one aspect, a bioprocess device having a first cell culture chamber, a second cell culture chamber, and a conduit in regulatable fluid communication with the first chamber and the second chamber. In one embodiment, the interior surfaces of the first cell culture chamber, the second cell culture chamber and the conduit are substantially closed to the environment. In another embodiment, one or more of the interior surfaces of the first cell culture chamber, the second cell culture chamber and the conduit are substantially open to the environment. The device includes embodiments wherein the first cell culture chamber or the second cell culture chamber is semipermeable to oxygen gas and carbon dioxide gas, but substantially impermeable to liquids. In other embodiments, at least one of the first cell culture chamber or the second cell culture chamber is adapted to a pump device. In certain embodiments, the bioprocess system is modular, and the first chamber, the second chamber, or the conduit are detachable.

In one aspect, the conduit has a selection element. The selection element is used to segregate differentiated cells from undifferentiated cells, and in one embodiment has affinity for one or more antigens expressed by differentiated hematopoietic cells, for example but not limited to antigens selected from the group consisting of: lin+antigens, CD2, CD3, CD4, CD8, CD13, CD14, CD16, CD19, CD24, CD38, CD45, CD56, CD66b and glycophorin A. In one embodiment, the conduit further includes a magnet or a magnetizable element, to facilitate segregation of the cell subpopulations.

Also provided are methods of cell culture. A sample of hematopoietic cells is obtained, further including a subset of undifferentiated hematopoietic cells. The sample of hematopoietic cells are cultured in culture media and under conditions appropriate to cause proliferation of the undifferentiated hematopoietic cells. The undifferentiated hematopoietic cells are segregated from differentiated hematopoietic cells or growth factors, and the segregated undifferentiated hematopoietic cells are further cultured thereby causing proliferation of the segregated undifferentiated hematopoietic cells. This method can be carried out in either closed or open culture conditions. In various embodiments, the growth factors are segregated from the undifferentiated hematopoietic cells, by exchange of the culture media, by dilution, or by perfusion of the culture. In other embodiments, the differentiated hematopoietic cells are segregated from the undifferentiated hematopoietic cells by affinity separation, immunoaffinity separation, and the immunoaffinity separation is performed using a selection element having an antibody or fragment thereof, for example but not limited to anti-CD2, anti-CD3, anti-CD4, anti-CD8, anti-CD13, anti-CD14, anti-CD16, anti-CD19, anti-CD24, anti-CD38, anti-CD45, anti-CD56, anti-CD66b, and an anti-glycophorin A antibody.

The invention also provides methods of preserving cells. A sample of hematopoietic cells is obtained further including a subset of undifferentiated hematopoietic cells. The cells hematopoietic cells are cultured in culture media and under conditions appropriate to cause proliferation of the subpopulation of undifferentiated hematopoietic cells; the undifferentiated hematopoietic cells are segregated from the differentiated hematopoietic cells and undesired growth factors; and the cells are cultured further, thereby causing proliferation of the segregated undifferentiated hematopoietic cells. The segregated undifferentiated hematopoietic cells are then frozen, e.g., in DMSO, in glycerin, or another suitable cryopreservative. These methods can be performed in closed system and open system embodiments. In various other embodiments, the growth factors are segregated from the undifferentiated hematopoietic cells, by exchange of the culture media, by dilution, or by perfusion of the culture. In other embodiments, the differentiated hematopoietic cells are segregated from the undifferentiated hematopoietic cells by affinity separation, immunoaffinity separation, and the immunoaffinity separation is performed using a selection element having an antibody or fragment thereof, for example but not limited to anti-CD2, anti-CD3, anti-CD4, anti-CD8, anti-CD13, anti-CD14, anti-CD16, anti-CD19, anti-CD24, anti-CD38, anti-CD45, anti-CD56, anti-CD66b, and an anti-glycophorin A antibody.

In another aspect, the invention includes methods of treating a mammal. A mammal is first identified, having a disorder characterized by an insufficient number of hematopoietic cells; a sample of hematopoietic cells is obtained, e.g., from a donor for an allograft transplant, or from the mammal for an autologous transplant, the sample further including a subset of undifferentiated hematopoietic cells; the sample of hematopoietic cells is cultured in culture media and under conditions appropriate to cause proliferation of the undifferentiated hematopoietic cells; the undifferentiated hematopoietic cells are segregated from differentiated hematopoietic cells or growth factors; and the segregated undifferentiated hematopoietic cells are cultured further, thereby causing further proliferation of the segregated undifferentiated hematopoietic cells. The mammal is providing with a suitable quantity of the cultured undifferentiated hematopoietic cells, and the cultured undifferentiated hematopoietic cells increase the number of hematopoietic cells in the mammal, thereby treating the disorder. Embodiments of the invention include open and closed systems. Disorders suitable for treatment include, for example but not limited to a cytopenia or an anemia such as those induced by cancer treatments, or a genetic defect resulting in aberrant levels of blood cells, or cancer, for example a graft versus tumor approach. In one embodiment, cultures of undifferentiated hematopoietic cells with long-term repopulating potential are expanded at least a four-fold prior to transplantation in the mammal. In one embodiment, the invention includes a method for providing a cell population of undifferentiated human hematopoietic cells; wherein the number of undifferentiated human hematopoietic cells increases by at least 20-fold to form the cell population.

The invention also includes in one aspect, a method of providing a therapeutic protein to a mammal. A mammal in need of a therapeutic protein is identified; a sample of hematopoietic cells is obtained further including a subset of undifferentiated hematopoietic cells; a gene encoding the therapeutic protein is introduced into at least one undifferentiated hematopoietic cell; the undifferentiated hematopoietic cell having the gene is cultured in culture media and under conditions appropriate to cause proliferation of the undifferentiated hematopoietic cell; the undifferentiated hematopoietic cells having the gene are segregated from differentiated hematopoietic cells or growth factors; and the segregated undifferentiated hematopoietic cells having the gene are cultured thereby causing further proliferation of the hematopoietic cells having the gene; and a suitable quantity of the cultured undifferentiated hematopoietic cells having the gene encoding the therapeutic protein, are provided to the mammal as a transplant. The cultured undifferentiated hematopoietic cells having the gene proliferate in the mammal, and express the therapeutic protein in the mammal. In one embodiment, the mammal does not demonstrate a pathological immune response to the transplant after transplantation. In another embodiment, mammal does not demonstrate a pathological immune response to the transgene, or its expression products.

In another aspect, the invention provides a method of providing blood to a mammal. A mammal is identified having an insufficient number of hematopoietic cells; a sample of hematopoietic cells is obtained further comprising a subset of undifferentiated hematopoietic cells; the sample of hematopoietic cells is cultured in culture media and under conditions appropriate to cause proliferation of the undifferentiated hematopoietic cells; the undifferentiated hematopoietic cells are segregated from differentiated hematopoietic cells or growth factors; the segregated undifferentiated hematopoietic cells are cultured further thereby causing proliferation of the segregated undifferentiated hematopoietic cells; and the mammal is provided with a suitable quantity of the cultured undifferentiated hematopoietic cells as a transplant, wherein the cultured undifferentiated hematopoietic cells increase the number of hematopoietic cells in the mammal following the transplant. In one embodiment, cultures of undifferentiated hematopoietic cells with long-term repopulating potential are expanded at least a four-fold prior to transplantation in the mammal. In another embodiment, the invention includes a method for providing a cell population of undifferentiated human hematopoietic cells; wherein the number of undifferentiated human hematopoietic cells increases by at least 20-fold to form the cell population. Culture of cells is performed using either closed systems or open systems. In various embodiments, the undifferentiated hematopoietic stem cells do not cause graft versus host disease in the mammal following transplantation The invention also provides in various aspects, method of controlling cell proliferation. Levels of one or more growth factors in a cell culture having a subpopulation of undifferentiated hematopoietic cells, are reduced, wherein reduction of the growth factor levels allows the undifferentiated hematopoietic cells to expand in number in the culture without substantial lineage commitment of the cells. The growth factors reduced are, for example but not limited to hematopoietins, TGF-beta or MIP-1-alpha. In various embodiments, growth factor levels are reduced by subpopulation segregation, or by media exchange or media dilution, or by perfusion of the culture. Cell cultures may be closed systems or open systems.

In yet another aspect the invention provides a method of banking blood for a mammal. A sample of hematopoietic cells further comprising a subset of undifferentiated hematopoietic cells is obtained from a mammal; the sample of hematopoietic cells are cultured in culture media and under conditions appropriate to cause proliferation of the undifferentiated hematopoietic cells; the undifferentiated hematopoietic cells are segregated from differentiated hematopoietic cells or growth factors; the segregated undifferentiated hematopoietic cells are cultured further thereby causing further proliferation of the segregated undifferentiated hematopoietic cells; and the mammal is provided with a transplant, including a suitable quantity of the cultured undifferentiated hematopoietic cells, wherein the cultured undifferentiated hematopoietic cells increase the number of hematopoietic cells in the mammal following the transplant. Culture of cells is performed using either closed systems or open systems. In certain embodiments, the invention includes commercial processes for collecting, expanding, and banking for a patient, a sample of cultured undifferentiated hematopoietic cells suitable for transplant into the patient. The sample is provided by a donor and used in an allograft, or the patient provides the initial sample, and the cultured undifferentiated hematopoietic cells are used in an autologous transplant.

In various other aspects, the invention provides for a transplant kit. The kit includes a population of undifferentiated hematopoietic cells, that have been expanded at least four-fold in culture, and are suitable for transplant into a mammal, particularly a human. Cells provided in the kit are cultured in either closed systems or open systems. Also included in the kit are instructions for using the cells in a transplant procedure.

Various other embodiments will be apparent in view of the teaching provided herein, and are included in the scope of the invention.

BRIEF DESCRIPTION OF THE DRAWINGS

FIGS. 2A-D show graphical representations comparing the kinetic growth of total cells (A), CD34+ cells (B), CD34+CD38− cells (C), and CFCs (D) using either traditional culture dishes or using the present invention.

FIG. 5A is a graphical representation of ELISA analysis showing changes in TGF-beta1 secretion rates in response to cell selection and enrichment. FIG. 5B depicts RT-PCR analysis showing that column isolated and FACS sorted lin+ cells express TGF-beta1. Beta-actin was used as a control.

FIG. 6A is a graphical representation of ELISA analysis showing changes in MIP-1 alpha secretion rates in response to media exchange. FIG. 6B depicts semi-quantitative RT-PCR analysis showing that MIP-1 alpha expression is decreased in response to fresh media. Beta-actin was used as a control.

FIG. 7A is a schematic of the closed-system bioprocess. The bioprocess consists of two cell culture bags (3 or 7 ml) that are joined through a conduit having a subpopulation selection element. The subpopulation selection element is used to remove contaminating lin+ cells from culture. FIG. 7B illustrates the effect of the subpopulation selection element. Representative flow cytometric plots showing the amount of lin+ cells present pre- (7Bii) and post-selection (7Biii). A negative control is also shown that was not labeled with the lin+ antibody cocktail (7Bi). Comparisons were made to the commercially available StemSep™ column (7B iv, v, vi). The plots demonstrate the successful removal of lin+cells when such cells are passed through the conduit having the subpopulation selection element.

FIG. 11A shows a bioprocess configuration that allows for flow rate control. A peristaltic pump is used to 'push' cells through the conduit having a subpopulation selection element. FIG. 11B shows the effect of increasing flow rate on the recovery and purity of lin− cells exiting the subpopulation selection element. Subpopulation selection was performed in which cells flowed through the selection element at 0.45±0.03 (gravity induced flow rate; n=4), 0.61±0.04 (n=4), 0.76±0.06 (n=4) and 1.25±0.07 ml/min (n=5). At a flow rate of 1.25±0.07 ml/min, both percent recovery and percent purity of lin− cells were maximized. The gravity induced flow rate comparison is highlighted with a hashed column and a filled square.

FIGS. 16A and 16B show multilineage differentiation of cells engrafted into NOD/SCID mice. Mice that were found to show human cell engraftment (CD45$^+$) were analyzed using flow cytometry for their ability to differentiate into cells of both lymphoid and myeloid lineages. (Aii, Bii) Representative FACS analysis dot plots showing CD19 expression on engrafted cells from mice injected intrafemorally (Aii) or intravenously (Bii). Positive staining indicated that cells were capable of lymphoid differentiation. (Aiii, Biii) CD33 expression on engrafted cells from mice injected intrafemorally (Aiii) or intravenously (Biii) showed that cells were also capable of myeloid differentiation. Corresponding isotype controls are also shown (Ai, Bi).

DETAILED DESCRIPTION

Figure 1:
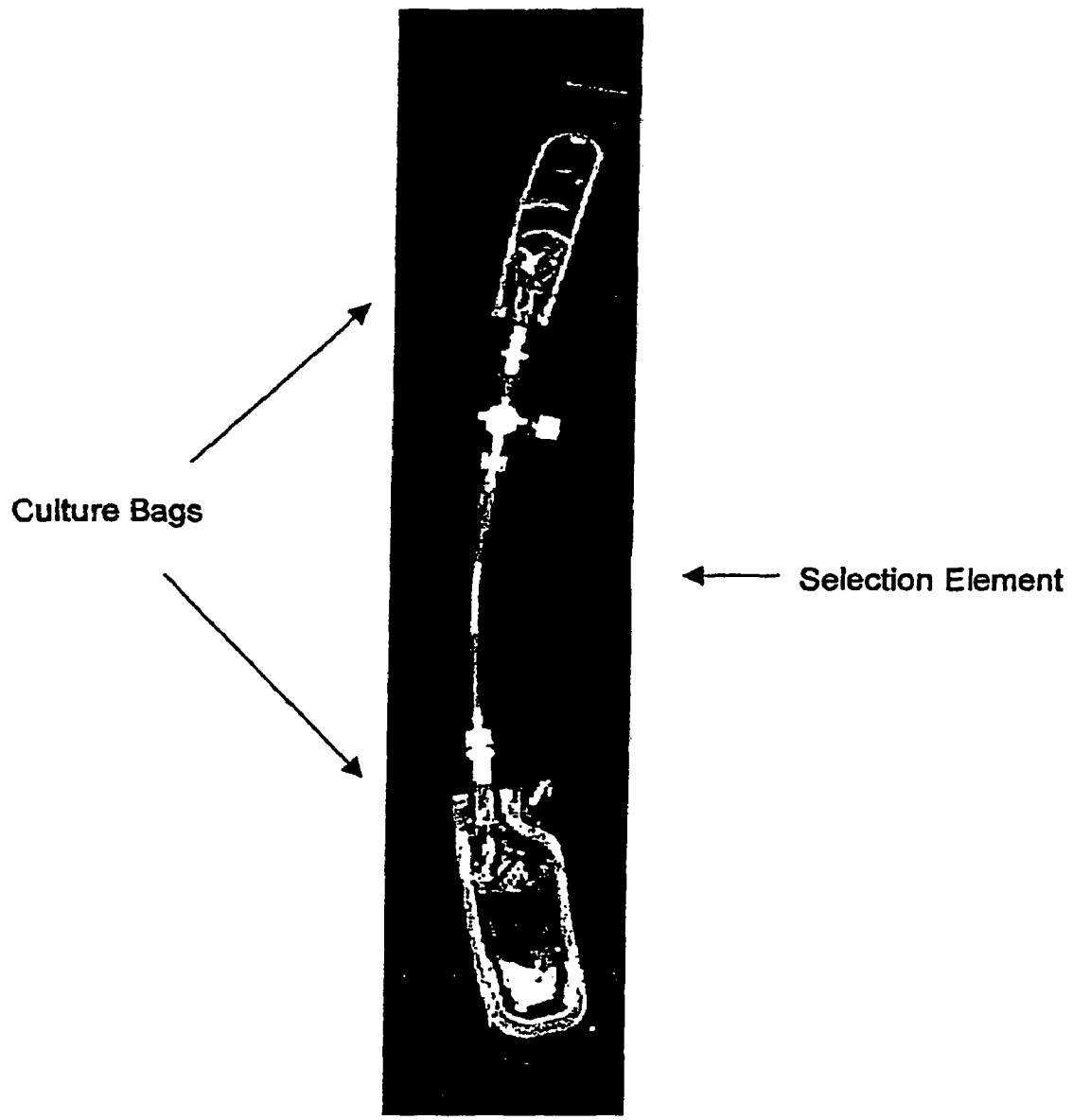
FIG. 1 is a picture of the apparatus used for the bioprocess. The cell culture chamber shown in this illustration employs culture bags semipermeable to gases. The conduit as shown includes an enrichment element, which separates the CD34+ cells from differentiated and committed lin+ hematopoietic cells.

The development of ex vivo culture conditions that facilitate the expansion of hematopoietic stem cells (HSCs) would greatly accelerate the clinical implementation of next generation therapeutics including cell transplantation, gene therapy and tissue engineering. In fact, the last few years have shown an increase in the clinical utility of such cells in transplantation therapies[1-4]. Unfortunately, the establishment of culture conditions capable of consistently and efficiently growing HSCs in vitro has been elusive. Current strategies aimed at expanding HSCs, primarily through growth factor supplementation or stromal cell support, generally result in the expansion of mature progenitors, but are complicated by the loss[5-9] or moderate expansion[7,8,10,12] of more primitive cells following short-term culture. These results are somewhat surprising since, in vivo, HSCs have been shown to have extensive proliferative potential. Experiments demonstrating that long-term engraftment in mice can be achieved by the progeny of a single murine[13-15] or human[16] cell, and that the progeny of a single done can repopulate multiple secondary recipients[17,18] provide evidence of this potential. Furthermore, serial transplant studies in mice, in which input and output numbers of repopulating stem cells were monitored and quantified at each passage, have convincingly shown that repopulating stem cells are capable of sustained in vivo expansion where theoretical 150-8400 fold expansions have been calculated[19,20]. Therefore, it is apparent that simple media supplementation is not sufficient to overcome the growth inhibitory effects seen in most in vitro systems.

Immunophenotyping is a method that can be used to characterize hematopoietic cells based on the expression of cell surface antigens. These markers are expressed on distinct sub-populations of cells and in combination with systematic functional analysis of cells expressing particular cell surface antigens has led to their categorization based on lineage relationships.

As used herein, the terms "undifferentiated hematopoietic cell", "undifferentiated cell", "hematopoietic stem cell (HSC)", and "primitive cell" are used interchangeably to describe a pluripotential hematopoietic stem cell that is capable of long term in vivo expansion and repopulation when transplanted into a mammal. It has been established that the most primitive cell types express the cell surface antigen CD34, which is a transmembrane glycophosphoprotein thought to play an important role in stem and progenitor cell adhesion in BM[72]. Cell populations expressing CD34 and lacking the CD38 antigen (i.e. CD34$^+$CD38$^-$ cells) have been shown to display primitive cell potentials. For example, the majority of SRCs can be found in the CD34$^+$CD38$^-$ cell fractions and not in the CD34$^+$CD38$^+$ populations, which are thought to contain more differentiated cell types[7]. The CD34$^+$CD38$^-$ phenotype has also been associated with an enrichment of cells having LTC-IC characteristics[73]. The existence of murine and human CD34$^-$HSCs that are capable of long-term multilineage repopulation illustrates that the CD34 antigen may itself be regulated independently of HSC potential and that CD34 expression itself is not a requisite HSC marker[14,74-77]. Primitive cells have also been identified based on the expression of Thy-1, a T-cell related marker[78]. Thy-1 expression allows for the recovery of LTC-ICs from UCB, BM and human fetal liver mononuclear cells (MNCs)[79] and accounts for all repopulating cells (Thy-1.1lo) present in mouse BM[80]. Another marker, CD133 (AC133), a transmembrane receptor glycoprotein has also been shown to coincide with the enrichment of early hematopoietic progenitors[81]. CD34$^+$CD133$^+$ cell fractions isolated from UCB are highly enriched in primitive progenitors[82] and SRCs that additionally have the capacity to engraft secondary recipients[83,84]. Recently, vascular growth factor receptor 2 (KDR) has been implicated as a marker for primitive cell types. Studies have shown that the isolation of BM derived CD34$^+$KDR$^+$ results in an enrichment of human LTC-ICs and SRCs[85].

The absence of specific antigens can also be used to characterize and isolate primitive hematopoietic stem cell populations. For example, human CD34$^+$ cells lacking HLA-DR[86] or CD45RA/CD71[87] identify primitive multipotential hematopoietic cells capable of self-renewal and differentiation into multiple hematopoietic lineages. Additionally, isolating cells that lack markers associated with mature myeloid and lymphoid cells represents a method of enriching for primitive cell types.

As used herein, the term "differentiated hematopoietic cell", "differentiated cell", or "progenitor cell" refers to a lineage committed hematopoietic cell. These cells typically express one or more of the antigens CD2, CD3, CD14, CD16, CD19, CD24, CD56, CD66b, and glycophorin A, and are termed lineage markers (lin$^+$). The detection of lin$^+$ antigens indicates the loss of pluripotential properties and that the cell has become differentiated, or lineage committed. Accordingly, these lin$^+$ antigens also provide the appropriate antigens for targeted separation of differentiated cells as described herein, and antibodies to these antigens are widely available for immunoseparation procedures.

As described, the majority of culture conditions investigated to date result in the dominance of differentiated cell types and the concomitant decrease in the frequency and numbers of primitive cells, eventually resulting in culture extinction. This undesired end result is a consequence of several competing factors that can influence culture dynamics. One such parameter is the effect of the endogenous secretion of regulatory molecules, which can be stimulatory or inhibitory to HSC proliferation, by different subpopulations of hematopoietic cells in culture. Using gene expression and protein secretion analysis, a variety of factors known to inhibit HSC expansion were shown to be expressed and secreted by both progenitor and mature cell types[23-28]. For example, monocytes are known to secrete transforming growth factor (TGF)-β1 and macrophage inflammatory protein (MIP)-1α[21,28]. Neutrophils have been associated with the secretion of TGF-β1, MIP-1α and tumor necrosis factor (TNF)-α[21,25] while megakaryocytes secrete interleukin (IL)-3[23]. Similar findings have been documented for erythroid and megakaryocytic progenitors which have been shown to secrete TGF-β1[27]. Furthermore, research has shown that a number of these secreted factors can stimulate the secondary secretion of inhibitory factors by other cell types. For example, the production of IL-12, TNF-α, IL-1, or IL-10 by monocytes can stimulate lymphocytes to produce MIP-1α[29,30]. These inhibitory factors are known to prevent HSC expansion in vitro by causing them to remain quiescent, undergo apoptosis, and/or differentiate into mature cell types[31-35].

This phenomenon is exacerbated by the fact that cytokine receptors are not specific to HSCs but instead can also be found on cells at different stages of blood development. It has been shown that c-kit, flk2/flt3, c-mpl, IL-6R and GM-CSFR (the receptors for SCF, FL, TPO, IL-6 and GM-CSF respectively), can be differentially expressed not only on cells from the stem cell compartment but also on progenitor and mature cell populations[36-43]. The presence of these receptors throughout the hematopoietic hierarchy implies that the actions of supplemented cytokines are not specific to HSCs but also target more differentiated cells. For example, cytokines have been shown to stimulate the terminal differentiation and proliferation of megakaryocyte[44,45], granulocyte[46] and macrophage[47] progenitors. Because of the cellular heterogeneity of HSC expansion cultures, cytokine supplementation would stimulate the simultaneous proliferation and/or differentiation of stem cells (and progenitor cells) which would ultimately result in the formation of large numbers of progenitor and terminally differentiated mature cell populations. In this context, these generated cell populations may then prevent HSC expansion in vitro through the secretion of inhibitory factors.

Further evidence showing that differentiated cells may inhibit stem cell growth comes from mouse transplant studies where it has been shown that the in vivo expansion potential of mouse repopulating stem cells can actually be limited by the transplantation of increased numbers of stem cells[19,20]. These reports suggested that the recovery and production of mature blood cells in recipient mice, which arise from the injected repopulating cells, may be responsible for activating inhibitory mechanisms which ultimately limit stem cell proliferation. Accordingly, undifferentiated cells are segregated from these growth factors in culture, which is accomplished by for example but not limited to, media dilution, media exchange, perfusion, and the like, with the object being to reduce local concentrations of growth factors in the culture media.

A demonstration that endogenously secreted factors can negatively influence culture output, comes from studies in which blocking antibodies or agonists (i.e. oligonucleotides or competitive receptor blockers) specifically directed against individual inhibitory factors have been successful in reversing or preventing the effects of known inhibitors such as TGF-β1, MIP-1α, (MCP)-1 and SDF-1 in both in vitro and in vivo models 48-52. Unfortunately, the use of such blocking schemes has not propagated into a higher expansion of repopulating HSCs, perhaps because multiple secreted factors are responsible for inhibiting this population[31,31,48-55]

One model for stem cell expansion involves a negative feedback control mechanism whereby differentiated blood cells, generated in cytokine supplemented cultures, produce soluble factors that, directly or indirectly, prevent HSC expansion. This mechanism implies that the removal of these cells or the endogenous factors generated by these cells would remove the block to HSC expansion by shifting the balance of signals presented to the stem cells (i.e. from supplemented cytokines and secreted cytokines) from those preventing expansion to those favoring expansion. The removal of these cells may also provide a mechanism to enrich for cells that may secrete stimulatory factors. Usable methods that control and modulate the endogenous production of stimulatory and inhibitory factors thus overcome limitations of current HSC expansion systems. The invention disclosed herein describes an apparatus and processes for expanding HSCs ex vivo in part by controlling the global effects of endogenously produced inhibitory and stimulatory factors.

The removal of specific target cells from culture, coupled with media exchange, results in the concomitant decrease in the endogenous production and overall concentration of inhibitory factors present in culture, which, in turn, results in greater expansion of the HSC population[56].

The HSCs generated as described herein can be used for a variety of clinical applications. For example, the expanded HSCs can be transplanted for amelioration of cytopenia and anemia induced by radiotherapy or chemotherapy using anticancer drugs, in order to enhance or accelerate immune and hematopoietic recovery following intensive treatment. Alternatively, the invention can be used for prevention and treatment of infectious diseases associated with lymphopenia, such as the CD4+ T cell depletion seen with chronic HIV infection. The HSCs can be cultured with differentiating factors to produce specific blood cell types. For example, HSCs produced using this invention can be induced to differentiate into cells of a desired population and function using known biological agents. In this manner, the invention can generate "designer transplants" with a plurality of functions established to provide the greatest patient care. The HSCs can also be used in gene therapy, to express a transgene in a recipient subject, taking advantage of their reduced immunogenicity and pluripotential properties.

The present invention provides for expanding stem or progenitor cells, particularly of the hematopoietic lineage. The process generally includes obtaining hematopoietic cells that are enriched for hematopoietic stem and progenitor cells; for example lin– cells, and introducing them into a suitable growth medium. The cells are maintained in culture and allowed to proliferate. Differentiated cells and endogenous growth factors are removed, either continuously during culture or intermittently during the culture process, for example; through performing media exchange on the cells remaining in culture, and by targeted separation and removal of differentiated cells. The remaining undifferentiated stem cells are cultured and allowed to proliferate further. Multiple cycles of culture and selection/media exchange are performed to expand the cells. Alternatively, differentiated cells in various phases of lineage commitment can be selected and propagated further in accordance with the invention. Likewise, one or more hematopoietins can be added to the culture to force differentiation or lineage commitment. It is preferred that cell expansion and selection be performed in a completely controllable, environmentally closed-system, in accordance with FDA and other regulations governing the handling and processing of blood products, and to maintain sterility. These methods and a representative apparatus for performing this bioprocess, are discussed in detail below.

The bioprocess disclosed herein can be practiced as an open system or as a closed system as is illustrated in the Examples. Closed systems are generally sealed from the environment, and provide a more regulatable sterile microenvironment for the culture. Additional benefits to dosed systems include increased safety for researchers and medical professionals in the handling of biological fluids. Current FDA and other administrative guidelines require dosed systems for the handling and processing of blood cells and products designed to be used in humans, and are accordingly preferred. However, open systems exist for the expansion of hematopoietic stem cells, such as those disclosed herein, and for example U.S. Pat. Nos. 5,674,750 and 5,925,567, (each incorporated herein by reference in their entirety) and other known systems can be modified in accordance with the teachings provided herein to produce a suitable open system bioprocess.

The invention consists of one or more cell culture chambers, capable of receiving and containing a sample of cells. The cell culture chambers may be substantially rigid, for example, as in the case of a cell culture flask or dish, or may be semi-rigid, for example, as in the case of a cell culture bag. There are many types and kinds of cell culture containers (chambers) that are commercially available, such as those produced by Corning Costar. Suitable materials are ones that can withstand a variety of sterilization techniques including autoclaving and gamma irradiation and, for those components which directly contact cells, should also be biologically inert. Selection of an appropriate cell culture chamber is made in view of these and such other factors as the volume desired, transparency, gas diffusion, open or closed design, and the particular selection of the type and kind of chamber would be apparent to one of skill in the art in view of the teachings provided. A currently preferred embodiment employs cell culture bags that are semi-permeable to oxygen gas and carbon dioxide gas, but substantially impermeable to water vapor and liquids such as cell culture media, thus ensuring no or little loss of growth medium during culture. Fluorinated ethylene polymers exemplify material suitable for this purpose. Other materials that are not gas permeable but meet the appropriate criteria include polypropylene, stainless steel and other medical grade materials, particularly polymers.

The cell culture chambers may include one or more ports, replaceable caps or covers, self-sealing septa such as rubber stoppers, valves, or similar means that allow the user to add or remove materials from the chamber without substantial exposure of the interior of the bioprocess to the external environment. For example, these mechanisms permit the cells, media and other components, such as antibodies and growth factors, to be introduced into the chamber, and permit removal of media, cells, endogenous soluble growth factors and the like, from the chamber, while maintaining an environmentally closed system. Vents, regulators or other ports for attaching external gas (e.g., oxygen or air) or liquid (e.g., culture media) sources, or for attaching pumps or pressure devices, may be provided.

In a currently preferred embodiment, a first cell culture chamber is used for initial culture and expansion of cells. Following selection, a second cell culture chamber is used for subsequent expansion of the desired cells. To maintain the closed system, this embodiment includes a conduit, which provides a means for achieving fluid communication between the first cell culture chamber and the second cell culture chamber. Fluid transfer between the cell culture chambers, through the conduit, can be regulated by flow regulators, ports or valves, pumps or similar devices, as described above.

The conduit may include a selection element, which may be positioned within the lumen of the conduit, or which may be external. A selection element may take the form of for example an enrichment matrix, such as microbeads contained inside the conduit, which have a specific affinity for a ligand, or have a specific charge, for example Affi-Gel beads with covalently bound anti-CD34 monoclonal antibody, or the like.

The selection element targets and selects cells having particular phenotypes, for example, those characteristic of differentiated cells. One role of the selection element is to immobilize the differentiated cells to the selection surface, thereby reducing the number of differentiated cells in culture, and segregating them from undifferentiated cells. For example a selection element may include beads having antibodies immunospecific to pan-differentiated hematopoietic cells, such as those manufactured by StemCell Technologies. Antibodies provide an excellent means for affinity separation of differentiated cells, because many antigenic markers for differentiated cells exist, and antibodies to these antigens are commercially available. However, antibodies provide one means for targeted immunoseparation, and F(ab) or F(ab)$_2$ fragments, Fv fragments, and bispecific antibodies (or fragments) can also be used, and the descriptions herein of cellular segregation with whole immunoglobulins is intended to be exemplary and non-limiting. Cells can be separated by numerous other methods, such as FACS, lectin affinity, and other methods know in the art.

The selection element targets and selects cells having antigenic markers characteristic of undifferentiated hematopoietic stem cells, providing for their removal from the heterogeneous culture. For example, a CD34$^+$ expressing cell may be contacted with, and immobilized to an enrichment element having CD34 affinity. In either embodiment, the designations positive selection and negative selection will apply with respect to the particular cells targeted, the selection element used, and whether the selection element targets differentiated cells or undifferentiated cells, e.g., if the target cell is CD34$^+$ and the selection element has affinity for CD34, then isolation of CD34$^+$ cells is an example of positive selection; but if the target cell is CD34$^+$ and the selection element has affinity for pan-differentiated hematopoietic cells, isolation of CD34+ cells by binding to the matrix and removal from the culture of differentiated cells provides an example of negative selection.

Segregation of differentiated cells from undifferentiated cells can be accomplished by many methods. Positive or negative selection methods are preferred. Selection can be accomplished in a particular location within the apparatus, such as within the conduit using a selection element, and cells can be segregated in one step, such as during passage through the conduit. Alternatively, segregation may take several steps. For example, bispecific antibodies are added to the cell culture along with a magnetic colloid, the bispecific antibodies having affinity for the magnetic colloid and for a lin+ antigen. This process effectively attaches a magnetic colloid to a lin+ cell. The magnetically labeled cells are passed through the conduit, which is itself placed in a magnetic field. Other modifications are described herein and will be apparent to those of skill in the art in view of the teachings provided. The segregation of undifferentiated cells and differentiated cells is thus believed to be routine.

The bioprocess described herein may employ a continuous process of growth and selection, or a discontinuous process of growth an selection. In a continuous process, cells are cultured and selection of target cells (either positive selection or negative selection) is effectuated without removing the cells from media or otherwise interrupting the cell culture process. In a discontinuous process, culture and selection proceed in a stepwise manner. Where a modular closed system apparatus is used, it may be more convenient to employ a discontinuous bioprocess since the chambers can be removed from the conduit and placed in an incubator without having to keep the apparatus assembled.

Under most conditions, ex vivo HSC cultures will attempt to recapitulate hematopoiesis and as such will eventually form a heterogeneous population of cells containing components of the hematopoietic system. Insight into the overall developmental potential and primitiveness of these cells would provide information about the ability of a specific culture methodology to expand primitive cell types. Developing this knowledge requires robust and quantitative monitoring of cells that are at different stages of differentiation. Various assays have been developed which identify these cells based on distinct functional properties. Cell function can be queried in vitro using established retrospective assays that detect the presence of committed and multipotent progenitor cells based on the formation of morphologically distinguishable colonies. Colony forming cells (CFCs) are progenitor cells that can be detected by the formation of erythroid, myeloid or mixed (i.e. both erythroid and myeloid) cell containing colonies after 2-3 weeks of culture in semi-solid media (methycellulose). Long-term culture-initiating cells (LTC-ICs) are more primitive than CFCs and can be enumerated by their ability to give rise to CFCs after greater than 5-weeks of culture with stromal cells[57,58]. The stromal cell elements, which are composed of mesenchymal cells including fibroblasts, endothelial cells, adipocytes and osteogenic cells, produce a variety of soluble factors that support the long-term proliferation and maintenance of LTC-ICs. The sensitivity of this assay can be increased through the use of genetically engineered murine fibroblast (M2-10B4) cell lines that secrete factors known to enhance the detection and maintenance of LTC-ICs[59,60].

In vivo functional assays offer the best indication of the developmental potential of a hematopoietic cell population. This is because they directly test the potential for a stem cell population to contribute to the development or re-development of a particular organ, tissue or system following intravenous injection. For example, murine HSCs have been identified based on their ability to reconstitute hematopoiesis after transplantation into an immunocompromised and hematologically compromised host. Till and McCulloch[61] first reported the existence of such a cell type when they injected syngeneic BM cells into irradiated mouse recipients and observed the formation of multi-lineage colonies in the spleen. Interestingly, these colonies contained cells that could form additional colonies upon transplantation into secondary hosts.

While many animal models have been developed to detect the presence of human HSCs[62-65], the most widely-used involves non-obese diabetic/severe combined immunodeficient (NOD/SCID) mice[66,67]. Cells capable of engrafting these recipients have been termed NOD/SCID-repopulating cells (SRCs)[68] and are considered to be human HSCs that home to and engraft the murine BM, where they subsequently proliferate and differentiate into multiple blood cell lineages[69,70]. This assay has been successfully used with standard limiting dilution analysis (LDA) as a means to quantify HSC content in a given cell sample[71].

The present invention provides an apparatus and methods for the expansion of hematopoietic stem and progenitor cells used, for example in a therapeutic transplant to repopulate the blood of a mammal. Since these cells are relatively rare, a starting cell population is first obtained using methods known in the art. Blood, such as mobilized peripheral blood (PB) and bone marrow (BM) are suitable sources, but umbilical cord blood (UCB) provides an enriched source of these undifferentiated cells. Further enrichment of the hematopoietic stem or progenitor cell content from these sources can also be performed prior to culture, for example by purifying mononuclear cell (MNC) fractions. This can be accomplished by using, e.g., centrifugation such as through a Ficoll gradient. Isolation of more enriched populations of hematopoietic stem and progenitor cells can be accomplished using fluorescence-activated cell sorting, immobilization to glass wool, column separation or bead separation techniques, or other known methods of enrichment. Many suitable types are known in the art.

In accordance with the present invention, HSCs in culture are separated from inhibitory hematopoietins (through subpopulation selection and/or media exchange procedures) to prevent their differentiation and commitment to particular lineages. Hematopoietins are a generic name given to hematopoietic growth factors (HGF) or hematopoietic cytokines, which act on cells of the hematopoietic system. These factors are active at all stages of development, and accordingly these hematopoietins will be removed from the bioprocess to prevent HSC differentiation.

Hematopoietic growth factors are produced by many different cell types including those not belonging to the hematopoietic system. These factors are either secreted or they exist in membrane-bound or matrix-associated forms. They may have different modes of action also, such as autocrine, paracrine, or juxtacrine growth control. Production of hematopoietic factors is regulated strictly, i.e., they are synthesized by activated cells under certain conditions rather than being produced constitutively all the time. Many observations point to the existence of an ordered hierarchy and a concerted action of factors involved in the development of the hematopoietic system. These factors are required for the maintenance of hematopoietic stem cells, their proliferation, their differentiation into different hematopoietic lineages, and for the maintenance of a stable equilibrium between proliferation and differentiation. These factors allow an organism to shift this equilibrium to one or the other side, as required, for example, under stress conditions. Many of these factors overlap in their biological activities. Teleologically this guarantees a high efficiency and also allows substitution and/or complementation of individual components the functions of which may have been impaired, for example, under pathological conditions. In addition, responses elicited by these factors are usually contextual, i.e. these responses depend on the presence and concentration of other cytokines and/or factors in the environment of the responding cells. The majority of studies aimed at stimulating HSC expansion in vitro focus on the use of exogenous cytokine supplementation strategies. Cytokines interact with HSCs via three classes of transmembrane receptors; 1) those with intrinsic tyrosine kinase activity, 2) those that interact with the gp130 subunit and 3) those that interact with Janus kinases (JAKs)[88,89]. Over the years, the use of phenotypic and functional assays has identified a number of cytokines which have distinct stimulatory effects on primitive hematopoietic cells. These include flk2/flt3 ligand (FL), stem cell factor (SCF), interleukin (IL)-6, IL-6/soluble IL-6-receptor (SIL-6R), IL-11, thrombopoietin (TPO), IL-3, IL-1, IL-12, granulocyte-colony stimulating factor (GCSF) and granulocyte-macrophage-colony stimulating factor (GM-CSF) 90-10. The first reported use of stroma-free cytokine supplemented cultures, which contained IL-1, IL-3, IL-6, GCSF, GM-CSF and SCF, supported a significant expansion (66-fold) of colony forming unit-granulocyte-macrophage (CFU-GM) progenitor cells 102. Accordingly these hematopoietins can be introduced to the bioprocess to modulate differentiation of HSC's, or can be removed.

Some factors, such as those mentioned earlier, negatively regulate processes of hematopoiesis. For example, they may selectively inhibit the proliferation of some types of hematopoietic cells and may even induce cell death. For example, it has been shown that the addition of TGF-β to hematopoietic cell cultures directly inhibits the expansion of repopulating stem cells[103], LTC-ICs[48] and primitive CFCs[104,55] but has no effect on more mature progenitors 105. Similar is the finding that TGF-β preferentially inhibits the growth of CD34$^+$ CD38$^-$ cells whereas more mature CD34$^+$CD38$^+$ cells are poorly affected[106]. The functional effects of TGF-β have been attributed to its ability to prevent cells from progressing through the cell cycle. It has been shown that in the presence of TGF-β primitive cell populations (including CD34$^+$ cells) are unable to transition from either $G_0$ to $G_1$ or $G_1$ to S phase presumably due to the up-regulation of the cyclin dependent kinase (cdk) inhibitors p15, p27 and p21[31,107]. Finally, TGF-β may also elicit some of its actions by down-regulating the expression of receptor types whose signaling is important for the in vitro growth of HSCs including c-kit[108,109], c-mpl[100] and flt3/flk2[107,110]. MIP-1α has been shown to inhibit the proliferation of primitive hematopoietic cells including CFU-GEMM and CFU-GM even in the presence of stimulatory factors[33,111-113]. In vivo administration of MIP-1α into mice (C3H/HeJ and BDF1 strains) significantly decreases the number of primitive progenitor cells in cycle as assayed using the thymidine kill assay (which effectively kills cycling cells)[114] and protects stem and progenitor cells from the cytotoxic effects of hydroxy urea[115]. Interestingly, MIP-1α has little effect, or even stimulatory effects, on more mature progenitors[116] suggesting that MIP-1α may be a pleiotropic factor. IL-3 is another cytokine thought to have inhibitory functions. It is a controversial cytokine because of conflicting reports regarding its ability to stimulate or inhibit HSC expansion. IL-3 has been linked to the growth of primitive cells including LTC-ICs and CFCs, and is often found in cytokine combinations reported to be effective in expansion cultures[117]. Conversely, several studies have indicated that IL-3 can abrogate the expansion and self-renewal of primitive stem cells in a concentration dependent manner[118] and, in both human and murine models, IL-3 has been shown to impair the reconstituting ability of HSCs[35,119]. These observations are somewhat clarified by the recent finding that IL-3 may prevent HSCs from homing to the BM by impairing their chemotactic response to stromal derived factor-1 (SDF-1) through the CXCR4 receptor[120], thereby resulting in the in vivo clearance and destruction of potential engrafting cells in non-hematopoietic tissues. Additionally, the presence of TNF-α in cultures supplemented with stimulatory cytokines including SCF[121] and FL[34,122] can potently inhibit the proliferation of progenitor cells, likely by promoting apoptosis[123] through Fas (a member of the TNF receptor family) signaling[124]. Examples of other inhibitory cytokines include monocyte chemoattractant protein (MCP)-1[52] and SDF-1[125,126]. Those hematopoietins can be introduced into the bioprocess or removed as described.

As a whole the action of many of these factors underscores the problems associated with continuous culture of stem cells, since hematopoietins generally need to be removed to prevent lineage commitment. Alternatively, they may be added to specific cultures to force lineage commitment. In contrast, certain hematopoetins can preserve the naïve and undifferentiated state of CD34+ cells, and their addition to or enrichment in the bioprocess may improve yield. Modulation of hematopoietins in the bioprocess is thus considered within the abilities of one skilled in the art of the teachings provided herein.

Exemplary culture conditions for growing HSCs are given in the Examples, but generally in accordance with the invention, a sample of cells containing a subset of HSCs is first obtained then cultured. The cultured cells are then maintained for a growth period suitable for allowing proliferation to occur, which may include media exchanges to remove soluble growth factors, after which time the HSCs are segregated from the other differentiated cells. The HSCs are then allowed to proliferate again as described. The segregation of differentiated cells can be performed again if necessary. At the end of the culture period the expanded HSCs can be preserved by freezing after addition of, for example glycerin, DMSO or a suitable cryopreservative, or used directly in a therapeutic procedure. It is important to note that the above steps can be performed with the entire bioprocess apparatus assembled or in separate parts in which cell culture is carried out independent of cell segregation.

Clinical uses for HSCs include, for example, the therapeutic treatment of blood cancers treatment of anemia, treatment of hereditary blood disorders, replenishment of blood cells following high dose radiation and chemotherapy in the treatment of cancer, graft-versus-tumor treatment of cancer, treatment of autoimmune disorders, and in gene therapy approaches.

For the therapeutic treatment of blood cancers, including lymphoblastic leukemia, acute myeloblastic leukemia, chronic myelogenous leukemia (CML) Hodgkin's disease, multiple myeloma, and non-Hodgkin's and B-cell lymphomas, a patient's own cancerous hematopoietic cells are first destroyed by high dose radiation and chemotherapy. A matched donor (having similar HLA profiles) provides the source of transplantable HSCs, which are isolated and expanded according to the methods provided herein. The transplant of undifferentiated cells provides for long term repopulation of the blood of the recipient. Non-cancerous blood disorders amenable to treatment by HSC therapy include aplastic and other types of anemia. The transplant of undifferentiated cells provides for long term repopulation of the blood of the recipient. Using UCB, multiple studies have demonstrated that cell dose is an important determinant of patient survival in stem cell transplantation scenarios[127], Wagner et al. (2002) reported that the rate of engraftment is decreased in patients receiving fewer than $1.7 \times 10^5$ CD34+ cells/kg body weight (72% versus 93% in patients who received larger doses)[128]. Likewise, it was found that transplants of $3.7 \times 10^8$ MNC/kg resulted in more rapid engraftment than patients who received only $3.7 \times 10^7$ MNC/kg (i.e. one log less), although patients receiving the lower cell dose also showed good engraftment[127,129]. Based on these results, it was recommended that the minimum cell dose for UCB transplants be $3.7 \times 10^7$ MNC/kg 127. Because typical UCB collections contain an average of approximately $1.4 \times 10^9$ MNC (Cairo, Blood, 1997, 90:4665), it was calculated that an average cord blood sample would be sufficient to transplant a patient weighing a maximum of approximately 37 kg (~81 lbs). Using similar calculations, it was reported that 75% of the greater than 4000-banked samples at the Toronto Umbilical Cord Blood Bank contain only enough cells to be useful for pediatric bone marrow transplantations (i.e. patients weighing ~24 kg or ~53 lbs)[130]. Therefore, in order for these, and other banked samples to be a useful source of HSCs for single or multiple adult transplants, or for multiple tissue regeneration therapies, their HSC content must be increased. The ex vivo expansion of HSCs described herein provides such a provides a solution. The bioprocess can also be used to expand undifferentiated cells from adult sources, for example a donor provides his or her own bone marrow or peripheral blood, thus eliminating immune mismatch in the event of a transplant of these cells back to the donor. Alternatively, the bioprocess can be used to expand pluripotential hematopoietic cells that are allogeneic but not immunogenic, and thus suitable for transplant purposes.

The bioprocess may be used to express a therapeutic protein from the undifferentiated cells, which have been genetically modified ex vivo to incorporate a transgene encoding the therapeutic protein. The hematopoietic cells are obtained, transfected with the transgene, and expanded in culture as described. Differentiated cells are removed from culture, and the undifferentiated cells are assayed for expression of the transgene. Cells positively expressing the transgene are transplanted into a mammal. The low immunogenicity of stem cells makes this cell type well-suited for gene therapy.

Other uses of the invention are contemplated. For example, the bioprocess can be used by commercial and non-profit blood banking organizations, to expand a subpopulation of undifferentiated cells, e.g., lin−, CD133+, CD34+, long-term repopulating NOD/SCID and other undifferentiated cells, that can later be frozen and stored, or used in a transplant procedure. A donor may provide the sample of cells, or a patient about to undergo a medical procedure may provide the source of cells that will be expanded. In the latter case, the cells are a perfect immunological match for the recipient. Commercial methods of storing, processing and providing undifferentiated are thus included within the scope of this invention.

The invention is now described in specific terms by the foregoing examples, which are illustrative only and are intended to be non-limiting and specific embodiments, whereas the full scope of the invention shall be determined solely by the claims.

EXAMPLES

1. Cell Sample Collection and Purification

UCB samples were collected from consenting donors according to the procedures accepted by the ethics board of Mt. Sinai Hospital (Toronto, ON, Canada) and centrifuged over 10% pentastarch (Bristol-Myers Squibb Canada, Montreal, QC, Canada) to obtain the mononuclear cell (MNC) fraction. Lineage depleted (lin−) cells were isolated from the MNC fraction using the StemSep™ system according to the manufacturers protocol (Stem Cell Technologies, Vancouver, BC, Canada). Briefly, MNCs were collected in Hanks Buffered Saline Solution (HBSS; Gibco, Rockville, Md.) containing 2% human serum (HS) at a concentration of $50 \times 10^6$ cells/ml. The selection antibody cocktail was then added at a concentration of 100 μl/ml cell suspension. The antibody cocktail used removes cells expressing CD2, CD3, CD14, CD16, CD19, CD24, CD56, CD66b, and glycophorin A. The cells were then incubated for 15 min at room temperature (RT) after which time a magnetic colloid was added at a concentration of 60 μl/ml cell suspension. The cells were then allowed to incubate an additional 15 min at RT. These steps effectively attach a magnetic particle to target cells (lin+ cells) that are to be removed from the initial MNC sample. The cells were then passed through a magnetic column, containing magnetic beads, to isolate the lin− cell fraction. The magnetic column was placed in an external magnetic field prior to the separation step.

2. Bioprocess Assembly

The bioprocess apparatus was assembled using the following procedure:

Two 3 ml FEP culture bags (VueLife®, American Fluoroseal Corporation, Gaithersburg, Md.) were used as cell culture chambers to culture cells pre- and post-selection. Each bag was fitted with a self-sealing rubber septum (InterLink, American Fluoroseal Corporation) at its inlet port.

An approximately 4-5 inch length of ⅛ inch internal diameter FEP lined Tygon® tubing (Cole-Parmer, Vernon Hills, Ill.) was used as the conduit, and was adapted to house the selection element, in the form of enrichment beads. The beads were held in the tubing by first punching out two 0.12"-0.15" diameter pieces of 80 mesh 430 stainless steel screening (Stem Cell Technologies) and forming them to fit snugly into the inside diameter of the tubing (all done using a machined punch and form). One of the screens was then placed into the tubing (about half-way down) using a small metal plunger. Care was taken to insert the screen so that its flat face was perpendicular to the length of the tubing. The enrichment beads (Stem Cell Technologies) were then placed in the tubing until they filled a length of approximately 1" after which the second screen was inserted into the tubing to hold the beads in place. These beads aid in the magnetic separation of cells as described above. ⅛" male luer fittings (Cole-Parmer) were then placed into each end of the tubing to which were attached two threaded lock cannulas (American Fluoroseal Corporation). The cannula mates with the self-sealing rubber septums for sterile filling, sampling or emptying of culture bags. This selection element is also referred to as the 'enrichment element'.

The enrichment element was then connected between the two culture bags via the mating of the septum and cannula. The entire assembled product in its entirety is now called the "bioprocess apparatus" or "bioprocess". As mentioned above, the bioprocess can be used entirely assembled or in discontinuous sections, thus permitting cell culture to be performed separately from cell segregation. In one modification, the use of the bioprocess as a single assembled product would require that a three-way stopcock (Cole-Parmer) be placed between one of the culture bags and the tubing. The stopcock would facilitate filling of the culture bag with cells and growth medium. In this case, the sterile septum would be attached to the stopcock inlet port.

3. Cell Seeding and Culture in Open System

Lin$^-$ cells were seeded at 1×10$^5$ cells/ml in StemSpan™ media (Stem Cell Technologies) containing Iscove's MDM, 1% BSA, 10 µg/ml rh insulin, 200 µg/ml human transferring, 10$^{-4}$ M 2-mercaptoethanol and 2 mM L-glutamine. The media was supplemented with 100 ng/ml SCF (Amgen, Thousand Oaks, Calif.), 100 ng/ml FL (Amgen) and 50 ng/ml TPO(R&D Systems, Minneapolis, Minn.). Approximately 1.5 ml of the cell suspension was then placed into the wells of a 24-well plate and maintained at 37° C. in a humidified atmosphere of 5% $CO_2$ in air for 8 days. Re-selection after 4-days in culture (i.e. to remove lin$^+$ cells generated during culture) was performed.

4. Cell Seeding and Culture in Bioprocess

Lin$^-$ cells were seeded at 1×10$^5$ cells/ml in StemSpan™ media (Stem Cell Technologies) containing Iscove's MDM, 1% BSA, 10 micrograms/ml rh insulin, 200 micrograms/ml human transferrin, 10$^{-4}$ M 2-mercaptoethanol and 2 mM L-glutamine. The media was further supplemented with 100 ng/ml SCF (Amgen), 100 ng/ml FL (Amgen) and 50 ng/ml TPO(R&D Systems). Approximately 2-3 ml of the cell suspension was then injected into a 3 ml culture bag (through the septum) using a sterile syringe attached to a threaded cannula. The culture bag and cell contents were then maintained at 37° C. in a humidified atmosphere of 5% $CO_2$ in air. Re-selection after 4 days in culture (i.e. to remove lin+ cells generated during culture) was performed as described.

5. Cell Selection and Media Exchange in the Bioprocess

Lin$^-$ cell selection in the bioprocess was performed. Incubation of the cells with antibody cocktail and magnetic colloid was carried out inside the culture bag with the cells remaining in growth medium. The antibody cocktail and magnetic colloid were used at half the amounts suggested by the manufacturer. Following these steps, the cells were then allowed to flow through the enrichment element (either by directing flow via the stopcock or by attaching the bag to the enrichment element via septum/cannula mating). For flow rate experiments, a peristaltic pump was adapted to the primary cell culture container. Similar to the StemSep™ system, the conduit having an enrichment element was placed in an external magnetic field prior to separation. Upon passing through the conduit, and thus the enrichment element, the now purified lin$^-$ cells flow into the second culture chamber and were collected for further processing.

Media exchange can be performed on enriched lin$^-$ cells in the culture bags. Briefly, the cells are centrifuged by placing the culture bag into a 15 or 50 ml conical centrifuge tube (tissue paper can be used to stabilize the bag and prevent the bag from collapsing). The tube is then centrifuged for 5 min at approximately 1000 rpm after which time a cell pellet is visible at the bottom of the culture bag. The media is then carefully removed through the self-sealing septum using a sterile syringe. Care must be taken to prevent cells from being removed. Fresh media is then added through the same septum. This process can be adapted for automated media exchange.

6. Phenotypic Analysis

Phenotypic analysis was performed using flow cytometry. CD34, CD38, CD19 and CD33 expression was analyzed by first collecting and washing cells in ice cold HBSS containing 2% HSA (HBSS-HS). 5×10$^4$ to 100×10$^5$ cells were then resuspended in 100 µl HBSS-HS containing saturating amounts of the appropriate antibodies or isotype controls for 30 min on ice. Stained cells were then washed using HBSSHS and resuspended in a 10% formalin solution (Fisher, Nepean, ON, Canada). Fixed cells were then analyzed immediately using flow cytometry or placed at 4° C. for later analysis. CD45 and HLA-abc expression was assessed as described below. Flow cytometric analysis was performed using a Coulter EPICS XL with 4Color Expo software or a Coulter EPICS Elite with Elite software (Beckman Coulter, Miami, Fla.). CD34, CD38, CD19, CD33, CD45 and HLA-abc expression was assessed using anti-CD34-PE, anti-CD38-FITC, anti-CD19-PE, anti-CD33-PE, anti-CD45-PE/FITC and anti-HLA-abc-FITC (Beckman Coulter). Isotype controls were tested using anti-IgG$_1$-PE, anti-IgG$_1$-FITC and anti-IgG$_{2a}$-FITC (Beckman Coulter).

7. Colony Forming Cell (CFC) and Long Term Culture-Initiating Cell (LTC-IC) Assays Non-cultured or post-cultured cells were assayed for CFC content by plating 500 cells into methylcellulose media (MethoCult™, Stem Cell Technologies) containing 1% methylcellulose in Iscove's MDM, 30% FBS, 1% BSA, 10-4 M 2-mercaptoethanol, 2 mM L-glutamine, 50 ng/ml rhSCF, 10 ng/ml rhGM-CSF, 10 ng/ml rhIL-3 and 3 units/ml rhEPO. After 14 days of incubation, duplicate or triplicate cultures were scored for CFC content and frequency.

LTC-IC assays were performed by initially seeding 2000 cells on to irradiated human stromal cells (M2-10B4) in Swell plates. Cell were allowed to incubate for 5 weeks at 37° C. with weekly half media exchanges using MyeloCult™ media (Stem Cell Technologies) containing alpha-MEM, 12.5% HS, 12.5% FBS, 0.2 mM inositol, 20 micromolar folic acid, 10$^{-4}$M 2-mercaptoethanol, 2 mM L-glutamine, and 10$^{-6}$ M freshly dissolved hydrocortisone. After 5-weeks, the entire contents of each well were harvested by trypsinization and plated into methylcellulose media (see above). LTC-IC content and frequency was then determined by analysis of CFCs present after 14-days.

8. Transplantation of Cells into Non-Obese Diabetic/Severe Combined Immunodeficient (NOD/SCID) Mice Either fresh lin$^-$ cells or the progeny of lin$^-$ cells grown using the culture conditions described were transplanted into sublethally irradiated (3.6 Gy) 8-10 week old NOD/SCID mice using either intravenous (to test for LT-SRCs) or intrafemoral (to test for R-SRCs) injection. NOD/SCID mice received transplants of either fresh lin$^-$ cells or the progeny of lin$^-$ cells grown using the bioprocess (see above). For intravenous studies, cells were introduced via a standardized tail vein injection method as previously reported[71]. For intrafemoral studies, the mice were first anesthetized using a 2.5% avertin solution. The right knee was then bent and 25 µl of the cell sample was injected through the knee joint directly into the BM cavity of the right femur[131].

At the end of the experiment (6-8-weeks for IV; 2-weeks for IF), mice were sacrificed and the bone marrow from the right and left femurs were collected and analyzed for human cell engraftment. The bone marrow from mice receiving cells IV were pooled prior to analysis, while the bone marrow samples from mice undergoing IF transplants were analyzed separately. Erythrocytes were removed using ammonium chloride lysis (Stem Cell Technologies) and human engraftment was determined by suspending cells in 100 microliters of HBSS-HS and incubating with saturating amounts of CD45/HLA-abc antibodies or isotype controls for 30 min on ice. Stained cells were then washed and re-suspended in HBSS-HS containing propidium iodide (PI) to stain for dead cell content. Cells were then analyzed for human cell content (CD45+) using flow cytometry. Transplanted NOD/SCID mice were scored positive if at least 0.1% of the BM cells collected expressed human CD45 using FACS analysis.

9. Reverse Transcriptase-Polymerase Chain Reaction (RT-PCR)

TGF-beta and MIP-1α mRNA expression was determined using RT-PCR. Briefly, total cellular mRNA was collected by lysing cells in 500 µl Trizol Reagent (Invitrogen, Groningen, The Netherlands) for 5 min followed by addition of 100 µl chloroform. After centrifugation at 12,000 g for 15 min, the aqueous phase was collected and mixed with isopropanol to precipitate the mRNA. The mRNA pellet was then obtained by centrifugation at 12,000 g for 10 min, washed in 70% ethanol and re-suspended in sterile water. mRNA concentration was then determined using a microQuant plate reader (Biotek Instruments, Winooski, Vt.).

Synthesis of mRNA into cDNA was performed by mixing 1-5 µg of total mRNA with 1 microliter oligo-dT and sterile water to a final volume of 12 microliters in a microcentrifuge tube. The mixture was then heated to 70° C. for 10 min. and quickly chilled on ice. A mixture of 4 microliters 5× first strand buffer, 2 microliters 0.1 M DTT and 1 microliter of a 10 mM dNTP mix (10 mM each DATP, dGTP, dCTP and dTTP) was then added to the tube (Invitrogen) and the contents were incubated at 42° C. for 2 min after which time 1 microliter of reverse transcriptase enzyme (SUPERSCRIPT™, Invitrogen) was added. Genomic controls were established by not adding the enzyme to specified samples. The mixture was then incubated for an additional 50 min at 42° C. followed by inactivation at 70° C. for 15 min. The resultant cDNA was then used for PCR Briefly, PCR was performed by mixing 2 microliters of the cDNA solution with 23 microliters of a solution containing 10 microliters 10× PCR buffer, 2-3 microliters 50 mM $MgCl_2$, 1 microliter 10 mM dNTP mix, 1 microliter sense primer (25 micromolar), 1 microliter anti-sense primer (25 micromolar), 1 microliter Taq polymerase (5U/ml) and 80 ml autoclaved water (Invitrogen). The PCR reaction was carried out using optimized reagent concentrations and temperatures that were specific to the primer of choice. The primers used were as follows:

```
TGF-beta/sense;
                                    SEQ ID NO:1
GCGACTCGCCAGAGTGGTTAT, TGF-beta/anti-sense;
                                    SEQ ID NO:2
ATAGTTGGTGTCCAGGGCTCG, MIP-1 alpha/sense;
                                    SEQ ID NO:3
TGCAACCAGTTCTCTGCATC,
and MIP-1 alpha/anti-sense;
                                    SEQ ID NO:4
ATCATGTTTGAGACCTTCAA,.
```

PCR products were then analyzed by running samples on a 1% agarose gel, staining with an ethydium bromide solution and visualizing bands under a UV source.

10. Semi-Quantitative RT-PCR

Semi-quantitative RT-PCR was performed as previously described[132] with slight modifications. First, a dilution series was produced in which cDNA was serially diluted by 10-fold (for a total of 4 samples). These samples were then subjected to PCR as described. For quantitative comparisons between treatments, only those samples that were found to be in the linear range of amplification were analyzed. β-actin was used as an internal control.

11. Enzyme-Linked Immunosorbent Assay (ELISA)

The secretion of TGF-beta and MIP-1 alpha was measured using Quantikine ELISA Kits (R&D Systems, Minneapolis, Minn.). Both were done according to the manufacturer's protocols. The amount of protein in each sample was determined by comparison to a standard curve. Data acquisition and analysis was done using a VERSAmax microplate reader (Molecular Devices, Sunnyvale, Calif.).

12. Statistical Analysis

Data presented in this document are ±standard error of the mean (SEM). Where reported, significant differences between test groups were determined using the Student's t-test.

The expansion of R-SRCs or LT-SRCs was quantified using limiting dilution analysis by applying Poisson statistics to the single hit model[71]. The frequency of R-SRCs and LT-SRCs was calculated by using the maximum likelihood estimator as previously described[133]. In all cases, calculated $\chi^2$ values were not significant ($p>0.10$) indicating that pooling of data between experiments was valid.

13. Total Cell and Progenitor Cell Expansion in Bioprocess: Subpopulation Selection without Media Exchange In initial studies implemented to test the bioprocess, cultured cells were subjected to subpopulation selection without media exchange to test the effects the enrichment element may have on overall cell growth. Phenotypic and functional assays were used to compare the expansion of total cells, $CD34^+$ cells, $CD34^+CD38^-$ cells and CFCs grown using either normal culture dishes or using the bioprocess. In order to test these two systems, parallel cultures were established in which $3\times10^5$ lin$^-$ cells were isolated and plated at $1\times10^5$ cells/ml into 1) two wells of a 24-well plate (1.5 ml/well) or 2) injected into a 3 ml cell culture bag. The cells were then allowed to grow for 4-days after which time they were subjected to subpopulation selection (to remove any lin$^+$ cells generated during the first 4 days of culture). The cells cultured in the 24-well plate were enriched using the standard StemSep™ column and protocol. After selection, the cells were then allowed to grow undisturbed for an additional 4-days.

Figure 3:
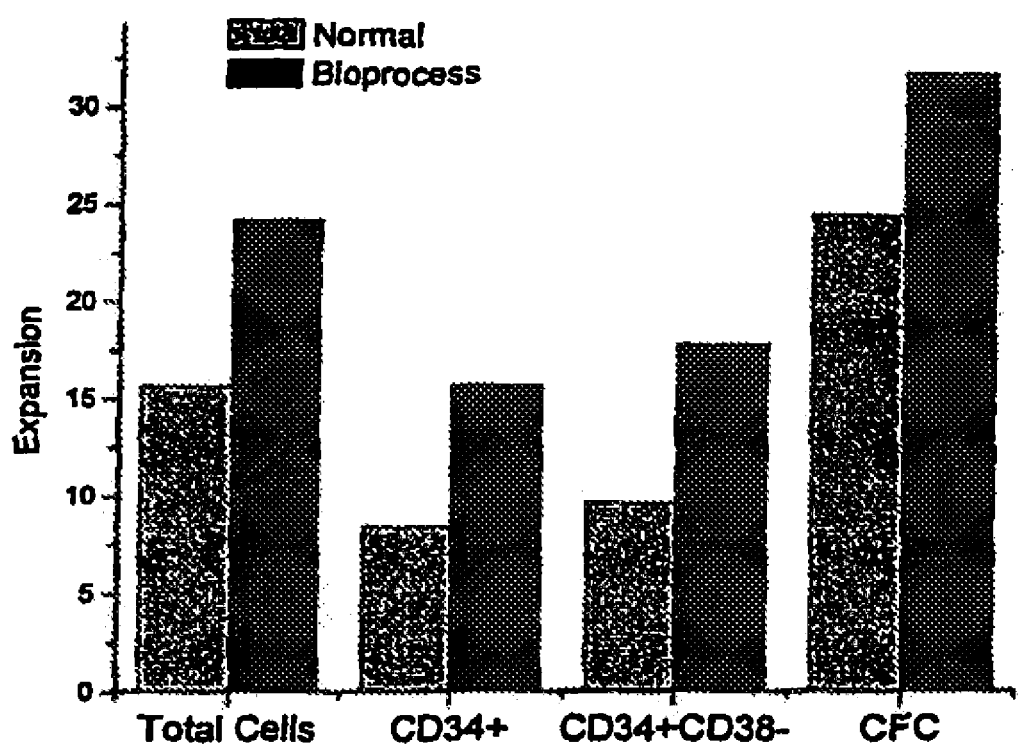
FIG. 3 is a graphical representation showing the extent of expansion of total cells, CD34+ cells, CD34+CD38− cells and CFCs, expanded by using either traditional culture dishes or using the present invention.

FIGS. 2 and 3 show the kinetic growth profiles for the various cell types, normalized to a starting cell sample of 150,000 (i.e. the number of input cells in 1 well of a 24-well plate), and the overall expansion of the cells compared to input numbers, respectively. The results of these studies have shown that the bioprocess can be used to grow total cells, $CD34^+$ cells, $CD34^+CD38^-$ cells and CFCs with expansions equivalent to, if not greater than, those obtained using standard culture dishes. Cells grown using the bioprocess also maintain similar functional and phenotypic characteristics as those cells grown in standard culture dishes. The data also shows that expansion of total and progenitor cell types can be maintained in the bioprocess over at least an 8-day culture period with minimal cell death (assayed using trypan blue dye exclusion). Importantly, these results demonstrate that the selection element and overall selection process (i.e. cells exiting and entering culture bags, flow through tubing, etc.) do not have a negative affect on overall cellular growth.

14. Control of Endogenous Factor Production

Figure 4:
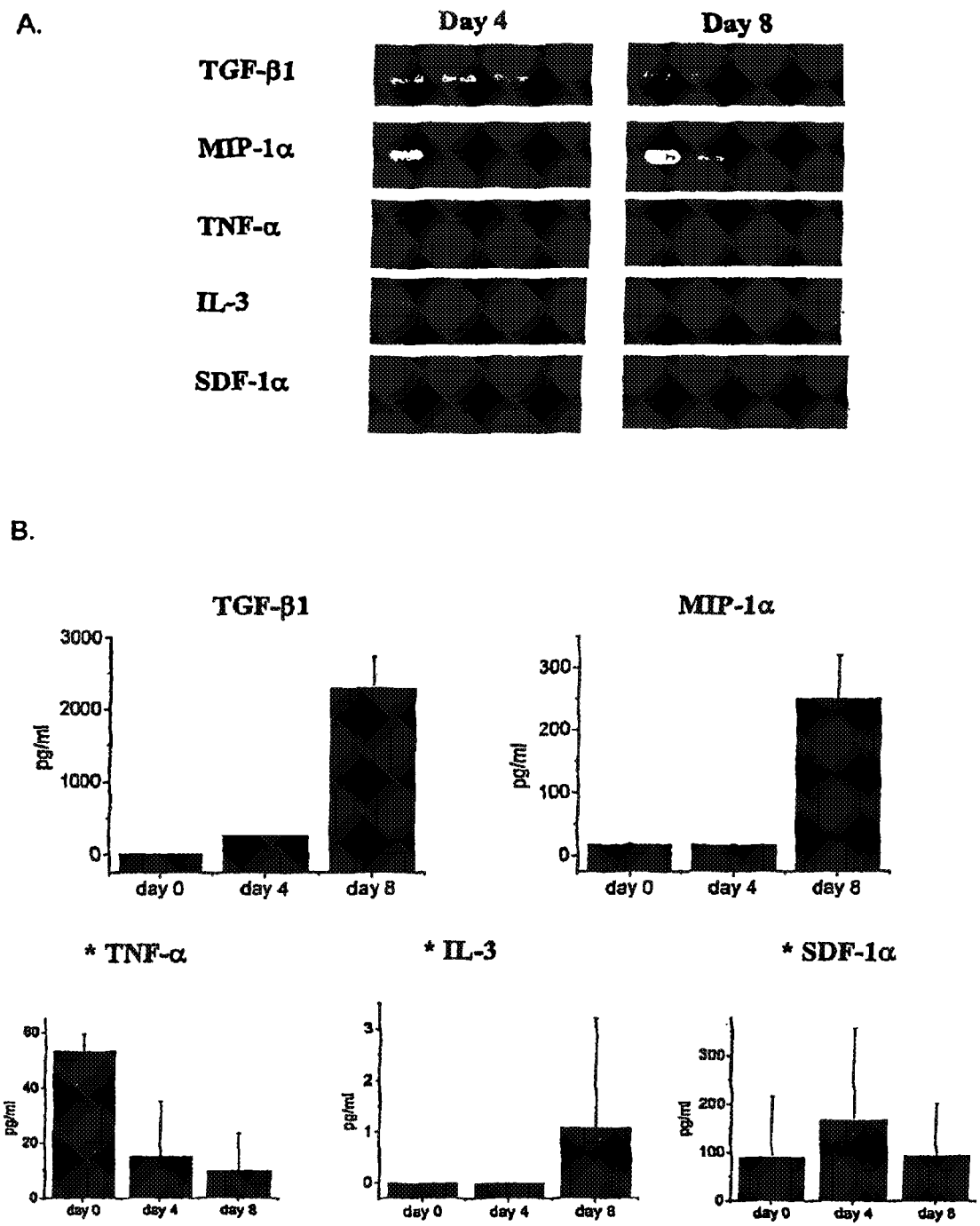
FIG. 4A depicts RT-PCR analysis of cultured hematopoietic cells showing expression levels of various inhibitory factors. Beta-actin was used as a control.
FIG. 4B is a graphical representation of ELISA analysis showing the secretion of inhibitory factors in culture. The detection of TGF-beta1 and MIP-1 alpha is illustrated.

With the knowledge that the culture manipulations were capable of increasing primitive progenitor cell expansion, experiments were designed to determine the effects of subpopulation selection and media exchange on the endogenous secretion of inhibitory factors. In these experiments 4 different culture conditions were tested: 1) no-selection and no-media exchange, 2) no-selection with media exchange, 3) selection with no media exchange and 4) selection and media exchange. Initial studies using RT-PCR and ELISA analysis showed that TGF-β1 and MIP-1α were expressed and secreted by cells in unmanipulated control cultures (FIG. 4). Other inhibitory factors were tested including TNF-α, IL-3 and SDF-1α none of which were detected in culture supernatants. Consequently, subsequent analysis focused on determining how our culture manipulations were affecting the concentration and production of TGF-β1 and MIP-1α.

The production of TGF-β1 was found to be significantly affected by subpopulation selection. Analysis of TGF-β1 secretion rates (on a per cell basis) demonstrated that subpopulation selection resulted in a significantly lower secretion rate regardless of whether or not media exchange was performed or not (FIG. 5A). This implies that the selection process removes a population(s) of cells which generate and secrete TGF-β1 in vitro. In order to confirm this finding, lin+ cells were specifically analyzed for their ability to express and secrete TGF-β1. In these studies lin$^+$ cells were collected either from the selection column (i.e. cells which were retained in column) or by FACS sorting. As shown in FIG. 5B, it was found that lin$^+$ cells do have the capacity to express and secrete TGF-β1 regardless of the method of collection. Lin$^+$ cells were found to secrete TGF-β1 at a rate of 6.8±0.1 pg/cell/hr (×10$^6$). These findings demonstrated that the selection process does indeed remove cells which secrete TGF-β1.

Analysis of MIP-1α production revealed a different phenomenon. It was found that MIP-1α secretion rates were compromised when media exchange was performed, regardless of whether subpopulation selection was performed or not (FIG. 6A). This finding indicated that the addition of fresh media to our cultures resulted in either the simple dilution of MIP-1α already present in culture supernatants or a direct or indirect downregulation of MIP-1α expression and/or secretion by those cells responsible for generating MIP-1α. Semi-quantitative RT-PCR of MIP-1α expression was then used as a means to determine if MIP-1α expression was affected by media exchange. In these experiments, cells were grown for 4-days, a time when MIP-1α expression was known to be high (previous experiments). The cells were then placed into fresh media for 24-hours in order to mimic a media exchange. After the 24-hour incubation time, the cells were then collected and analyzed. As shown in FIG. 6B, the expression of MIP-1α appeared to be significantly lower in those cells which were placed in fresh media. This implies that the lower levels of MIP-1α production may be due to the decreased expression of the MIP-1α gene.

15. Bioprocess for Umbilical Cord Blood Derived Hematopoietic Stem Cell expansion for Mammalian Transplantation In recent years, umbilical cord blood (UCB) has been established as an important source of hematopoietic stem cells (HSCs) for use in bone marrow transplantation (BMT) therapies to reconstitute hematopoiesis in patients with hematological and non-hematological disorders[134,135]. These cells have been used for both allogeneic-related and unrelated hematopoietic transplantation and, to date, more than 2000 transplants have been performed in both children and adults worldwide[127,136]. The advantages of using UCB include low incidences of graft-versus-host disease (GvHD), lack of risk to the donor, lack of donor attrition, and low viral transmission from donor to patient[137]. Importantly, UCB cells can be cryopreserved and selected without loss of HSC number and proliferative capacity, thus providing the potential for cord blood banking as a means to augment the donor pool[138].

The major disadvantage of UCB for transplantation is the limited number of stem cells that can be harvested from a typical cord blood collection[139,140]. The finding that a direct positive correlation exists between the dose of cells transplanted and patient recovery has led to intense investigation involving the ex vivo expansion of UCB derived HSCs[127-129]. Recently, a number of human clinical trials have shown that ex vivo expanded HSCs may aid in immune and hematopoietic recovery following intensive myeloablative therapy[1-4,141-146]. While promising, these studies have not yet consistently demonstrated advantageous hematological recovery in comparison to studies performed with non-expanded cells suggesting that repopulating stem cells may have only been maintained in culture[147]. However, there is a high demand for culture processes capable of robustly producing increased quantities of HSCs such as the bioprocess disclosed herein.

In general, a suitable process for production of undifferentiated cells for transplant must carefully consider both the efficacy and safety of the cellular product to be administered to the patient. As such, these processes should also meet the standards outlined by the Food and Drug Administration (FDA) which include the requirement for the system to be closed (i.e. no exposure to the environment or environmental contaminants), that the process be designed with biocompatible materials and that the process be sterile, sterilizable and pyrogen free (FDA, 2003). Single-use bioprocesses ensure low incidences of cell contamination as they avoid repeated use. Closed-system culture configurations that meet these requirements for expanding HSCs for transplant include culture chambers of gas permeable bags[148], stirred/spinner flasks[149,150] and flat bed perfusion bioreactors[151].

We have shown that mature blood cells (expressing lineage related markers; lin$^+$) produce soluble factors that prevent HSC expansion in vitro. By decreasing the concentration of these inhibitory hematopoietins in culture through subpopulation selection (i.e. the removal of mature cells secreting these factors) and media dilution/exchange processes, culture conditions were established which could support significant expansions of primitive progenitors as well as short- and long-term repopulating stem cells. In order to apply this culture technique in a clinical setting, we have designed a dosed-system bioprocess for ex vivo HSC expansion that incorporates in-line subpopulation selection and media dilution/exchange capacities. Here we show that the bioprocess is capable of expanding UCB derived hematopoietic stem and progenitor cells including CFCs, LTC-ICs and long-term non-obese diabetic/severe combined immunodeficient (NOD/SCID) repopulating stem cells (LT-SRCs). We also show that non-specific cell loss occurs during the subpopulation selection process, which ultimately lowers the overall expansion potential of the bioprocess, and that these losses can be minimized by controlling the bioprocess operating conditions. Accordingly the dosed-system bioprocess described, is capable of expanding HSCs to clinically relevant levels, for therapeutic transplantation into a mammal.

We have designed a dosed-system bioprocess that has the ability to perform subpopulation selection and media dilution/exchange processes for the expansion of HSCs. The bioprocess described consists of two cell culture chambers, more particularly culture bags and a subpopulation selective element, which is responsible for removing mature blood cells (lin+) from culture. The selection element comprises a conduit having a tube containing stainless steel beads and connects the two culture chamber bags to form the system (FIG. 7A). Furthermore, the bioprocess design is modular such that each component can be separated without exposing cell contacting areas (i.e. within the selection element and cell culture bags) to outside environmental contaminants. Finally, the bioprocess is a single-use system, which makes it attractive for clinical applications as the risk of cell contamination due to repeated use is removed.

The application of the bioprocess involves first introducing UCB derived lineage depleted (lin−) undifferentiated cells into the primary cell culture bag through a sterile self-sealing rubber septum. The cells are then maintained in culture and after a specified time lin+ undifferentiated cells, which are generated during culture, are removed. This is accomplished by linking lin+ undifferentiated cells to dextran coated iron particles and subsequently allowing them to flow through the selection element. The selection element is placed in an external magnetic field, which allows the particle labeled cells to be retained in the selection element. Flow rates are established using gravity. The enriched lin− cell population that flows through the selection element is then channeled into the secondary culture bag where media dilution/exchange is performed by centrifuging the container, removing spent media through a sterile self-sealing rubber septum and re-introducing fresh media through the same septum. The cells are then allowed to proliferate. Additional segregation and media exchange may be performed. Other methods of lin+ cell depletion can be envisioned including chemical targeting of lin+ cells, centrifugal elutriation, electromagnetic separation, or other methods described in the literature.

Subpopulation Selection and Media Dilution/Exchange

Initial studies were done to test the performance of the bioprocess. First, the ability of the subpopulation selection element to remove lin+ cells from culture was tested. For comparison, selection was also performed using the commercially available StemSep™ selection column, which efficiently removes lin+ cells from a heterogeneous cell sample. In these experiments, cultured (4-24 days) UCB derived lin− cells were exposed to the selection process (bioprocess and StemSep™ column). Flow cytometric analysis showed that during these culture times approximately $19.9 \pm 2.8\%$ (range: 2.5 to 49.0) of the cells expressed lin+ cell surface markers. The input cell numbers ranged from $1.1 \times 10^6$-$3.5 \times 10^6$ for the bioprocess and $1.7 \times 10^6$-$3.5 \times 10^6$ for the StemSep™ column. Cells were stained for the presence of lin+markers both pre- and post-selection.

Flow cytometric analysis confirmed that the subpopulation selection element was capable of efficiently removing lin+ cells from the cultured cell samples (FIG. 7B). Cells exiting the selection element were highly enriched for lin− cells with a purity of $99.7 \pm 0.2\%$. This was comparable to results with the StemSep™ column where purities of $99.6 \pm 0.1\%$ were observed. Furthermore, cells were not damaged during this process as trypan blue dye exclusion demonstrated that the cells remained viable following subpopulation selection.

Experiments were also initiated to test the media dilution/exchange process. To test this, a range of $5 \times 10^5$ to $2 \times 10^6$ cells were introduced into 3 ml or 7 ml culture bags. The bags were then subjected to centrifugation at 1000 rpm after which spent media was removed and replaced with fresh media through a self-sealing rubber septum. Cell counts of the now re-fed cells were then taken to determine if cell loss occurred during this process. The results conclusively demonstrated that media dilution/exchange could be performed without significant cell loss with an average cell recovery of $98.9 \pm 0.7\%$. Finally, it is important to note that the culture containers were able to withstand centrifugation without noticeable damage.

Total Cell and Progenitor Cell Expansion in Bioprocess: Subpopulation Selection and Media Exchange To determine the overall effectiveness of the bioprocess to grow hematopoietic progenitor cells, UCB lin− cells were subjected to 8-day cultures in which cells were exposed to the subpopulation selection and media dilution/exchange processes at day 4. Phenotypic as well as in vitro functional assays were used to quantify the expansion of total cells and progenitor cells including CD34+ cells, CD34+CD38− cells, CFCs and LTC-ICs at input as well as on days 4 and 8.

Figure 8:
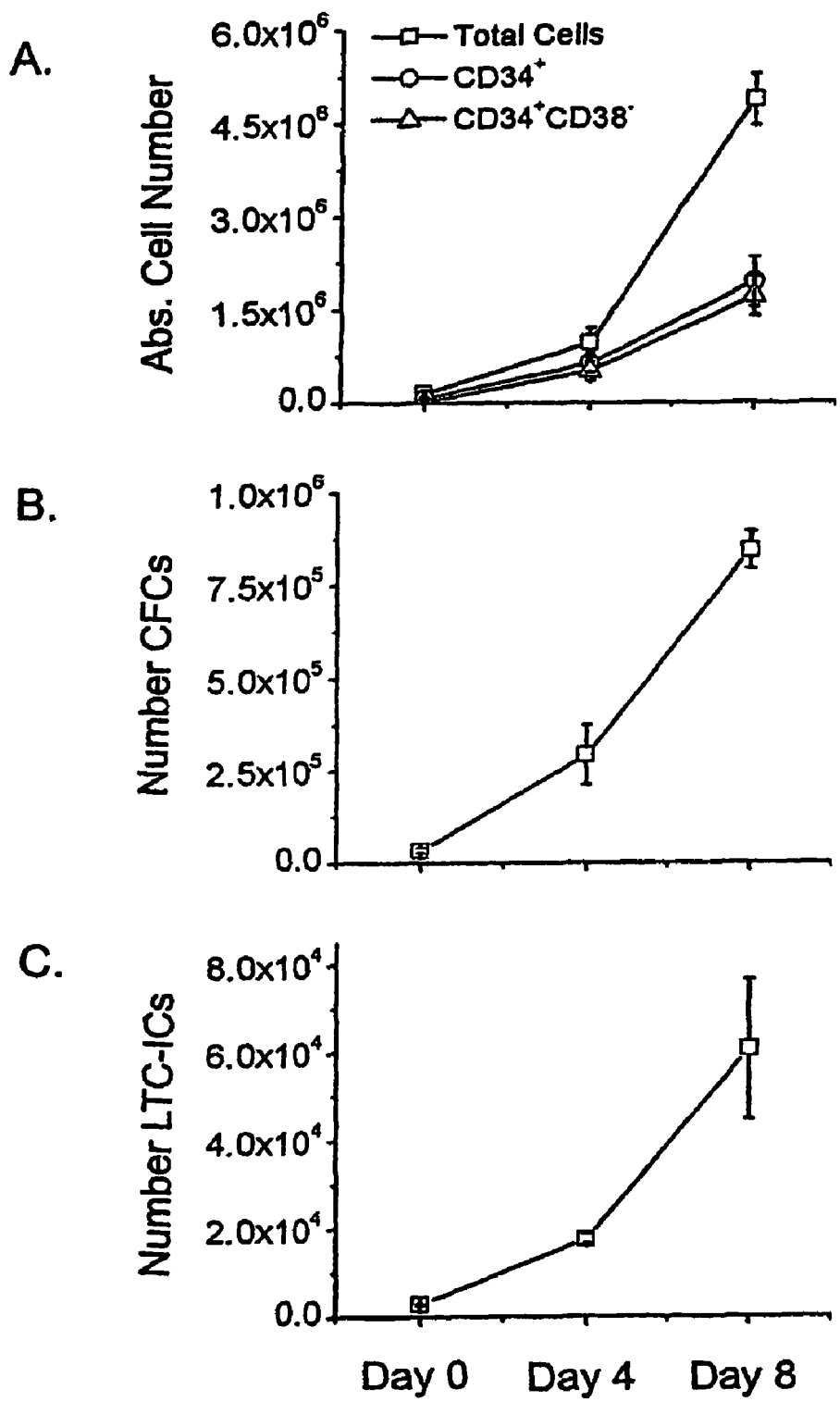
FIGS. 8A-C show the absolute numbers of hematopoietic cells generated in the bioprocess. Purified UCB lin− cells ($1 \times 10^5$ cells/mi) were cultured for 8 days in the bioprocess with subpopulation selection and media dilution/exchange occurring at day 4. Kinetic growth profiles for total cells (A), CD34+ cells (A), CD34+CD38− cells (A), CFCs (B), and LTC-ICs (C) are shown over the 8-day culture period (n=4).
Figure 9:
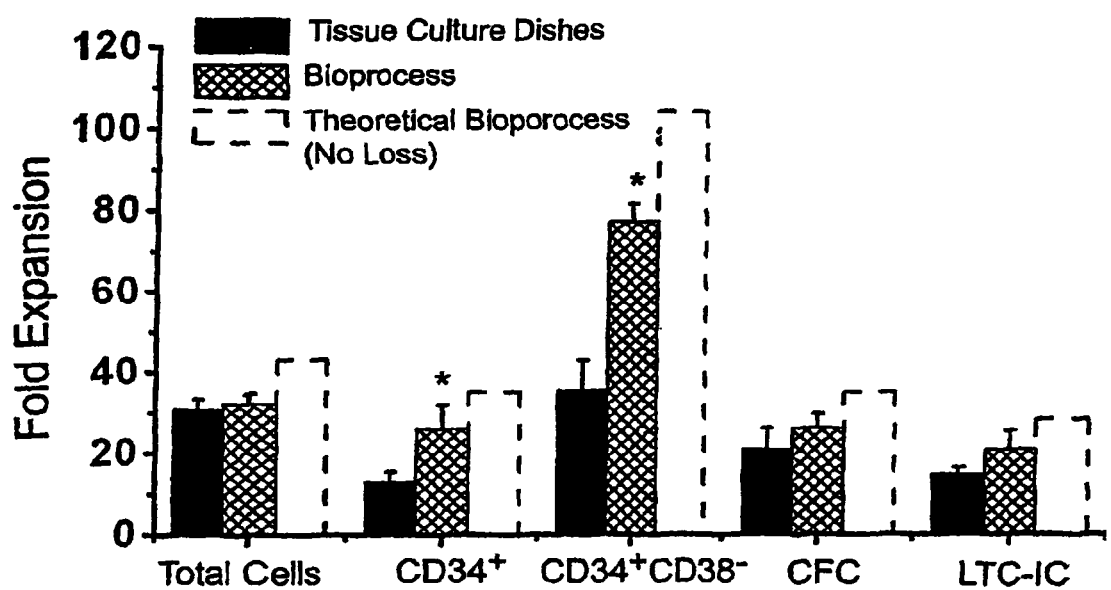
FIG. 9 illustrates the calculated expansions of total cells, CD34+ cells, CD34+CD38− cells, CFCs and LTC-ICs relative to input for cells grown using the bioprocess (n=4). For comparison, results of cells grown using standard tissue culture dishes are also provided. Also shown are the theoretical expansions that should be observed in the bioprocess with decreased cell loss (see Section 4.2.5). This value was calculated by multiplying the observed expansion by a correction factor reflecting the percentage of non-specific cell loss. The value of the correction factor was 1.3449.

Analysis of the kinetic growth profiles of the various cell types revealed that the bioprocess could effectively increase the absolute numbers of total cells, CD34+ cells, CD34+CD38− cells, CFCs and LTC-ICs over the 8-day culture period (FIG. 8). Furthermore, the observed fold expansions of total cells, CFCs and LTC-ICs were comparable to those obtained using standard tissue culture dishes as described above (FIG. 9). Cells grown in the bioprocess resulted in expansions, relative to input values, of $32.0 \pm 2.7$, $25.9 \pm 3.7$ and $20.8 \pm 4.6$ for total cells, CFCs and LTC-ICs respectively, while cells grown in tissue culture dishes showed expansions of $30.8 \pm 2.6$, $20.7 \pm 5.2$ and $14.6 \pm 1.6$ for the same cell types. Interestingly, a significant ($p < 0.05$) increase in CD34+ and CD34+CD38− cells were generated in the bioprocess over the 8-day culture period upon comparison to standard tissue culture dishes (FIG. 9). In the bioprocess CD34+ and CD34+CD38− cells showed expansions of $26.0 \pm 5.8$ and $77.0 \pm 4.3$ respectively while in culture dishes values of $12.9 \pm 2.5$ and $35.5 \pm 7.3$ were observed.

The data also showed that the expansion of hematopoietic stem and progenitor cell types can be maintained in the bioreactor with minimal cell death (assayed using 7-AAD exclusion), demonstrating that the subpopulation selection element and overall selection process (i.e. cells exiting and entering culture bags, flow through tubing, etc.) do not have a negative affect on overall cellular viability.

Human Cell Engraftment in NOD/SCID Mice

Figure 10:
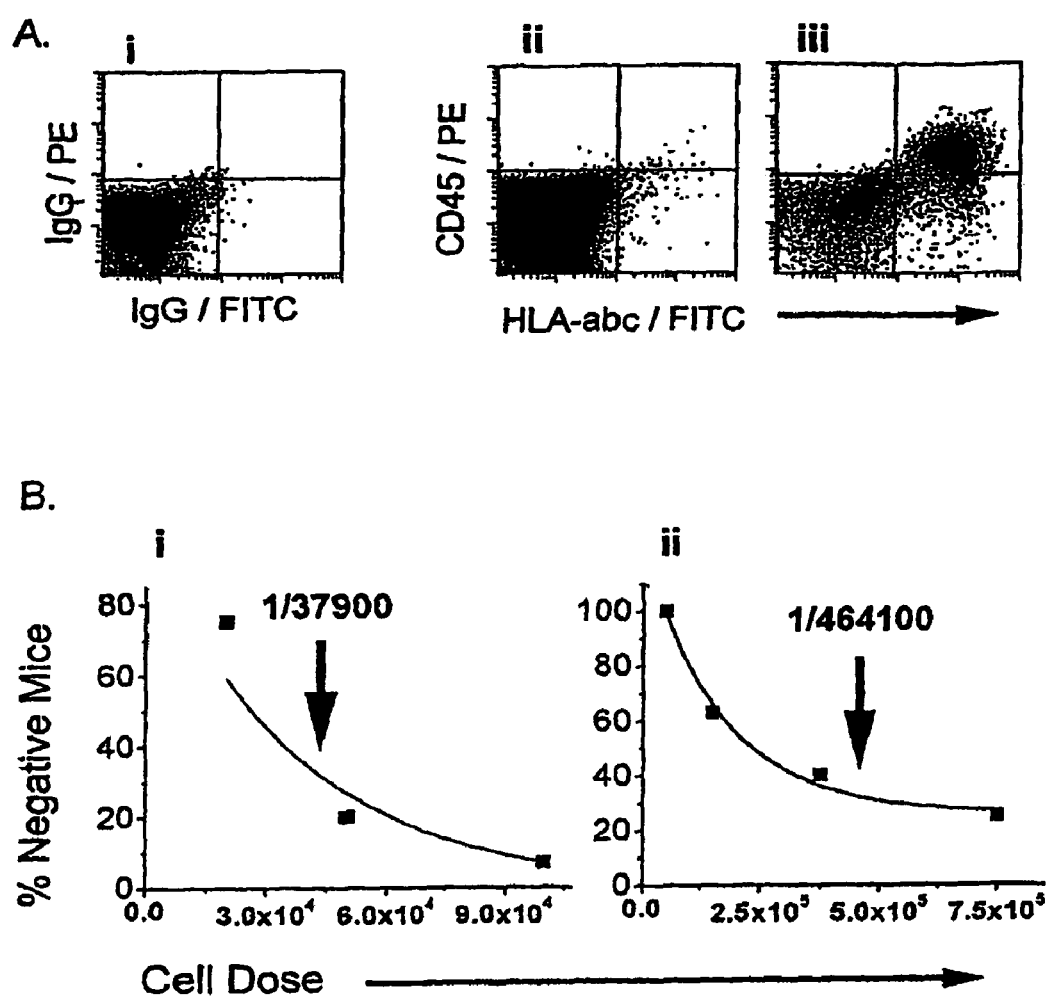
FIGS. 10A and 10B illustrate human cell engraftment in NOD/SCID mice following intravenous injection. (A) Representative flow cytometric plots showing the presence of human $CD45^+HLA-abc^+$ cells in NOD/SCID mice (Aiii). A control NOD/SCID mouse that did not receive cells is also shown (Aii) along with a representative isotype control (Ai). (B) Limiting dilution analysis was performed in NOD/SCID mice to determine the frequency of LT-SRCs present in fresh UCB lin− cells (n=24) and expanded cells (n=25). The resultant engraftment frequencies for fresh lin− cells (Bi) and cultured cells (Bii) are shown for each cell dose and overlayed with curves representing results from the maximum likelihood estimator. Isotype controls were established for each sample.

In order to determine if cells grown in the bioreactor were capable of long-term repopulating potential, LDA using the NOD/SCID mouse model was performed. Fresh UCB lin− cells (n=24) or cultured cells (n=25) were injected intravenously into NOD/SCID mice and, after 8 weeks, the mice were sacrificed and examined for the presence of human cells (i.e. CD45+HLA-abc+) using flow cytometry (FIG. 10A). Engraftment was detected when $1.0 \times 10^5$ (14/15 mice), $5.0 \times 10^4$ (4/5 mice) and $2.0 \times 10^4$ (1/4 mice) fresh lin− cells were transplanted (FIG. 10Bi). A higher inoculum range was used for transplantation of bioreactor expanded cells as the expanded population was no longer enriched for lin− cells. Engraftment was observed with cell doses of $7.5 \times 10^5$ (6/8 mice), $3.75 \times 10^5$ (3/5 mice) and $1.5 \times 10^5$ (3/8 mice) cells, however, no engraftment was observed with $5.0 \times 10^4$ (0/4 mice) cells (FIG. 10Bii). Based on this data, the frequency of repopulating HSCs in fresh lin− cells was found to be approximately 1/37900 (95% confidence interval, 1/22076-1/66961) while that in the expanded population was 1/464100 (95% confidence interval, 1/266200-1/888300) both of which were calculated using the maximum likelihood estimator. Coupled with the overall total cell expansion for these experiments, a calculated expansion for LT-SRCs of approximately 4.2-fold was observed.

Cell Loss in the Subpopulation Selection Element

In performing the expansion studies, it was found that the actual numbers of lin− cells exiting the selection element did not correlate to the theoretical numbers of cells that were expected. Table 1 summarizes these findings and provides a detailed explanation of the calculations used to obtain these results. In all instances, lower numbers of cells were observed exiting the selection element (in comparison to theoretical values) suggesting the occurrence of non-specific cell loss. This non-specific loss was also observed with the StemSep™ column. The extent of non-specific cell loss was calculated to be 34.49±6.45% and 32.38±12.99% for the bioprocess and StemSep™ column respectively (Table 1).

In order to abrogate cell loss, flow rate was initially tested as a possible mechanism to decrease and/or prevent cell loss. Previous studies have demonstrated that flow rate can significantly affect the performance of a similar immunomagnetic selection column. In order to control flow rate through the bioreactor, a peristaltic pump was used to 'push' the cells out of the primary cell culture bag, through the conduit having the selection element and into the secondary cell culture bag. By simply replacing the primary cell culture bag with one fabricated with an additional port (FIG. 11A), the peristaltic pump could be attached upstream of the process and used to control flow rate. Average flow rates tested included 0.45±0.03 (gravity induced flow rate), 0.62±0.04, 0.76±0.06 and 1.25±0.07 ml/min.

cells that passed through the selection element were collected and stained for the presence of contaminating lin+ cells. The results showed that at the flow rate of 1.25±0.70 the purity of lin− cells exiting the selection element was approximately 97.98±1.40% (FIG. 11B). Interestingly, all flow rates tested provided high levels of purity suggesting that while flow rate affected percent recovery it did not have a significant affect on cellular purity. Taken together, these studies allowed us to conclude that the bioreactor should be operated at an optimal flow rate of at least 1.25 ml/min in order to minimize the effects of non-specific cell loss.

Theoretical calculations were done to determine the expected expansion of the various cell types in response to the decreased cell loss. These values were calculated by multiplying the observed expansion by a correction factor reflecting the percentage of non-specific cell loss (~34.49%). The value of the correction factor was 1.3449. These corrected values are reflected in FIG. 9.

TABLE 1

Experiments showing the extent of non-specific cell loss occurring though the subpopulation selection element.

| Experiment No. | Total Input Cell Number | % Lin+ Pre Column | Theoretical Number of Cells Exiting Selection Element | Actual Number of Cells Exiting Selection Element | % Cell Loss[a] |
|---|---|---|---|---|---|
| Bioreactor system (gravity) | | | | | |
| 1 | 3412500 | 10.5 | 3054188 | 1968750 | 35.84 |
| 2 | 3500000 | 3.70 | 3370500 | 2500000 | 26.15 |
| 3 | 3500000 | 3.70 | 3370500 | 1612500 | 52.17 |
| 4 | 1109375 | 30.85 | 767133 | 589375 | 23.79 |
| | | | Avg. | | 34.49 |
| | | | SEM | | 6.45 |
| StemSep ™ column | | | | | |
| 1 | 3412500 | 34.15 | 2247131 | 1864125 | 17.04 |
| 2 | 3491250 | 10.8 | 3114195 | 1837605 | 40.99 |
| 3 | 3500000 | 2.5 | 3412500 | 1199760 | 64.84 |
| 4 | 2350000 | 29.1 | 1666150 | 1555476 | 6.64 |
| | | | Avg. | | 32.38 |
| | | | SEM | | 12.99 |

Percent cell loss is calculated by first taking the difference between the theoretical number of cells that should pass through the selection element [i.e. total input cell number−(total input cell number*% lin+ cells)] and the actual number of cells existing the selection element, dividing this value by the theoretical number of cells and multiplying by 100.

For each flow rate, cell samples containing varying amounts of lin+ cells and input cell numbers were placed into the primary cell culture bag. The cells were then subjected to the subpopulation selection process. Post-selection cells were collected, counted and analyzed for the presence of lin+ cells using flow cytometry. The results convincingly showed that increasing flow rate significantly decreases non-specific cell loss through the selection element (Table 2). At the maximum tested flow rate of 1.25±0.07 ml/min, approximately 98.05±1.27% of the lin− cell population was recovered which was significantly (p<0.05) better than all other flow rates tested where 65.51±6.45, 75.88±3.17 and 80.54±4.81% recovery was observed at flow rates of 0.45±0.03, 0.61±0.04 and 0.76±0.06 ml/min, respectively (FIG. 11B).

In order to show that at this increased flow rate the purity of the exiting lin− cell population would not be compromised,

TABLE 2

Effects of flow rate on yield and purity of lin− cells exposed to the subpopulation selection process.

| | Flow Rate Tested (ml/min) | % Input lin+ Cells | % Output lin+ Cells | % Recovery lin− Cells | % Purity lin− Cells |
|---|---|---|---|---|---|
| | — | 10.50 | 0.46 | 64.16 | 99.54 |
| | 0.45 | 3.70 | 0.43 | 73.85 | 99.57 |
| | 0.39 | 3.70 | 0.03 | 47.83 | 99.97 |
| | 0.51 | 30.85 | 0.81 | 76.21 | 99.19 |
| Avg. | 0.45 | 12.2 | 0.43 | 65.51 | 99.57 |
| SEM | 0.03 | 6.42 | 0.16 | 6.45 | 0.16 |
| | 0.69 | 34.15 | 7.45 | 68.05 | 92.55 |
| | 0.60 | 10.50 | 0.83 | 75.79 | 99.17 |
| | 0.50 | 10.50 | 0.59 | 83.60 | 99.41 |
| | 0.68 | 29.10 | 5.76 | 76.11 | 94.24 |
| Avg. | 0.62 | 21.06 | 3.66 | 75.88 | 96.34 |
| SEM | 0.04 | 6.18 | 1.74 | 3.17 | 1.74 |
| | 0.86 | 3.70 | 0.05 | 86.28 | 99.95 |
| | 0.64 | 3.70 | 0.03 | 77.41 | 99.97 |

TABLE 2-continued

Effects of flow rate on yield and purity of lin– cells exposed to the subpopulation selection process.

|  | Flow Rate Tested (ml/min) | % Input lin+ Cells | % Output lin+ Cells | % Recovery lin– Cells | % Purity lin– Cells |
|---|---|---|---|---|---|
|  | 0.90 | 3.70 | 0.02 | 68.48 | 99.98 |
|  | 0.71 | 30.85 | 0.88 | 89.98 | 99.12 |
| Avg. | 0.76 | 10.49 | 0.25 | 80.54 | 99.76 |
| SEM | 0.06 | 6.79 | 0.21 | 4.81 | 0.21 |
|  | 1.15 | 3.70 | 0.02 | 96.47 | 99.98 |
|  | 1.29 | 3.70 | 0.01 | 100.00 | 99.99 |
|  | 1.20 | 3.70 | 0.02 | 93.78 | 99.98 |
|  | 1.50 | 30.85 | 7.19 | 100.00 | 92.81 |
|  | 1.11 | 23.88 | 2.85 | 100.00 | 97.15 |
| Avg. | 1.25 | 13.17 | 2.52 | 98.05 | 97.98 |
| SEM | 0.07 | 5.90 | 1.52 | 1.27 | 1.40 |

The expansion of HSC in vitro is an area of active interest in the field of stem cell transplantation. The ability to expand hematopoietic progenitor cells and repopulating stem cells using a novel methodology that incorporates subpopulation selection (i.e. removal of lin+ cells from culture) and media exchange strategies to reduce the concentration of inhibitory factors in culture, provides a source for HSCs. The results of studies with the closed-system bioprocess show that the bioprocess supports the expansion of UCB derived stem and progenitor cells including CD34+ cells, CD34+CD38– cells, CFCs, LTC-ICs and LT-SRCs.

The subpopulation selection element was shown to efficiently remove contaminating lin+ cells from culture. However, it was observed that during this process a considerable amount of non-specific cell loss occurred (i.e. lin– cells were retained in the selection element) indicating that the full expansion potential of the bioprocess was not being realized. The studies presented here showed that non-specific cell loss could be decreased as a function of increased flow rate. By employing a peristaltic pump to increase flow rate, we were able to increase overall lin– cell recovery. Without being restricted to theory, an explanation for this observation may be the decreased residence time of the cells within the subpopulation selection element. The shorter time period spent in the selection element would decrease the probability of cells contacting non-specific binding sites which may otherwise retain them within the element. It is also possible that the slower flow rates generated by simple gravity may allow for 'pooling' or 'trapping' of the cell suspension within the pores of the selection element (possibly due to surface tension), in which case increased flow rate may simply allow the cell suspension to progress through the selection element more efficiently. Using a similar immunomagnetic selection column, we show that flow rate could significantly affect non-specific cell loss. The decrease in cell loss is a important as it results in significantly higher expansions of hematopoietic stem and progenitor cells within the bioprocess. Theoretical values, corrected for cell loss, are reflected in FIG. 9.

Interestingly, a significantly ($p<0.05$) greater number of CD34+ and CD34+CD38– cells were consistently generated in the bioprocess apparatus in comparison to standard tissue culture dishes without an accompanying increase in CFCs, LTC-ICs and LT-SRCs. A possible explanation comes from observations that direct changes in phenotype can occur when cells are exposed to in vitro culture conditions (von Laer et al., 2000). However, because both systems represent in vitro cultures, the differences in the expansion of these phenotypically defined cell populations may further be attributed to changes in culture configuration. Configuration differences may manifest themselves as dissimilar culture microenvironments involving parameters such as oxygen concentration, pH, metabolic by-product concentration and local cytokine concentration. Discrepancies have been reported where the expansion of phenotypically defined cells (including CD34+ CD38– cells) do not always produce proportional increases in functional progenitor cell numbers (Danet et al., 2001; Dorrell et al., 2000; Mobest et al., 1999; Spangrude et al., 1995).

While the main function of the selection element is to remove differentiated lin+ cells from culture, it is also general in its use such that any cell type with a characteristic phenotype can be removed. This characteristic makes the bioprocess versatile for use in a variety of alternative applications. For example, donor T cells are responsible for the onset of graft-versus-host disease (GvHD) (Ho et al., 2001). It has been suggested that the removal of subsets of donor T cells including those expressing CD8 can reduced the incidence of acute GvHD in patients undergoing allogeneic stem cell transplantation (Baron et al., 2002). Because the bioprocess incorporates simple cell selection processing based on cell surface phenotype, it is possible to generate a culture strategy whereby contaminating T cells are concomitantly removed during culture. In this manner, the resulting cell graft generated using the bioprocess would not only be enriched for repopulating stem cells but also devoid of cells responsible for GvHD, increasing the probability for successful long-term engraftment.

A wide range of cell numbers can be obtained from typical cord blood collections (Cairo et al., 1997), suggesting that the bioprocess can perform over a wide range of input cell numbers. The modularity of the bioprocess makes this feasible. By keeping the culture concentration of cells constant for all cord blood samples (100,000 cells/ml was used in this study), the only alteration to the bioprocess to accommodate the variability in cell numbers would be the use of cell culture bags with differing volumetric capacities. The fact that cell culture bags can be removed from the bioprocess without compromising cell-contacting areas would make the interchange of bags for this purpose possible. Furthermore, it has been previously reported that the expansion of primitive cells (i.e. CD34+) obtained from different UCB and bone marrow samples is highly variable (De Bruyn et al., 1997; Koller et al., 1996). Therefore, the bioprocess is able to conform to samples that may have high proliferative potentials, in which case it may be necessary to transfer cells into larger volume bags. The ability to control the flow of cells in the bioprocess from one bag to another (i.e. through the selection element) under closed conditions would make this possible. The versatility of the bioprocess regarding these issues allows the culture of cord blood samples with highly variable cell numbers and growth potentials to be cultured in a standardized process.

The closed-system bioprocess described herein is capable of efficiently and robustly expanding hematopoietic stem and progenitor cells. As such, it should prove to be a valuable tool for the development, implementation and success of clinical transplantation therapies requiring these types of cells.

16. Modifications of the Method of the Present Invention

In the collection stage samples are collected, e.g., in a 250 ml Baxter collection bag by gravity flow. Collection is initiated within 15 minutes of delivery (or on an undelivered placenta). Samples are collected and stored temporarily at 25° C. with no drop off in viability, for example, samples are stored for up to 72 hours before processing, and decrease in total cell viability, as assessed by FACS, is negligible.

In the processing stage samples are mixed with pentastarch by methods known in the art for cell enrichment. Processing stage samples can also be spun without addition of starch or Ficoll (12 min. spin) and may be processed directly in bags. Sample are frozen with DMSO. The NYBC thawing process is also useful. It is not necessary to culture the cells overnight. RBCs are lysed by ammonium chloride. Cells are run through a StepSep column with all washes in HANKS buffer or PBS buffer and at a temperature from about 4 degrees Celsius to about 37 degrees Celsius.

Cells are cultured for 2 to 7 days (preferably 4 days) in serum-free medium plus growth factors, for example SCF [about 100 ng/ml], TPO [about 50 ng/ml], Flt-3L [about 100 ng/ml/]. Cells are run through a StepSep column with all washes in HANKS buffer or PBS buffer from about 4 degrees Celsius to about 37 degrees Celsius. Cells are cultured from about 2 to about 7 days (preferably 4 days) fresh serum-free medium plus growth factors: SCF (about 100 ng/ml), TPO (about 50 ng/ml), Flt-3L (about 100 ng/ml). Phenotypic analysis is performed, for example FACS detection of CD34 or CD38 expressing target cells or other such markers. In vitro detection and activity assays include CFC or LTC-IC. In vivo detection and activity assays are mouse NOD-SCID or IF. RBC depletion is typically performed before freezing. Growth periods are preferably 4 day cycles plus media exchange. A rest period is not typically required.

The results disclosed herein demonstrate that the claimed bioprocess apparatus and methods, provide a methodology to expand hematopoietic stem or progenitor cells, based on cell enrichment and media exchange, in a controllable, closed-system. In its ability to expand total cells, CD34$^+$ cells, CD34$^+$CD38$^-$ cells, CFCs, and LTC-ICs, the bioprocess performs in an equivalent, if not better, manner when compared to standard systems known in the art (i.e. culture dishes). In addition, the built-in cell enrichment process has been shown to be as efficient as commercially available columns in removing lin$^+$ cells from culture, and media exchange can easily be performed without cell loss.

17. Total Cell and Progenitor cell Expansion in Open System for Transplantation into a Mammal Umbilical cord blood (UCB) derived hematopoietic stem cells (HSCs) provide a therapeutically efficacious source of cells to treat a variety of hematological disorders[134,135]. Unfortunately, the low numbers of HSCs isolated from a typical UCB donation limits this therapy to pediatric patients[130,134]. Effective HSC expansion represents an attractive solution, however this goal has remained elusive despite >20 years of experimentation in animal models and human clinical trials[147]. Even the seemingly attainable goal of using culture—generated progenitors to shorten neutrophil and platelet recovery times in patients following myeloablative chemotherapy[143-145] has been generally ineffective[147].

Virtually all prior attempts to stimulate stem cell expansion ex vivo have focused on the effects of various combinations of known (supplemented) or unknown (provided by feeder cells or conditioned media) cytokines and growth factors[147,152]. The challenge of this approach is to identify factors that exclusively or predominantly act on HSCs and not on their differentiated progeny, which will otherwise ultimately outgrow the stem cell compartment. Fundamentally, such factors must induce HSCs to undergo symmetrical self-renewal divisions (as opposed to induction of differentiation) in a dynamic culture microenvironment that is, or is rapidly becoming, heterogeneous. Given the spectrum of molecules expressed throughout the hematopoietic hierarchy[26,27], success using this approach has been understandably difficult and, in fact, transplantation studies using non-obese diabetic/severe combined immunodeficient (NOD/SCID) mice has shown that cytokine supplementation strategies generally result in the loss, maintenance or moderate expansion of human repopulating stem cells[5,8,10,153,154]. Even recent studies using cellular proteins that typically target HSC development (e.g. hedgehog[155], HOXB4[156] and Wnt$_{157}$ proteins), have resulted in limited human HSC expansion.

Hematopoietic progenitor and mature blood cell populations secrete regulatory proteins whose actions are known to inhibit HSC proliferation and/or induce stem cell differentiation[21,22,24,27,158]. Thus, it is likely that the generation of these cells due to induced or "background" differentiation, which typically occurs during all stem cell culture, and their secreted products limits HSC expansion in vitro. However, the effects of these endogenously secreted negative regulators are currently under investigated. Here we demonstrate that the secretion of such factors represents a feedback control mechanism through which differentiated blood cells can significantly affect the proliferative status of HSCs. We further demonstrate that the global control of negative regulator production represents a simple means to overcome the block to HSC expansion observed in vitro. To show this, we developed a simple global culture manipulation (GCM) technique, based upon semi-continuous subpopulation selection and media dilution, to proactively control the production of negative regulators in a manner that is independent of exogenous factor supplementation to produce a culture microenvironment capable of selectively expanding primitive progenitor cells as well as short- and long-term repopulating human HSCs.

Figure 12:
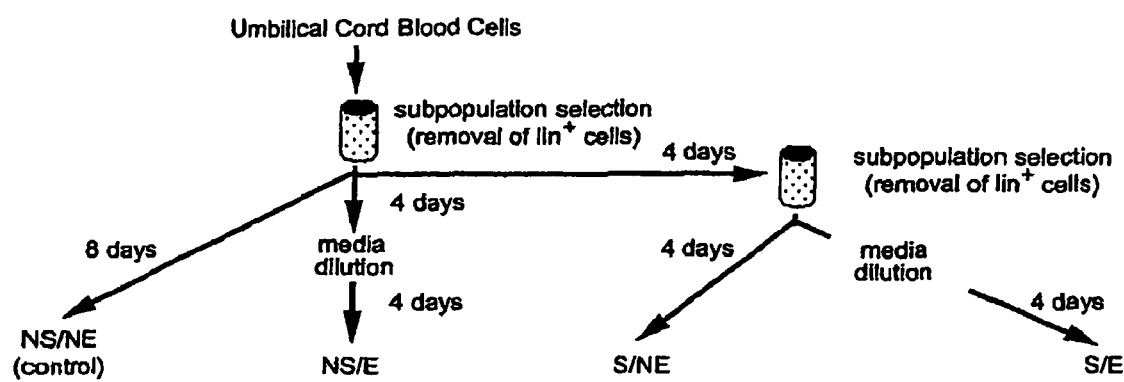
FIG. 12. is a schematic of the experimental protocol. The experimental design of all 4 test conditions is shown. Subpopulation selection and/or media dilution were performed on day 4 with all cultures allowed to incubate for a total of 8-days. Cultures were established with fresh UCB lin− cells in media containing TPO, SCF and FL. S: subpopulation selection; E: media dilution/exchange; NS: no selection; NE: no media dilution/exchange.

Global Culture Manipulation Selectively Targets the Expansion of Primitive Progenitor Cells To determine the role of GCM using subpopulation selection (S), no selection (NS), media dilution/exchange (E), no exchange (NE) or a combination thereof on HSC output, lin$^-$ UCB cells were subjected to 8-day cultures under four different conditions. In the first condition cells remained unmanipulated during the 8 day culture period (FIG. 12, NS/NE). For the second and third conditions, lin$^-$ cells were initially grown for 4-days and then subjected to either subpopulation selection (FIG. 12, S/NE) or media dilution (FIG. 12, NS/E) respectively. Subpopulation selection removed lin$^+$ cells (mature blood cells) generated during the first 4-days of culture. The fourth condition underwent both subpopulation selection and media dilution at day 4 (FIG. 12, S/E). At the end of the 8-day cultures, phenotypic and functional assays were performed to test the impact of GCM on the expansion of total cells, CD34$^+$ cells, CD34$^+$CD38$^-$ cells, CFCs and LTC-ICs. All cultures were grown in the same medium supplemented with the same growth factors (SCF, FL and TPO) in order to isolate the effects of the individual manipulation.

Figure 13:
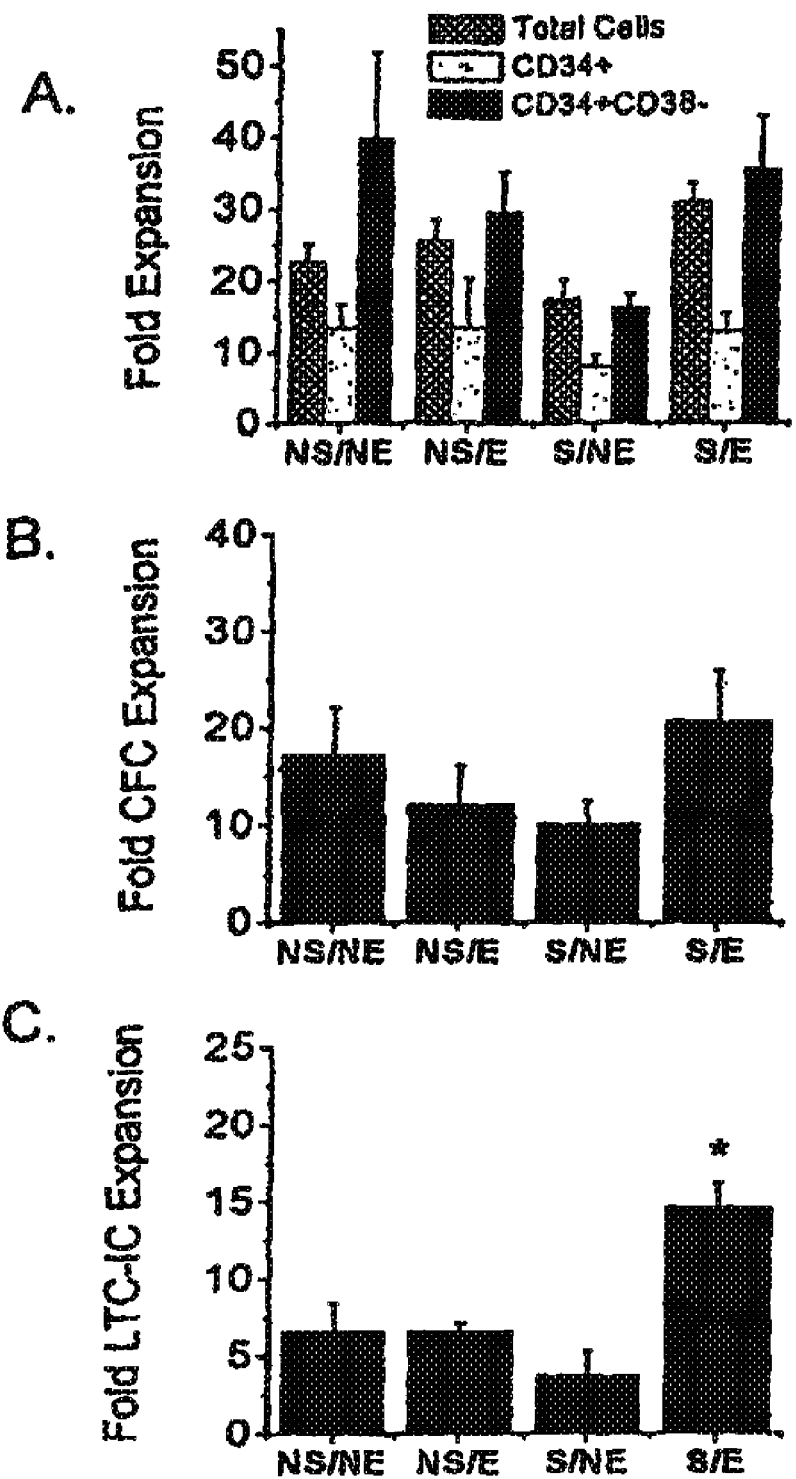
FIGS. 13A-C show the effects of subpopulation selection and media dilution on the expansion of hematopoietic progenitor cell populations. Purified UCB lin− cells ($1 \times 10^5$ cells/ml) were cultured for eight days using the four culture conditions indicated in FIG. 12. At the end of the eight day culture period, total cell (A) and progenitor cell (A, B, C) expansion was analyzed using phenotypic and in vitro functional assays. The fold expansion values shown are in comparison to fresh UCB lin− cells. (*) Represents significant difference (p<0.05) in comparison to unmanipulated control cultures (NS/NE).

Subpopulation selection, media dilution or a combination of both did not have a significant effect on the expansion of total cells, CD34$^+$ cells or CD34$^+$CD38$^-$ cells (FIG. 13a). CFC expansion was also statistically similar between the different culture conditions although there was a trend towards a higher expansion of CFCs under the S/E condition (FIG. 13b). In contrast, analysis of LTC-IC expansion results revealed synergistic effects of subpopulation selection and media dilution. The S/E condition yielded significantly (p<0.05) greater LTC-IC expansions (14.6±1.6 fold, relative to input) than unmanipulated control (NS/NE) cultures (6.6±1.8 fold) (FIG. 13c). Cultures undergoing only subpopulation selection or media dilution were statistically indistinguishable from control cultures indicating that parameters such as cytokine, glucose and/or metabolic byproduct depletion, all of which are known to inhibit overall cell proliferation, were unlikely to explain the differences in progenitor cell output. These findings demonstrate that GCM using subpopulation selection and media dilution preferentially target the growth of primitive cell types while having no effects on the production of mature progenitors.

Figure 14:
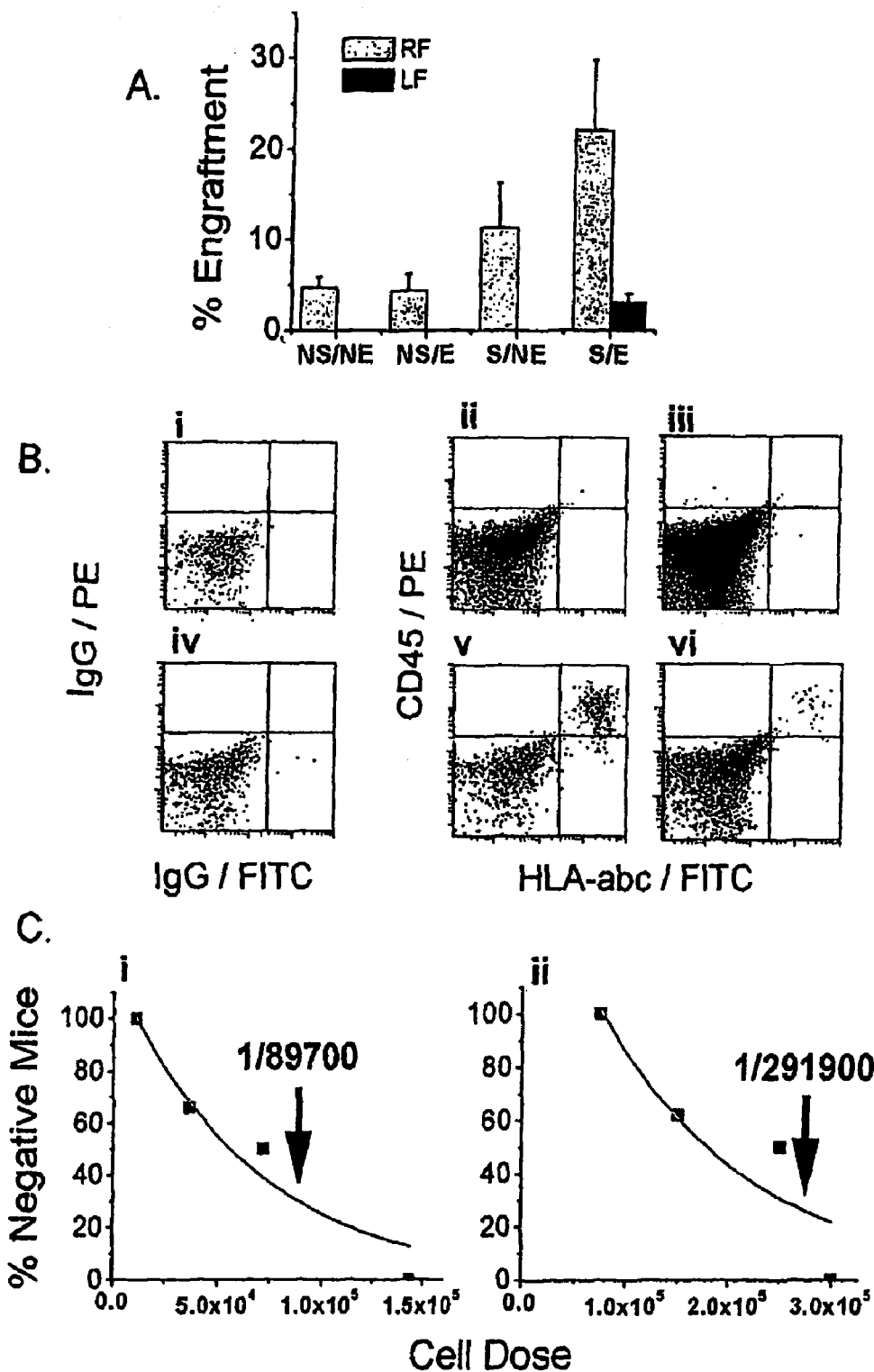
FIGS. 14A-C illustrate human cell engraftment in NOD/SCID mice following intrafemoral injection. These represent rapid SCID repopulating stem cells (R-SRCs) that may have enhanced clinical utility by allowing for "rapid engraftment" following transplantation. (A) A total of $3 \times 10^5$ cells, grown using the four culture conditions indicated, were injected intrafemorally into NOD/SCID mice. Examination of human cell engraftment in both the right and left femurs was assessed after two weeks. (B) A representative mouse, transplanted with cells from the S/E condition, showing engraftment in both the right femur (Bv) and left femur (Bvi) is represented along with a corresponding isotype control (Biv). Also shown is a non-engrafted control mouse that did not receive a transplant (isotype, Bi; right femur, Bii; left femur, Biii). (C) Limiting dilution analysis was performed to determine the frequency of migrating R-SRCs in fresh UCB lin−cells and cultured cells using the intrafemoral NOD/SCID assay. Engraftment frequencies for fresh UCB lin− (Ci) and expanded (Cii) cells are shown for each cell dose. The frequency of migrating R-SRCs was calculated using the maximum likelihood estimator with the overlayed curves representing results from these analyses. The calculated frequencies of R-SRCs are shown on the plots. Isotype controls were established for each sample.

Subpopulation Selection and Media Dilution Uniquely Expand R-SRCs with In Vivo Migratory Potential To determine the effect of GCM on the expansion of early blood progenitor cell developmental potential independent of effects on homing, we used, for the first time in expansion studies, the recently developed intrafemoral NOD/SCID assay[131,159]. In these studies, the progeny of lin⁻ cells, cultured under the four culture conditions, were injected directly into the right femur of mice. The size of each transplant was $3 \times 10^5$ cells per mouse for all conditions. After 2-weeks, examination of human cell engraftment in both the right and left femurs was assessed by flow cytometry. The data show that all culture conditions were able to produce cells with the capacity for rapid repopulation (i.e. 2-weeks) into the injected right femur (FIG. 14a). These R-SRCs can be considered, at a minimum, a short-term repopulating blood stem cell population, although previous use of the intrafemoral assay has shown that these cells also possess long-term engrafting ability[131]. Interestingly, higher engraftment levels of R-SRCs were measured in the injected right femur of mice receiving cells from the S/E condition with an average of 22.1±7.6% (range: 2.8 to 54.9) of the total BM cells collected consisting of human cells. Cells from the S/E group were also uniquely capable of human cell engraftment in the non-injected left femur [6 of 6 mice were engrafted with an average engraftment of 3.2±0.9% (range: 0.1 to 5.9); FIG. 14a, bvi]. This indicated that the transplanted cells were not only capable of engraftment but also migration into secondary bone sites. This migration of R-SRCs is an indicator of a highly primitive stem and progenitor cell population and thus suggests that the S/E condition generates cells with the functional capacities required for HSC transplantation (i.e. mobilization and tissue homing).

To quantify the expansion of R-SRCs capable of migrating from the injected right femur to the non-injected left femur, limiting dilution analysis was performed on this output. NOD/SCID mice received intrafemoral transplants, over a range of doses of either fresh (non-cultured) lin⁻ cells (n=28) or the progeny of cultured lin⁻ cells (n=46) undergoing both subpopulation selection and media dilution. The percentage of human cell engraftment as well as engraftment frequencies in the left femur were calculated for each cell dose. Only mice containing at least 0.1% human cell content were scored positive. Left femur engraftment from uncultured lin⁻ cells was observed using $1.4 \times 10^5$ (4/4 mice), $7.2 \times 10^4$ (2/4 mice) and $3.6 \times 10^4$ (1/4 mice) cells; no engraftment was observed when $1.3 \times 10^3$ to $1.1 \times 10^4$ cells were injected (0/16 mice; FIG. 14ci) When mice were transplanted with day 8 S/E expanded cells, engraftment was observed with $3.0 \times 10^5$ (6/6 mice), $2.5 \times 10^5$ (6/16 mice) and $1.5 \times 10^5$ (9/20 mice) cells (FIG. 14cii). No engraftment was detected using $7.5 \times 10^4$ cells (0/4 mice). Using the maximum likelihood estimator[133], the calculated frequencies of migrating R-SRCs in fresh lin⁻ cells and in the S/E expanded progeny were 1/89700 (95% confidence interval, 1/43500-1/217000) and 1/291900 (1/198200-1/452400) respectively. When coupled with total cell expansion values for these experiments, subpopulation selection and media dilution supported a 12.1-fold expansion of migrating R-SRCs above input values.

Global Culture Manipulations Result in the Expansion of LT-SRCs

Figure 15:
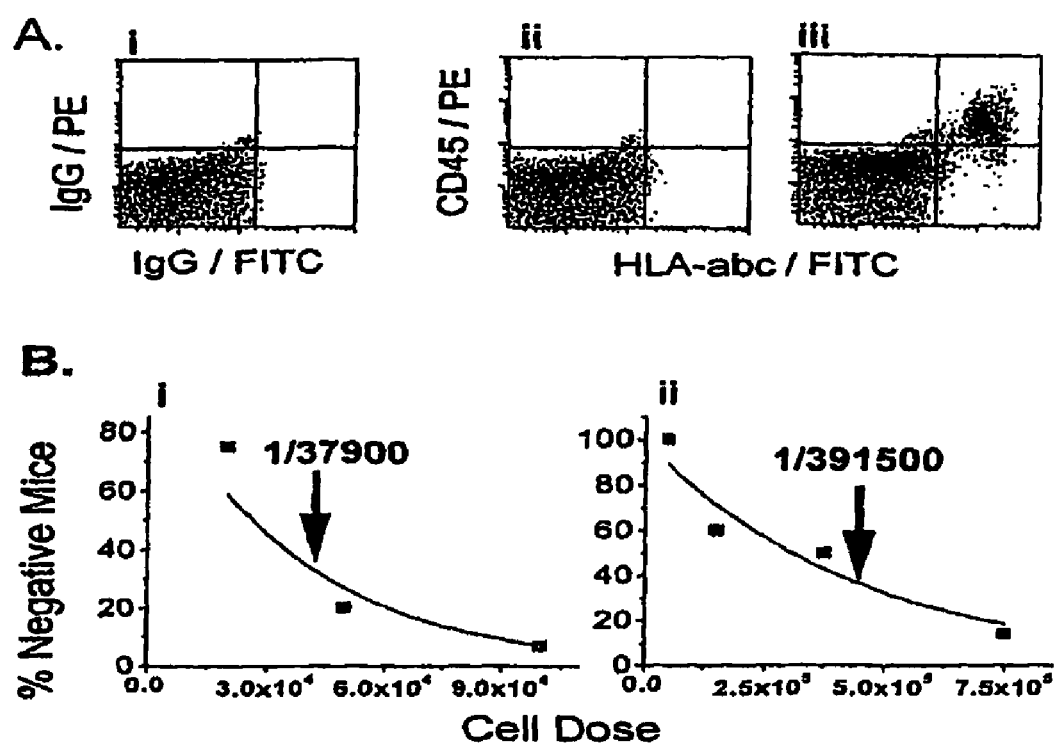
FIGS. 15A and 15B illustrate human cell engraftment in NOD/SCID mice following intravenous injection. (A) A typical flow cytometry plot showing the presence of human CD45$^+$HLA-abc$^+$ cells in intravenously injected NOD/SCID mice (Aiii). A control NOD/SCID mouse that did not receive cells is also shown (Aii) along with a representative isotype control (Ai). (B) Limiting dilution analysis was performed to determine the frequency of LT-SRCs present in fresh UCB lin$^-$ cells and expanded cells. The resultant engraftment frequencies for fresh lin$^-$ cells (Bi) and cultured cells (Bii) are shown for each cell dose and overlayed with curves representing results from the maximum likelihood estimator. Isotype controls were established for each sample.

In order to determine if subpopulation selection and media dilution resulted in significant expansions of LT-SRCs, limiting dilution analysis was performed on intravenously injected NOD/SCID mice using standard methods[71]. The mice received transplants of either fresh lin⁻ cells (n=24) or S/E cultured cells (n=25) and after 8-weeks were sacrificed and examined for the presence of human cells using flow cytometry (FIG. 15a). Engraftment was detected when $1.0 \times 10^5$ (14/15 mice), $5.0 \times 10^4$ (4/5 mice) and $2.0 \times 10^4$ (1/4 mice) fresh lin⁻ cells were transplanted (FIG. 15bi). Transplantation with S/E expanded cells resulted in a graft with cell doses of $7.5 \times 10^5$ (6/7 mice), $3.75 \times 10^5$ (4/7 mice) and $1.5 \times 10^5$ (3/7 mice) but not at $5.0 \times 10^4$ (0/4 mice) cells (FIG. 15bii). The frequency of LT-SRCs in fresh lin⁻ cells was found to be 1/37900 (1/22100-1/67000) while that in the expanded population was 1/391500 (1/226500-1/734800). By combining total cell expansion and these frequencies, the results indicate that after 8-days of culture the S/E condition was capable of delivering approximately 5.2-fold more LT-SRCs than input.

Cultured Cells Give Rise To Multilineage Differentiation In Vivo

To confirm that the engrafted cultured cells retained the capacity to differentiate into cells of both the lymphoid and myeloid lineages, the BM of engrafted NOD/SCID mice transplanted with S/E expanded cells were further analyzed using flow cytometry. Analysis of lineage markers, gated on the CD45⁺ (human) population of engrafted mice following intrafemoral injection, showed the presence of CD45⁺CD19⁺ lymphoid cells (FIG. 16aii) and CD45⁺CD33⁺ myeloid cells (FIG. 16aiii), indicating that these short-term repopulating cells have lymphomyeloid capacity. The reduced levels of B-cell engraftment is consistent with prior kinetic analysis showing the delayed engraftment at the two week time point. Similarly, cells introduced by intravenous injection and analyzed at week 8 also demonstrated both lymphoid (FIG. 16bii) and myeloid (FIG. 16biii) potential. Together these data indicate that the expanded cell population contains both short- and long-term repopulating human blood stem cells with the capacity for multilineage differentiation into mature blood cells.

The Secretion of Endogenously Produced Negative Regulators can be Controlled Using Global Culture Manipulations To determine the mechanism that underlies HSC expansion following GCM, we measured the secretion profiles of various known endogenously produced negative regulators using ELISA and semi-quantitative RT-PCR Analysis of unimanipulated cultures revealed that TGF-β1 and MIP-1α were expressed and secreted by cells during culture. Other inhibitory factors including tumor necrosis factor (TNF)-α, interleukin (IL)-3 and stromal derived factor (SDF)-1 were below the sensitivity of detection.

Figure 17:
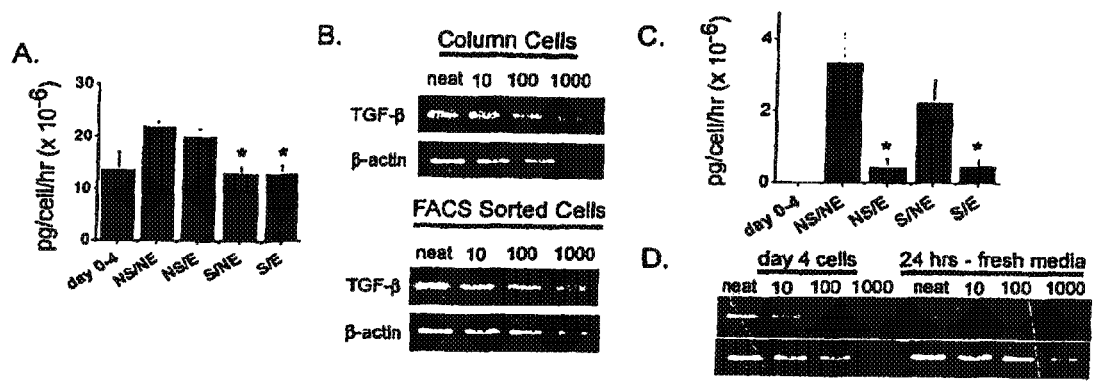
FIGS. 17A-D illustrate that the endogenous secretion of inhibitory factors is modulated by subpopulation selection and media dilution. (A) ELISA analysis showing changes in TGF-β1 secretion rates in response to subpopulation selection and/or media dilution. Conditions undergoing subpopulation selection resulted in significantly lower TGF-β1 production levels. (B) RT-PCR analysis showing that column isolated and FACS sorted lin$^+$ cells express TGFβ1. (C) ELISA analysis showing changes in MIP-1α secretion rates in response to subpopulation selection and/or media dilution. Media dilution significantly decreased the secretion of MIP-1α (D) Semi-quantitative RT-PCR analysis showing that MIP-1α steady state levels are decreased in response to fresh media. For all experiments, β-actin was used as a housekeeping gene. Serial dilutions (10-fold at each step) were done for all RT-PCR experiments as a means to quantify expression levels. Shown above the gel images are the corresponding fold-dilutions ('neat' denotes undiluted samples). For all dilutions tested, no genomic contamination was observed. (*) Represents significant difference ($p<0.05$) in comparison to unmanipulated control cultures (NS/NE).

The secretion rate (on a per cell basis) of TGF-β1 was found to be significantly lower in conditions that underwent subpopulation selection, regardless of whether media dilution was performed or not, resulting in an overall decrease in the concentration of TGF-β1 in culture supernatants (FIG. 17a). Control cultures (NS/NE condition) produced TGF-β1 at a rate of $21.8 \times 10^6 \pm 1.1 \times 10^6$ pg/cell/hr (bulk concentration: 2297±426 pg/ml) while cultures undergoing subpopulation selection alone (S/NE) or subpopulation selection and media dilution (S/E) resulted in values of $13.0 \times 10^6 \pm 1.4 \times 10^6$ (bulk concentration: 1528±167 pg/ml) and $13.0 \times 10^6 \pm 1.7 \times 10^6$ (bulk concentration: 1002±281 pg/ml) pg/cell/hr respectively. These findings show that subpopulation selection removes a population(s) of cells that secrete TGF-β1. Independently analyzed lin+ cells collected either directly from the selection column or by fluorescence activated cell sorting (FACS) were shown to express TGF-β1 mRNA and secrete TGF-β1 at detectable levels (FIG. 17b) confirming this finding.

In contrast, MIP-1α production was unaffected by subpopulation selection but was significantly impacted by media dilution. In control cultures, cultures undergoing media dilution alone (NS/E) and cultures undergoing media dilution plus subpopulation selection (S/E), MIP-1α was secreted at a rate of $3.3\times10^4 \pm 0.8\times10^{-6}$ (bulk concentration: 206±36 pg/ml), $0.5\times10^6 \pm 0.2\times10^6$ (bulk concentration: 70±30 pg/ml) and $0.5\times10^{-6} \pm 0.2\times10^{-6}$ (bulk concentration: 53±13 pg/ml) pg/cell/hr respectively (FIG. 17c). These findings indicated that the addition of fresh media resulted in either a decrease in MIP-1α transcript steady state levels and/or a downregulation of MIP-1α secretory mechanisms. Semi-quantitative RT-PCR of MIP-1α expression was performed on cells grown for 4-days, when media dilution was typically performed and when MIP-1α expression was known to be present, and on cells which were placed into fresh media for 24-hours. The expression of MIP-1α was found to be significantly lower in those cells which were placed in fresh media for 24 hours (FIG. 17d). These results suggest that the lower levels of MIP-1α production was due to the decreased steady state levels of MIP-1α gene expression in response to media dilution. The S/E condition, which had the highest expansion of LTC-ICs and uniquely resulted in short- and long-term blood stem cell expansion, was the only condition to have low production levels of both TGF-β1 and MIP-1α (FIGS. 17a and 17c). These findings suggest that a correlation may exist between the concentrations of inhibitory factors generated in culture and the expansion of primitive cell types in which lower concentrations result in higher expansions.

Endogenous production of negative regulators acts as a feedback control mechanism that limits HSC proliferation in vitro. There are two independent mechanisms by which these negative regulators can be produced: 1) secretion by differentiating cells (e.g., TGF-β1) and 2) stimulation of cells by culture conditioned media (e.g., MIP-1α). The GCM strategies (i.e. subpopulation selection and medium dilution) we devised were able to control the influence of these feedback mechanisms on HSCs resulting in expansions of both short- and long-term repopulating stem cells that had not been achievable previously. Our combination of these culture manipulations, as well as the elucidation of the mechanisms behind their beneficial effects to yield HSC expansion, provides a new strategy for in vitro stem cell culture that should be widely applicable.

The studies described herein are the first to quantitatively analyze HSC expansion based not only on repopulation but also on normal HSC trafficking/functioning following engraftment. Using the recently developed intrafemoral NOD/SCID assay[131], we were able to identify a (short-term) repopulating HSC with the capacity to migrate to secondary bone sites following engraftment. We further demonstrated that the expansion and maintenance of these cells could only be achieved when cells were exposed to both subpopulation selection and media dilution. Because these cells possess the ability to mobilize, migrate and home to BM microenvironments in vivo, and because it has been shown that systemic HSC trafficking is a requisite for normal HSC function[160], we concluded that these migrating cells may represent a more primitive cell population than those cells that are only capable of engrafting the transplant site. To our knowledge, this is the first reported use of this assay to quantify the expansion of stem cells that have this unique migratory ability.

These GCM strategies will enable elucidation of the true underlying responses of stem cells to supplemented cytokines and growth factors by reducing the convoluting effects of contaminating cell types. Our results lend insight into the apparent contradiction between the observation that many different cytokines, when tested for their effects on HSC self-renewal, have stimulatory effects over the first few stem cell divisions, but rapidly lead to stem cell differentiation as culture complexity develops[161]. Our results support the hypothesis that HSC self-renewal may be elicited using a variety of proliferation-inducing cytokines, but that the build up of relevant levels of negative regulators, which inhibit stem cell proliferation and/or induce differentiation, during in vitro culture ultimately limits stem cell growth.

Finally, gene expression and protein secretion analysis has convincingly shown that a variety of known negative regulators are expressed and secreted by different classes of differentiated blood cells[21,22,24,27,158], suggesting that the types of cells and cellular products that are generated during a typical expansion period may negatively influence current HSC culture systems. Previous work has shown that the neutralization of individual negative regulators including TGF-β, MIP-1α, SDF-1 and monocyte chemoattractant protein (MCP)-1 can initiate and support progenitor cell cycling and expansion in both in vitro and in vivo models[48-51]. Unfortunately, the use of such blocking schemes has not resulted in the expansion of the most primitive cell populations, including LT-SRCs[31] such as has been reported here. These findings suggest that, in normal expansion cultures, the production of a variety of negative regulators is responsible for inhibiting stem cell expansion, and that blocking only individual factors would not abrogate the effects of this mechanism. Therefore, the GCM strategy described may represent the most efficient methodology to overcome this problem because it targets the global production of both known and unknown negative regulators from targeted populations of cells. It is important to note that medium dilution strategies have been documented as important for progenitor cell maintenance[162], although the mechanism behind the observed effects have been predominantly attributed to metabolic byproduct regulation[163] and stromal-cell derived factor secretion[164]. Ongoing microarray studies designed to examine the global changes in gene expression of families of regulatory factors upon subpopulation selection and medium dilution (manipulations that can be independently controlled) provide a robust strategy to optimize this methodology, with respect to which cells to remove, timing of selection and media dilution frequency. This understanding represents an important step in the design of controlled expansion bioprocesses capable of producing clinically relevant quantities of functional blood stem cells for therapeutic applications.

Equivalents

From the foregoing detailed description of the specific embodiments of the invention, it should be apparent that a unique bioprocess apparatus and methods has been described. Although particular embodiments have been disclosed herein in detail, this has been done by way of example for purposes of illustration only, and is not intended to be limiting with respect to the scope of the appended claims which follow. For example, cell culture media and other culture conditions or selection of cells may be altered without departing from the inventive concepts described herein. In particular, it is contemplated by the inventor that various substitutions, alterations, and modifications may be made to the invention without departing from the spirit and scope of the invention as defined by the claims.

BIBLIOGRAPHY

The contents of references cited throughout this document and in this bibliography, are hereby incorporated herein by reference in their entireties.

1. Barnett, M. J., Eaves, C. J., Phillips, G. L., Gascoyne, R. D., Hogge, D. E., Horsman, D. E., Humphries, R. K., Klingemann, H. G., Lansdorp, P. M., Nantel, S. H. & et al. Autografting with cultured marrow in chronic myeloid leukemia: results of a pilot study. *Blood* 84, 724-32 (1994).
2. Bertolini, F., Battaglia, M., Pedrazzoli, P., Da Prada, G. A., Lanza, A., Soligo, D., Caneva, L., Sarina, B., Murphy, S., Thomas, T. & della Cuna, G. R. Megakaryocytic progenitors can be generated ex vivo and safely administered to autologous peripheral blood progenitor cell transplant recipients. *Blood* 89, 2679-88 (1997).
3. Brugger, W., Heimfeld, S., Berenson, R. J., Mertelsmann, R. & Kanz, L. Reconstitution of hematopoiesis after high-dose chemotherapy by autologous progenitor cells generated ex vivo. *N Engl J Med* 333, 283-7 (1995).
4. Williams, S. F., Lee, W. J., Bender, J. G., Zimmerman, T., Swinney, P., Blake, M., Carreon, J., Schilling, M., Smith, S., Williams, D. E., Oldham, F. & Van Epps, D. Selection and expansion of peripheral blood CD34+ cells in autologous stem cell transplantation for breast cancer. *Blood* 87, 1687-91 (1996).
5. Williams, D. A. Ex vivo expansion of hematopoietic stem and progenitor cells-robbing Peter to pay Paul? *Blood* 81, 3169-72 (1993).
6. Gan, O. I., Murdoch, B., Larochelle, A. & Dick, J. E. Differential maintenance of primitive human SCID-repopulating cells, clonogenic progenitors, and long-term culture-initiating cells after incubation on human bone marrow stromal cells. *Blood* 90, 641-50 (1997).
7. Bhatia, M., Wang, J. C., Kapp, U., Bonnet, D. & Dick, J. E. Purification of primitive human hematopoietic cells capable of repopulating immune-deficient mice. *Proc Natl Acad Sci USA* 94, 5320-5. (1997).
8. Ueda, T., Tsuji, K., Yoshino, H., Ebihara, Y., Yagasaki, H., Hisakawa, H., Mitsui, T., Manabe, A., Tanaka, R., Kobayashi, K., Ito, M., Yasukawa, K. & Nakahata, T. Expansion of human NOD/SCID-repopulating cells by stem cell factor, Flk2/Flt3 ligand, thrombopoietin, IL-6, and soluble IL-6 receptor [see comments]. *J Clin Invest* 105, 1013-21 (2000).
9. McNiece, I. K., Almeida-Porada, G., Shpall, E. J. & Zanjani, E. Ex vivo expanded cord blood cells provide rapid engraftment in fetal sheep but lack long-term engrafting potential. *Exp Hematol* 30, 612-6 (2002).
10. Conneally, E., Cashman, J., Petzer, A. & Eaves, C. Expansion in vitro of transplantable human cord blood stem cells demonstrated using a quantitative assay of their lympho-myeloid repopulating activity in nonobese diabetic-scid/scid mice. *Proc Natl Acad Sci USA* 94, 9836-41 (1997).
11. Glimm, H. & Eaves, C. J. Direct evidence for multiple self-renewal divisions of human in vivo repopulating hematopoietic cells in short-term culture. *Blood* 94, 2161-8 (1999).
12. Denning-Kendall, P. A., Evely, R., Singha, S., Chapman, M., Bradley, B. A. & Hows, J. M. In vitro expansion of cord blood does not prevent engraftment of severe combined immunodeficient repopulating cells. *Br J Haematol* 116, 218-28 (2002).
13. Dick, J. E., Magli, M. C., Huszar, D., Phillips, R. A. & Bernstein, A. Introduction of a selectable gene into primitive stem cells capable of long-term reconstitution of the hemopoietic system of W/Wv mice. *Cell* 42, 71-9. (1985).
14. Osawa, M., Hanada, K., Hamada, H. & Nakauchi, H. Long-term lymphohematopoietic reconstitution by a single CD34-low/negative hematopoietic stem cell. *Science* 273, 242-5. (1996).
15. Szilvassy, S. J., Humphries, R. K., Lansdorp, P. M., Eaves, A. C. & Eaves, C. J. Quantitative assay for totipotent reconstituting hematopoietic stem cells by a competitive repopulation strategy. *Proc Natl Acad Sci USA* 87, 8736-40. (1990).
16. Guenechea, G., Gan, O. I., Dorrell, C. & Dick, J. E. Distinct classes of human stem cells that differ in proliferative and self-renewal potential. *Nat Immunol* 2, 75-82. (2001).
17. Keller, G. & Snodgrass, R. Life span of multipotential hematopoietic stem cells in vivo. *J Exp Med* 171, 1407-18. (1990).
18. Lemischka, I. R., Raulet, D. H. & Mulligan, R. C. Developmental potential and dynamic behavior of hematopoietic stem cells. *Cell* 45, 917-27. (1986).
19. Pawliuk, R., Eaves, C. & Humphries, R. K. Evidence of both ontogeny and transplant dose-regulated expansion of hematopoietic stem cells in vivo. *Blood* 88, 2852-8 (1996).
20. Iscove, N. N. & Nawa, K. Hematopoietic stem cells expand during serial transplantation in vivo without apparent exhaustion. *Curr Biol* 7, 805-8 (1997).
21. Grotendorst, G. R., Smale, G. & Pencev, D. Production of transforming growth factor beta by human peripheral blood monocytes and neutrophils. *J Cell Physiol* 140, 396-402 (1989).
22. Cluitmans, F. H., Esendam, B. H., Landegent, J. E., Willemze, R. & Falkenburg, J. H. Constitutive in vivo cytokine and hematopoietic growth factor gene expression in the bone marrow and peripheral blood of healthy individuals. *Blood* 85, 2038-44 (1995).
23. Wickenhauser, C., Lorenzen, J., Thiele, J., Hillienhof, A., Jungheim, K., Schmitz, B., Hansmann, M. L. & Fischer, R. Secretion of cytokines (interleukins-1 alpha, -3, and -6 and granulocyte-macrophage colony-stimulating factor) by normal human bone marrow megakaryocytes. *Blood* 85, 685-91 (1995).
24. Sautois, B., Fillet, G. & Beguin, Y. Comparative cytokine production by in vitro stimulated mononucleated cells from cord blood and adult blood. *Exp Hematol* 25, 103-8 (1997).
25. Scapini, P., Lapinet-Vera, J. A., Gasperini, S., Calzetti, F., Bazzoni, F. & Cassatella, M. A. The neutrophil as a cellular source of chemokines. *Immunol Rev* 177, 195-203 (2000).
26. Phillips, R. L., Ernst, R. E., Brunlc, B., Ivanova, N., Mahan, M. A., Deanehan, J. K., Moore, K. A., Overton, G. C. & Lemischka, I. R. The genetic program of hematopoietic stem cells. *Science* 288, 1635-40. (2000).
27. Majka, M., Janowska-Wieczorek, A., Ratajczak, J., Ehrenman, K., Pietrzkowski, Z., Kowalska, M. A., Gewirtz, A. M., Emerson, S. G. & Ratajczak, M. Z. Numerous growth factors, cytokines, and chemokines are secreted by human CD34(+) cells, myeloblasts, erythroblasts, and megakaryoblasts and regulate normal hematopoiesis in an autocrine/paracrine manner. *Blood* 97, 3075-3085. (2001).
28. Hariharan, D., Ho, W., Cutilli, J., Campbell, D. E. & Douglas, S. D. C—C chemokine profile of cord blood mononuclear cells: selective defect in RANTES production. *Blood* 95, 715-8 (2000).
29. Hornung, F., Scala, G. & Lenardo, M. J. TNF-alpha-induced secretion of C—C chemokines modulates C—C chemokine receptor 5 expression on peripheral blood lymphocytes. *J Immunol* 164, 6180-7 (2000).

30. Bluman, E. M., Bartynski, K. J., Avalos, B. R. & Caligiuri, M. A. Human natural killer cells produce abundant macrophage inflammatory protein-1 alpha in response to monocyte-derived cytokines. *J Clin Invest* 97, 2722-7 (1996).
31. Dao, M. A., Hwa, J. & Nolta, J. A. Molecular mechanism of transforming growth factor beta-mediated cell-cycle modulation in primary human CD34(+) progenitors. *Blood* 99, 499-506 (2002).
32. Fortunel, N. O., Hatzfeld, J. A., Monier, M. N. & Hatzfeld, A. Control of hematopoietic stem/progenitor cell fate by transforming growth factor-beta. *Oncol Res* 13, 445-53 (2003).
33. Broxmeyer, H. E., Sherry, B., Cooper, S., Lu, L., Maze, R., Beckmann, M. P., Cerami, A. & Ralph, P. Comparative analysis of the human macrophage inflammatory protein family of cytokines (chemokines) on proliferation of human myeloid progenitor cells. Interacting effects involving suppression, synergistic suppression, and blocking of suppression. *J Immunol* 150, 3448-58 (1993).
34. Veiby, O. P., Jacobsen, F. W., Cui, L., Lyman, S. D. & Jacobsen, S. E. The flt3 ligand promotes the survival of primitive hemopoietic progenitor cells with myeloid as well as B lymphoid potential. Suppression of apoptosis and counteraction by TNF-alpha and TGF-beta. *J Immunol* 157, 2953-60. (1996).
35. Yonemura, Y., Ku, H., Hirayama, F., Souza, L. M. & Ogawa, M. Interleukin 3 or interleukin 1 abrogates the reconstituting ability of hematopoietic stem cells. *Proc Natl Acad Sci USA* 93, 4040-4 (1996).
36. Elliott, M. J., Moss, J., Dottore, M., Park, L. S., Vadas, M. A. & Lopez, A. F. Differential binding of IL-3 and GM-CSF to human monocytes. *Growth Factors* 6, 15-29 (1992).
37. Fukuda, T., Kamishima, T., Tsuura, Y., Suzuki, T., Kakihara, T., Naito, M., Kishi, K., Matsumoto, K., Shibata, A. & Seito, T. Expression of the c-kit gene product in normal and neoplastic mast cells but not in neoplastic basophil/mast cell precursors from chronic myelogenous leukaemia. *J Pathol* 177, 139-46 (1995).
38. Lyman, S. D. & Jacobsen, S. E. c-kit ligand and Flt3 ligand: stem/progenitor cell factors with overlapping yet distinct activities. *Blood* 91, 1101-34. (1998).
39. Metcalf, D. & Nicola, N. A. Direct proliferative actions of stem cell factor on murine bone marrow cells in vitro: effects of combination with colony-stimulating factors. *Proc Natl Acad Sci USA* 88, 6239-43 (1991).
40. Rappold, I., Ziegler, B. L., Kohler, I., Marchetto, S., Rosnet, O., Birnbaum, D., Simmons, P. J., Zannettino, A. C., Hill, B., Neu, S., Knapp, W., Alitalo, R., Alitalo, K., Ullrich, A., Kanz, L. & Buhring, H. J. Functional and phenotypic characterization of cord blood and bone marrow subsets expressing FLT3 (CD135) receptor tyrosine kinase. *Blood* 90, 111-25 (1997).
41. Methia, N., Louache, F., Vainchenker, W. & Wendling, F. Oligodeoxynucleotides antisense to the proto-oncogene c-mpl specifically inhibit in vitro megakaryocytopoiesis. *Blood* 82, 1395-401 (1993).
42. Sato, N., Caux, C., Kitamura, T., Watanabe, Y., Arai, K., Banchereau, J. & Miyajima, A. Expression and factor-dependent modulation of the interleukin-3 receptor subunits on human hematopoietic cells. *Blood* 82, 752-61 (1993).
43. Wognum, A. W., de Jong, M. O. & Wagemaker, G. Differential expression of receptors for hemopoietic growth factors on subsets of CD34+ hemopoietic cells. *Leuk Lymphoma* 24, 11-25 (1996).
44. Debili, N., Masse, J. M., Katz, A., Guichard, J., Breton-Gorius, J. & Vainchenker, W. Effects of the recombinant hematopoietic growth factors interleukin-3, interleukin-6, stem cell factor, and leukemia inhibitory factor on the megakaryocytic differentiation of CD34+ cells. *Blood* 82, 84-95 (1993).
45. Grossi, A., Vannucchi, A. M., Bacci, P., Longo, G., Rafanelli, D., Alterini, R. & Rossi Ferrini, P. In vivo administration of stem cell factor enhances both proliferation and maturation of murine megakaryocytes. *Haematologica* 80, 18-24 (1995).
46. Lindemann, A., Herrmann, F., Oster, W., Haffner, G., Meyenburg, W., Souza, L. M. & Mertelsmann, R. Hematologic effects of recombinant human granulocyte colony-stimulating factor in patients with malignancy. *Blood* 74, 2644-51 (1989).
47. Metcalf, D. Control of granulocytes and macrophages: molecular, cellular, and clinical aspects. *Science* 254, 529-33 (1991).
48. Cashman, J. D., Clark-Lewis, I., Eaves, A. C. & Eaves, C. J. Differentiation stage-specific regulation of primitive human hematopoietic progenitor cycling by exogenous and endogenous inhibitors in an in vivo model. *Blood* 94, 3722-9 (1999).
49. Dao, M. A., Taylor, N. & Nolta, J. A. Reduction in levels of the cyclin-dependent kinase inhibitor p27(kip-1) coupled with transforming growth factor beta neutralization induces cell-cycle entry and increases retroviral transduction of primitive human hematopoietic cells. Proc *Natl Acad Sci USA* 95, 13006-11 (1998).
50. Eaves, C. J., Cashman, J. D., Kay, R. J., Dougherty, G. J., Otsuka, T., Gaboury, L. A., Hogge, D. E., Lansdorp, P. M., Eaves, A. C. & Humphries, R. K. Mechanisms that regulate the cell cycle status of very primitive hematopoietic cells in long-term human marrow cultures. II. Analysis of positive and negative regulators produced by stromal cells within the adherent layer. *Blood* 78, 110-7 (1991).
51. Batard, P., Monier, M. N., Fortunel, N., Ducos, K., Sansilvestri-Morel, P., Phan, T., Hatzfeld, A. & Hatzfeld, J. A. TGF-(beta)1 maintains hematopoietic immaturity by a reversible negative control of cell cycle and induces CD34 antigen up-modulation. *J Cell Sci* 113, 383-90 (2000).
52. Cashman, J. D., Eaves, C. J., Sarris, A. H. & Eaves, A. C. MCP-1, not MIP-1 alpha, is the endogenous chemokine that cooperates with TGF-beta to inhibit the cycling of primitive normal but not leukemic (CML) progenitors in long-term human marrow cultures. *Blood* 92, 2338-44. (1998).
53. Guba, S. C., Sartor, C. I., Gottschalk, L. R., Jing, Y. H., Mulligan, T. & Emerson, S. G. Bone marrow stromal fibroblasts secrete interleukin-6 and granulocyte-macrophage colony-stimulating factor in the absence of inflammatory stimulation: demonstration by serum-free bioassay, enzyme-linked immunosorbent assay, and reverse transcriptase polymerase chain reaction. *Blood* 80, 1190-8 (1992).
54. Cashman, J., Clark-Lewis, I., Eaves, A. & Eaves, C. Stromal-derived factor 1 inhibits the cycling of very primitive human hematopoietic cells in vitro and in NOD/SCID mice. *Blood* 99, 792-9 (2002).
55. Fortunel, N., Hatzfeld, J., Kisselev, S., Monier, M. N., Ducos, K., Cardoso, A., Batard, P. & Hatzfeld, A. Release from quiescence of primitive human hematopoietic stem/progenitor cells by blocking their cell-surface TGF-beta type II receptor in a short-term in vitro assay. *Stem Cells* 18, 102-11 (2000).

56. Madlambayan, G. J., Rogers, I., Casper, R. F. & Zandstra, P. W. Manipulation of endogenous factor production enables in vitro stem and progenitor cell expansion: effects of cell selection and medium supplementation. *Blood* 100, 643a (2002).

57. Sutherland, H. J., Eaves, C. J., Eaves, A. C., Dragowska, W. & Lansdorp, P. M. Characterization and partial purification of human marrow cells capable of initiating long-term hematopoiesis in vitro. *Blood* 74, 1563-70 (1989).

58. Sutherland, H. J., Lansdorp, P. M., Henkelman, D. H., Eaves, A. C. & Eaves, C. J. Functional characterization of individual human hematopoietic stem cells cultured at limiting dilution on supportive marrow stromal layers. *Proc Natl Acad Sci USA* 87, 3584-8 (1990).

59. Sutherland, H. J., Eaves, C. J., Lansdorp, P. M., Thacker, J. D. & Hogge, D. E. Differential regulation of primitive human hematopoietic cells in long-term cultures maintained on genetically engineered murine stromal cells. *Blood* 78, 666-72 (1991).

60. Hogge, D. E., Lansdorp, P. M., Reid, D., Gerhard, B. & Eaves, C. J. Enhanced detection, maintenance, and differentiation of primitive human hematopoietic cells in cultures containing murine fibroblasts engineered to produce human steel factor, interleukin-3, and granulocyte colony-stimulating factor. *Blood* 88, 3765-73. (1996).

61. Till, J. E. & Mc, C. E. A direct measurement of the radiation sensitivity of normal mouse bone marrow cells. *Radiat Res* 14, 213-22 (1961).

62. Horn, P. A., Thomasson, B. M., Wood, B. L., Andrews, R. G., Morris, J. C. & Kiem, H. P. Distinct hematopoietic stem/progenitor cell populations are responsible for repopulating NOD/SCID mice compared with nonhuman primates. *Blood* 102, 4329-35 (2003).

63. Nolta, J. A., Hanley, M. B. & Kohn, D. B. Sustained human hematopoiesis in immunodeficient mice by cotransplantation of marrow stroma expressing human interleukin-3: analysis of gene transduction of long-lived progenitors. *Blood* 83, 3041-51 (1994).

64. McCune, J. M., Namikawa, .R., Kaneshima, H., Shultz, L. D., Lieberman, M. & Weissman, I. L. The SCID-hu mouse: murine model for the analysis of human hematolymphoid differentiation and function. *Science* 241, 1632-9 (1988).

65. Zanjani, E. D. The human sheep xenograft model for the study of the in vivo potential of human HSC and in utero gene transfer. *Stem Cells* 18, 151 (2000).

66. Lapidot, T., Pflumio, F., Doedens, M., Murdoch, B., Williams, D. E. & Dick, J. E. Cytokine stimulation of multilineage hematopoiesis from immature human cells engrafted in SCID mice. *Science* 255, 1137-41 (1992).

67. Kamel-Reid, S. & Dick, J. E. Engraftment of immune-deficient mice with human hematopoietic stem cells. *Science* 242, 1706-9. (1988).

68. Dick, J. E. Normal and leukemic human stem cells assayed in SCID mice. *Semin Immunol* 8, 197-206 (1996).

69. Hogan, C. J., Shpall, E. J., McNulty, O., McNiece, I., Dick, J. E., Shultz, L. D. & Keller, G. Engraftment and development of human CD34(+)-enriched cells from umbilical cord blood in NOD/LtSz-scid/scid mice. *Blood* 90, 85-96 (1997).

70. Cashman, J. D., Lapidot, T., Wang, J. C., Doedens, M., Shultz, L. D., Lansdorp, P., Dick, J. E. & Eaves, C. J. Kinetic evidence of the regeneration of multilineage hematopoiesis from primitive cells in normal human bone marrow transplanted into immunodeficient mice. *Blood* 89, 4307-16 (1997).

71. Wang, J. C., Doedens, M. & Dick, J. E. Primitive human hematopoietic cells are enriched in cord blood compared with adult bone marrow or mobilized peripheral blood as measured by the quantitative in vivo SCID-repopulating cell assay. *Blood* 89, 3919-24 (1997).

72. Krause, D. S., Fackler, M. J., Civin, C. I. & May, W. S. CD34: structure, biology, and clinical utility. *Blood* 87, 1-13. (1996).

73. Sauvageau, G., Lansdorp, P. M., Eaves, C. J., Hogge, D. E., Dragowska, W. H., Reid, D. S., Largman, C., Lawrence, H. J. & Humphries, R. K. Differential expression of homeobox genes in functionally distinct CD34+ subpopulations of human bone marrow cells. *Proc Natl Acad Sci USA* 91, 12223-7 (1994).

74. Goodell, M. A., Brose, K., Paradis, G., Conner, A. S. & Mulligan, R. C. Isolation and functional properties of murine hematopoietic stem cells that are replicating in vivo. *J Exp Med* 183, 1797-806 (1996).

75. Goodell, M. A., Rosenzweig, M., Kim, H., Marks, D. F., DeMaria, M., Paradis, G., Grupp, S. A., Sieff, C. A., Mulligan, R. C. & Johnson, R. P. Dye efflux studies suggest that hematopoietic stem cells expressing low or undetectable levels of CD34 antigen exist in multiple species. *Nat Med* 3, 1337-45 (1997).

76. Bhatia, M., Bonnet, D., Murdoch, B., Gan, O. I. & Dick, J. E. A newly discovered class of human hematopoietic cells with SCID-repopulating activity [see comments]. *Nat Med* 4, 1038-45 (1998).

77. Zanjani, E. D., Almeida-Porada, G., Livingston, A. G., Flake, A. W. & Ogawa, M. Human bone marrow CD34- cells engraft in vivo and undergo multilineage expression that includes giving rise to CD34+ cells. *Exp Hematol* 26, 353-60 (1998).

78. Baum, C. M., Weissman, I. L., Tsukamoto, A. S., Buckle, A. M. & Peault, B. Isolation of a candidate human hematopoietic stem-cell population. *Proc Natl Acad Sci USA* 89, 2804-8. (1992).

79. Craig, W., Kay, R., Cutler, R. L. & Lansdorp, P. M. Expression of Thy-1 on human hematopoietic progenitor cells. *J Exp Med* 177, 1331-42. (1993).

80. Uchida, N., Aguila, H. L., Fleming, W. H., Jerabek, L. & Weissman, I. L. Rapid and sustained hematopoietic recovery in lethally irradiated mice transplanted with purified Thy-1.1lo Lin-Sca-1+ hematopoietic stem cells. *Blood* 83, 3758-79 (1994).

81. Pasino, M., Lanza, T., Marotta, F., Scarso, L., De Biasio, P., Amato, S., Corcione, A., Pistoia, V. & Mori, P. G. Flow cytometric and functional characterization of AC133+ cells from human umbilical cord blood. *Br J Haematol* 108, 793-800. (2000).

82. Goussetis, E., Theodosaki, M., Paterakis, G., Peristeri, J., Petropoulos, D., Kitra, V., Papassarandis, C. & Graphakos, S. A functional hierarchy among the CD34+ hematopoietic cells based on in vitro proliferative and differentiative potential of AC133+CD34(bright) and AC133(dim/)-CD34+ human cord blood cells. *J Hematother Stem Cell Res* 9, 827-40. (2000).

83. Handgretinger, R., Gordon, P. R., Leimig, T., Chen, X., Buhring, H. J., Niethammer, D. & Kuci, S. Biology and plasticity of CD133+hematopoietic stem cells. *Ann N Y Acad Sci* 996; 141-51 (2003).

84. de Wynter, E. A., Buck, D., Hart, C., Heywood, R., Coutinho, L. H., Clayton, A., Rafferty, J. A., Burt, D., Guenechea, G., Bueren, J. A., Gagen, D., Fairbairn, L. J., Lord, B. I. & Testa, N. G. CD34+AC133+ cells isolated from cord blood are highly enriched in long-term culture-initiating cells, NOD/SCID-repopulating cells and dendritic cell progenitors. *Stem Cells* 16, 387-96 (1998).

85. Ziegler, B. L., Valtieri, M., Porada, G. A., De Maria, R., Muller, R., Masella, B., Gabbianelli, M., Casella, I., Pelosi, E., Bock, T., Zanjani, E. D. & Peschle, C. KDR receptor: a key marker defining hematopoietic stem cells. *Science* 285, 1553-8 (1999).

86. Srour, E. F., Brandt, J. E., Briddell, R. A., Leemhuis, T., van Besien, K. & Hoffman, R. Human CD34+ HLA-DR- bone marrow cells contain progenitor cells capable of self-renewal, multilineage differentiation, and long-term in vitro hematopoiesis. *Blood Cells* 17, 287-95 (1991).

87. Mayani, H. & Lansdorp, P. M. Proliferation of individual hematopoietic progenitors purified from umbilical cord blood. *Exp Hematol* 23, 1453-62 (1995).

88. Audet, J., Zandstra, P. W., Eaves, C. J. & Piret, J. M. Advances in hematopoietic stem cell culture. *Curr Opin Biotechnol* 9, 146-51 (1998).

89. Ihle, J. N. Cytokine receptor signalling. *Nature* 377, 591-4 (1995).

90. Haylock, D. N., Horsfall, M. L., Ramshaw, H. S., Niutta, S., Protopsaltis, S., Peng, L., Burrell, C., Rappold, I., Buhring, H. J. & Simmons, P. J. Increased recruitment of hematopoietic progenitor cells underlies the ex vivo expansion potential of FLT3 ligand. *Blood* 90, 2260-72. (1997).

91. Broudy, V. C. Stem cell factor and hematopoiesis. *Blood* 90, 1345-64. (1997).

92. Kimura, T., Wang, J., Minamiguchi, H., Fujiki, H., Harada, S., Okuda, K., Kaneko, H., Yokota, S., Yasukawa, K., Abe, T. & Sonoda, Y. Signal through gp130 activated by soluble interleukin (IL)-6 receptor (R) and IL-6 or IL-6R/IL-6 fusion protein enhances ex vivo expansion of human peripheral blood-derived hematopoietic progenitors. *Stem Cells* 18, 444-52 (2000).

93. Yagi, M., Ritchie, K. A., Sitnicka, E., Storey, C., Roth, G. J. & Bartehnez, S. Sustained ex vivo expansion of hematopoietic stem cells mediated by thrombopoietin. *Proc Natl Acad Sci USA* 96, 8126-31 (1999).

94. Ikebuchi, K., Wong, G. G., Clark, S. C., Ihle, J. N., Hirai, Y. & Ogawa, M. Interleukin 6 enhancement of interleukin 3-dependent proliferation of multipotential hemopoietic progenitors. *Proc Natl Acad Sci USA* 84, 9035-9 (1987).

95. Neben, S., Donaldson, D., Sieff, C., Mauch, P., Bodine, D., Ferrara, J., Yetz-Aldape, J. & Turner, K. Synergistic effects of interleukin-11 with other growth factors on the expansion of murine hematopoietic progenitors and maintenance of stem cells in liquid culture. *Exp Hematol* 22, 353-9 (1994).

96. Ikebuchi, K., Clark, S. C., Ihle, J. N., Souza, L. M. & Ogawa, M. Granulocyte colony-stimulating factor enhances interleukin 3-dependent proliferation of multipotential hemopoietic progenitors. *Proc Natl Acad Sci USA* 85, 3445-9 (1988).

97. Hirayama, F., Katayama, N., Neben, S., Donaldson, D., Nickbarg, E. B., Clark S. C. & Ogawa, M. Synergistic interaction between interleukin-12 and steel factor in support of proliferation of murine lymphohematopoietic progenitors in culture. *Blood* 83, 92-8 (1994).

98. Bagby, G. C., Jr. Interleukin-1 and hematopoiesis. *Blood Rev* 3, 152-61 (1989).

99. Metcalf, D., Burgess, A. W., Johnson, G. R., Nicola, N. A., Nice, E. C., DeLamarter, J., Thatcher, D. R & Mermod, J. J. In vitro actions on hemopoietic cells of recombinant murine GM-CSF purified after production in *Escherichia coli*: comparison with purified native GM-CSF. *J Cell Physiol* 128, 421-31 (1986).

100. Ramsfjell, V., Borge, O. J., Cui, L. & Jacobsen, S. E. Thrombopoietin directly and potently stimulates multilineage growth and progenitor cell expansion from primitive (CD34+ CD38−) human bone marrow progenitor cells: distinct and key interactions with the ligands for c-kit and flt3, and inhibitory effects of TGF-beta and TNF-alpha. *J Immunol* 158, 5169-77 (1997).

101. Shapiro, F., Pytowski, B., Rafii, S., Witte, L., Hicklin, D. J., Yao, T. J. & Moore, M. A. The effects of Flk-2/flt3 ligand as compared with c-kit ligand on short-term and long-term proliferation of CD34+ hematopoietic progenitors elicited from human fetal liver, umbilical cord blood, bone marrow, and mobilized peripheral blood. *J Hematother* 5, 655-62 (1996).

102. Haylock, D. N., To, L. B., Dowse, T. L., Juttner, C. A. & Simmons, P. J. Ex vivo expansion and maturation of peripheral blood CD34+ cells into the myeloid lineage. *Blood* 80, 1405-12 (1992).

103. Sitnicka, E., Ruscetti, F. W., Priestley, G. V., Wolf, N. S. & Bartelmez, S. H. Transforming growth factor beta 1 directly and reversibly inhibits the initial cell 4 divisions of long-term repopulating hematopoietic stem cells. *Blood* 88, 82-8 (1996).

104. Jacobsen, S. E., Keller, J. R., Rusceffi, F. W., Kondaiah, P., Roberts, A. B. & Falk, L. A. Bidirectional effects of transforming growth factor beta (TGF-beta) on colony-stimulating factor-induced human myelopoiesis in vitro: differential effects of distinct TGF-beta isoforms. *Blood* 78, 2239-47 (1991).

105. Ottanin, O. G. & Pelus, L. M. Differential proliferative effects of transforming growth factor-beta on human hematopoietic progenitor cells. *J Immunol* 140, 2661-5 (1988).

106. Van Ranst, P. C., Snoeck, H. W., Lardon, F., Lenjou, M., Nijs, G., Weekx, S. F., Rodrigus, I., Berneman, Z. N. & Van Bockstaele, D. R TGF-beta and MIP-1 alpha exert their main inhibitory activity on very primitive CD34+2CD38− cells but show opposite effects on more mature CD34+ CD38+ human hematopoietic progenitors. *Exp Hematol* 24, 1509-15 (1996).

107. Fortunel, N. O., Hatzfeld, A. & Hatzfeld, J. A. Transforming growth factor-beta: pleiotropic role in the regulation of hematopoiesis. *Blood* 96, 2022-36 (2000).

108. Heinrich, M. C., Dooley, D. C. & Keeble, W. W. Transforming growth factor beta I inhibits expression of the gene products for steel factor and its receptor (c-kit). *Blood* 85, 1769-80 (1995).

109. Sansilvestri, P., Cardoso, A. A., Batard, P., Panteme, B., Hatzfeld, A., Lim, B., Levesque, J. P., Monier, M. N. & Hatzfeld, J. Early CD34high cells can be separated into KIThigh cells in which transforming growth factor-beta (TGF-beta) dowrnmodulates c-kit and KITlow cells in which anti-TGF-beta upmodulates c-kit. *Blood* 86, 1729-35 (1995).

110. Fortunel, N., Batard, P., Hatzfeld, A., Monier, M. N., Panteme, B., Lebkowski, J. & Hatzfeld, J. High proliferative potential-quiescent cells: a working model to study primitive quiescent hematopoietic cells. *J Cell Sci* 111, 1867-75 (1998).

111. Broxmeyer, H. E., Sherry, B., Lu, L., Cooper, S., Oh, K. O., Tekamp-Olson, P., Kwon, B. S. & Cerami, A. Enhancing and suppressing effects of recombinant murine macrophage inflammatory proteins on colony formation in vitro by bone marrow myeloid progenitor cells. *Blood* 76, 1110-6 (1990).

112. Broxmeyer, H. E. & Kim, C. H. Regulation of hematopoiesis in a sea of chemokine family members with a plethora of redundant activities. *Exp Hematol* 27, 1113-23 (1999).

113. Lu, L., Xiao, M., Grigsby, S., Wang, W. X., Wu, B., Shen, R. N. & Broxmeyer, H. E. Comparative effects of suppressive cytokines on isolated single CD34(3+) stem/progenitor cells from human bone marrow and umbilical cord blood plated with and without serum. *Exp Hematol* 21, 1442-6 (1993).

114. Cooper, S., Mantel, C. & Broxmeyer, H. E. Myelosuppressive effects in vivo with very low dosages of monomeric recombinant murine macrophage inflammatory protein-1alpha. *Exp Hematol* 22, 186-93 (1994).

115. Lord, B. I., Dexter, T. M., Clements, J. M., Hunter, M. A. & Gearing, A. J. Macrophage-inflammatory protein protects multipotent hematopoietic cells from the cytotoxic effects of hydroxyurea in vivo. *Blood* 79, 2605-9 (1992).

116. Mayani, H., Little, M. T., Dragowska, W., Thornbury, G. & Lansdorp, P. M. Differential effects of the hematopoietic inhibitors MIP-1 alpha, TGF-beta, and TNF-alpha on cytokine-induced proliferation of subpopulations of CD34+ cells purified from cord blood and fetal liver. *Exp Hematol* 23, 422-7 (1995).

117. Zandstra, P. W., Eaves, C. J., and Piret, J. M. in *Ex Vivo Cell Therapy* (ed. Schindhelm, K. a. N., R) 245-272 (Academic Press, San Diego, 1999).

118. Zandstra, P. W., Conneally, E., Petzer, A. L., Piret, J. M. & Eaves, C. J. Cytokine manipulation of primitive human hematopoietic cell self-renewal. *Proc Natl Acad Sci USA* 94, 4698-703 (1997).

119. Piacibello, W., Gammaitoni, L., Bruno, S., Gunetti, M., Fagioli, F., Cavalloni, G. & Aglietta, M. Negative influence of il3 on the expansion of human cord blood in vivo long-term repopulating stem cells. *J Hematother Stem Cell Res* 9, 945-56. (2000).

120. Jo, D. Y., Rafii, S., Hamada, T. & Moore, M. A. Chemotaxis of primitive hematopoietic cells in response to stromal cell-derived factor-1. *J Clin Invest* 105, 101-11 (2000).

121. Rusten, L. S., Smeland, E. B., Jacobsen, F. W., Lien, E., Lesslauer, W., Loetscher, H., Dubois, C. M. & Jacobsen, S. E. Tumor necrosis factor-alpha inhibits stem cell factor-induced proliferation of human bone marrow progenitor cells in vitro. Role of p55 and p75 tumor necrosis factor receptors. *J Clin Invest* 94, 165-72. (1994).

122. Jacobsen, S. E., Veiby, O. P., Myldebust, J., Okkenhaug, C. & Lyman, S. D. Ability of flt3 ligand to stimulate the in vitro growth of primitive murine hematopoietic progenitors is potently and directly inhibited by transforming growth factor-beta and tumor necrosis factor-alpha. *Blood* 87, 5016-26 (1996).

123. Jacobsen, F. W., Veiby, O. P., Stokke, T. & Jacobsen, S. E. TNF-alpha bidirectionally modulates the viability of primitive murine hematopoietic progenitor cells in vitro. *J Immunol* 157, 1193-9. (1996).

124. Nagata, S. & Golstein, P. The Fas death factor. *Science* 267, 1449-56. (1995).

125. Glimm, H., Tang, P., Clark-Lewis, I., von Kalle, C. & Eaves, C. Ex vivo treatment of proliferating human cord blood stem cells with stroma-derived factor-1 enhances their ability to engraft NOD/SCID mice. *Blood* 99, 3454-7 (2002).

126. Peled, A., Petit, I., Kollet, O., Magid, M., Ponomaryov, T., Byk, T., Nagler, A., Ben-Hur, H., Many, A., Shultz, L., Lider, O., Alon, R., Zipori, D. & Lapidot, T. Dependence of human stem cell engraftment and repopulation of NOD/SCID mice on CXCR4. *Science* 283, 845-8 (1999).

127. Rocha, V., Cornish, J., Sievers, E. L., Filipovich, A., Locatelli, F., Peters, C., Remberger, M., Michel G., Arcese, W., Dallorso, S., Tiedemann, K., Busca, A., Chan, K. W., Kato, S., Ortega, J., Vowels, M., Zander, A., Souillet, G., Oakill, A., Woolfrey, A., Pay, A. L., Green, A., Garnier, F., Ionescu, I., Wemet, P., Sirchia, G., Rubinstein, P., Chevret, S. & Gluckman, E. Comparison of outcomes of unrelated bone marrow and umbilical cord blood transplants in children with acute leukemia. *Blood* 97, 2962-71 (2001).

128. Wagner, J. E., Barker, J. N., DeFor, T. E., Baker, K. S., Blazar, B. R., Eide, C., Goldman, A., Kersey, J., Krivit, W., MacMillan, M. L., Orchard, P. J., Peters, C., Weisdorf, D. J., Ramsay, N. K. & Davies, S. M. Transplantation of unrelated donor umbilical cord blood in 102 patients with malignant and nonmalignant diseases: influence of CD34 cell dose and HLA disparity on treatment-related mortality and survival. *Blood* 100, 1611-8 (2002).

129. Rubinstein, P., Carrier, C., Scaradavou, A., Kurtzberg, J., Adamson, J., Migliaccio, A. R., Berkowitz, R. L., Cabbad, M., Dobrila, N. L., Taylor, P. E., Rosenfield, R. E. & Stevens, C. E. Outcomes among 562 recipients of placental-blood transplants from unrelated donors [see comments]. *N Engl J A Med* 339, 1565-77 (1998).

130. Rogers, I., Sutherland, Holt, D., Macpate, F., Lains, A., Hollowell, S., Cruickshank, B. & Casper, R. F. Human UC-blood banking: impact of blood volume, cell separation and cryopreservation on leukocyte and CD34(+) cell recovery. *Cytotherapy* 3, 269-76 (2001).

131. Mazurier, F., Doedens, M., Gan, I. I. & Dick, J. E. Rapid myeloerythroid repopulation after intrafemoral transplantation of NOD-SCID mice reveals a new class of human stem cells. *Nat Med* 9, 959-63 (2003).

132. Murphy, L. D., Herzog, C. E., Rudick, J. B., Fojo, A. T. & Bates, S. E. Use of the polymerase chain reaction in the quantitation of mdr-1 gene expression. *Biochemistry* 29, 10351-6 (1990).

133. Taswell, C. Limiting dilution assays for the determination of immunocompetent cell frequencies. I. Data analysis. *J Immunol* 126, 1614-9 (1981).

134. Gluckman, E., Rocha, V., Boyer-Chammard, A., Locatelli, F., Arcese, W., Pasquini R., Ortega, J., Souillet, G., Ferreira, E., Laporte, J. P., Fernandez, M. & Chastang, C. Outcome of cord-blood transplantation from related and unrelated donors. Eurocord Transplant Group and the European Blood and Marrow Transplantation Group. *N Engl J Med* 337, 373-81 (1997).

135. Wagner, J. E., Rosenthal, J., Sweetman, R., Shu, X. O., Davies, S. M., Ramsay, N. K., McGlave, P. B., Sender, L. & Cairo, M. S. Successful transplantation of HLA-matched and HLA-mismatched umbilical cord blood from unrelated donors: analysis of engraftment and acute graft-versus-host disease. *Blood* 88, 795-802 (1996).

136. Wagner, J. E., Kernan, N. A., Steinbuch, M., Broxmeyer, H. E. & Gluckman, E. Allogeneic sibling umbilical-cord-blood transplantation in children with malignant and nonmalignant disease. *Lancet* 346, 214-9 (1995).

137. Barker, J. N. & Wagner, J. E. Umbilical-cord blood transplantation for the treatment of cancer. *Nat Rev Cancer* 3, 526-32 (2003).

138. Broxmeyer, H. E., Srour, E. F., Hangoc, G., Cooper, S., Anderson, S. A. & Bodine, D. M. High-efficiency recovery of functional hematopoietic progenitor and stem cells from human cord blood cryopreserved for 15 years. *Proc Natl Acad Sci USA* 100, 645-50 (2003).

139. Broxmeyer, H. E., Hangoc, G., Cooper, S., Ribeiro, R. C., Graves, V., Yoder, M., Wagner, J., Vadhan-Raj, S., Benninger, L., Rubinstein, P. & et al. Growth characteristics and expansion of human umbilical cord blood and estimation of its potential for transplantation in adults. *Proc Natl Acad Sci USA* 89, 4109-13 (1992).

140. Wagner, J. E., Broxmeyer, H. E., Byrd, R. L., Zehnbauer, B., Schmeckpeper, B., Shah, N., Griffin, C., Emanuel, P. D., Zuckerman, K. S., Cooper, S. & et al. Transplantation of umbilical cord blood after myeloablative therapy: analysis of engraftment [see comments]. *Blood* 79, 1874-81 (1992).

141. Zimmerman, T. M., Williams, S. F., Bender, J. G., Lee, W. J., Blake, M., Carreon, J., Swinney, P., Smith, S. J., Schilling, M., Oldham, F. & et al. Clinical use of selected and expanded peripheral blood CD34+cells: a preliminary report of feasibility and safety. *J Hematother* 4, 527-9 (1995).

142. Bachier, C. R., Gokmen, E., Teale, J., Lanzkron, S., Childs, C., Franklin, W., Shpall, E., Douville, I., Weber, S., Muller, T., Armstrong, D. & LeMaistre, C. F. Ex-vivo expansion of bone marrow progenitor cells for heinatopoietic reconstitution following high-dose chemotherapy for breast cancer. *Exp Hematol* 27, 615-23 (1999).

143. McNiece, I., Jones, R., Bearman, S. I., Cagnoni, P., Nieto, Y., Franklin, W., Ryder, J., Steele, A., Stoltz, J., Russell, P., McDermitt, J., Hogan, C., Murphy, J. & Shpall, E. J. Ex vivo expanded peripheral blood progenitor cells provide rapid neutrophil recovery after high-dose chemotherapy in patients with breast cancer. *Blood* 96, 3001-7 (2000).

144. Paqueffe, R. L., Dergham, S. T., Karpf, E., Wang, H. J., Slamon, D. J., Souza, L. & Glaspy, J. A. Ex vivo expanded unselected peripheral blood: progenitor cells reduce post-transplantation neutropenia, thrombocytopenia, and anemia in patients with breast cancer. *Blood* 96, 2385-90 (2000).

145. Reiffers, J., Cailliot, C., Dazey, B., Attal, M., Caraux, J. & Boiron, J. M. Abrogation of post-myeloablative chemotherapy neutropenia by ex-vivo expanded autologous CD34-positive cells. *Lancet* 354, 1092-3 (1999).

146. Stiff, P., Chen, B., Franklin, W., Oldenberg, D., Hsi, E., Bayer, R., Shpall, E., Douville, J., Mandalam, R., Malhotra, D., Muller, T., Armstrong, R. D. & Smith, A. Autologous transplantation of ex vivo expanded bone marrow cells grown from small aliquots after high-dose chemotherapy for breast cancer. *Blood* 95, 2169-74 (2000).

147. Devine, S. M., Lazarus, H. M. & Emerson, S. G. Clinical application of hematopoietic progenitor cell expansion: current status and future prospects. *Bone Marrow Transplant* 31, 241-52 (2003).

148. Purdy, M. H., Hogan, C. J., Hami, L., McNiece, I., Franklin, W., Jones, R. B., Bearman, S. I., Berenson, R. J., Cagnoni, P. J., Heimfeld, S. & et al. Large volume ex vivo expansion of CD34-positive hematopoietic progenitor cells for transplantation. *J Hematother* 4, 515-25 (1995).

149. Collins, P. C., Miller, W. M. & Papoutsakis, E. T. Stirred culture of peripheral and cord blood hematopoietic cells offers advantages over traditional static systems for clinically relevant applications. *Biotechnol Bioeng* 59, 53443 (1998).

150. Zandstra, P. W., Eaves, C. J. & Piret, J. M. Expansion of hematopoietic progenitor cell populations in stirred suspension bioreactors of normal human bone marrow cells. *Biotechnology (NY)* 12, 909-14. (1994).

151. Koller, M. R., Bender, J. G., Miller, W. M. & Papoutsakis, E. T. Expansion of primitive human hematopoietic progenitors in a perfusion bioreactor system with IL-3, IL-6, and stem cell factor. *Biotechnology (NY)* 11, 358-63 (1993).

152. Heike, T. & Nakahata, T. Ex vivo expansion of hematopoietic stem cells by cytokines. *Biochim Biophys Acta* 1592, 313-21 (2002).

153. Bhatia, M., Bonnet, D., Kapp, U., Wang, J. C., Murdoch, B. & Dick, J. E. Quantitative analysis reveals expansion of human hematopoietic repopulating cells after short-term ex vivo culture. *J Exp Med* 186, 619-24 (1997).

154. Peters, S. O., Kittler, E. L., Ramshaw, H. S. & Quesenberry, P. J. Ex vivo expansion of murine marrow cells with interleukin-3 (IL-3), IL-6, IL-11, and stem cell factor leads to impaired engraftment in irradiated hosts. *Blood* 87, 30-7 (1996).

155. Bhardwaj, G., Murdoch, B., Wu, D., Baker, D. P., Williams, K. P., Chadwick, K., Ling, L. E., Karanu, F. N. & Bhatia, M. Sonic hedgehog induces the proliferation of primitive human hematopoietic cells via BMP regulation. *Nat Immunol* 2, 172-80 (2001).

156. Antonchuk, J., Sauvageau, G. & Humphries, R. K. HOXB4-induced expansion of adult hematopoietic stem cells ex vivo. *Cell* 109, 3945 (2002).

157. Reya, T., Duncan, A. W., Ailles, L., Domen, J.; Scherer, D. C., Willert, K., Hintz, L., Nusse, R. & Weissman, I. L. A role for Wnt signalling in self-renewal of haematopoietic stem cells. *Nature* 423, 409-14 (2003).

158. Wickenhauser, C., Hillienhof, A., Jungheim, K., Lorenzen, J., Ruskowski, H., Hansmann, M. L., Thiele, J. & Fischer, R. Detection and quantification of transforming growth factor beta (TGF-beta) and platelet-derived growth factor (PDGF) release by normal human megakaryocytes. *Leukemia* 9, 310-5 (1995).

159. Mazurier, F., Gan, O. I., McKenzie, J. L., Doedens, M. & Dick, J. E. Lentivector-mediated clonal tracking reveals intrinsic heterogeneity in the human hematopoietic stem cell compartment and culture-induced stem cell impairment. *Blood* 103, 545-552 (2004).

160. Wright, D. E., Wagers, A. J., Gulati, A. P., Johnson, F. L. & Weissman, I. L. Physiological migration of hematopoietic stem and progenitor cells. *Science* 294, 1933-6 (2001).

161. Lansdorp, P. M. & Dragowska, W. Maintenance of hematopoiesis in serum-free bone marrow cultures involves sequential recruitment of quiescent progenitors. *Exp Hematol* 21, 1321-7 (1993).

162. Schwartz, R. M., Palsson, B. O. & Emerson, S. G. Rapid medium perfusion rate significantly increases the productivity and longevity of human bone marrow cultures. *Proc Natl Acad Sci USA* 88, 6760-4 (1991).

163. Caldwell, J., Palsson, B. O., Locey, B. & Emerson, S. G. Culture perfision schedules influence the metabolic activity and granulocyte-macrophage colony-stimulating factor production rates of human bone marrow stromal cells. *J Cell Physiol* 147, 344-53 (1991).

164. Koller, M. A., Palsson, M. A., Manchel, I. & Palsson, B. O. Long-term culture-initiating cell expansion is dependent on frequent medium exchange combined with stromal and other accessory cell effects. *Blood* 86, 1784-93 (1995).

We claim:

1. A bioprocess device comprising:
   a) a first cell culture chamber adapted to proliferate undifferentiated cells in culture media for a period of time;
   b) a second cell culture chamber adapted to permit the exchange of the culture media or obtain additional culture media to culture and proliferate the undifferentiated cells; and
   c) a conduit in regulatable fluid communication with the first chamber and the second chamber, wherein the conduit comprises a selection element that is adapted to bind differentiated cells;
   wherein the interior surfaces of the first cell culture chamber, the second cell culture chamber and the conduit are substantially closed to the environment.

2. The device of claim 1, wherein at least one of the first cell culture chamber or the second cell culture chamber is semipermeable to oxygen gas and carbon dioxide gas, but substantially impermeable to liquids.

3. The device of claim 1, wherein at least one of the first cell culture chamber or the second cell culture chamber is adapted to a pump device.

4. The device of claim 3, wherein the selection element has affinity for one or more antigens expressed by differentiated hematopoietic cells.

5. The device of claim 4, wherein the selection element has affinity for one or more antigens selected from the group consisting of: lin+antigens, CD2, CD3, CD4, CD8, CD13, CD14, CD16, CD19, CD24, CD38, CD45, CD56, CD66$b$ and glycophorin A.

6. The device of claim 1, wherein the device is modular, and the first chamber, the second chamber, or the conduit are detachable.

7. The device of claim 1, wherein the conduit further comprises at least one magnet.

8. The device of claim 1, wherein the conduit further comprises a magnetizable element.

9. A method of cell culture of undifferentiated cells comprising:
   a) culturing a sample of hematopoietic cells comprising a subset of undifferentiated hematopoietic cells in culture media contained in a first cell culture chamber under closed conditions appropriate to cause proliferation of the undifferentiated hematopoietic cells;
   b) segregating under closed conditions the undifferentiated hematopoietic cells from differentiated hematopoietic cells in a conduit in regulatable fluid communication with the first cell culture chamber and a second cell culture chamber, wherein the conduit comprises a selection element that is adapted to bind differentiated cells; and
   c) exchanging the culture media or providing additional culture media to the segregated undifferentiated hematopoietic cells in the second cell culture chamber under closed conditions, thereby segregating growth factors from the undifferentiated hematopoietic cells and causing proliferation of the segregated undifferentiated hematopoietic cells.

10. The method of claim 9, wherein the differentiated hematopoietic cells are segregated from the undifferentiated hematopoietic cells by affinity separation in the conduit.

11. The method of claim 10, wherein the differentiated hematopoietic cells are segregated from the undifferentiated hematopoietic cells by immunoaffinity separation in the conduit.

12. The method of claim 11, wherein immunoaffinity separation is performed using the selection element in the conduit, wherein the selection element comprises an antibody or fragment thereof with affinity for at least one antigen selected from the group consisting of: CD2, CD3, CD4, CD8, CD 13, CD 14, CD 16, CD 19, CD24, CD38, CD45, CD56, CD66b, and glycophorin A.

13. A method of expanding and preserving undifferentiated cells comprising:
   a) culturing a sample of hematopoietic cells comprising a subset of undifferentiated hematopoietic cells in culture media contained in a first cell culture chamber under closed conditions appropriate to cause proliferation of the undifferentiated hematopoietic cells;
   b) segregating the undifferentiated hematopoietic cells from differentiated hematopoietic cells under closed conditions in a conduit in regulatable fluid communication with the first cell culture chamber and a second cell culture chamber, wherein the conduit comprises a selection element that is adapted to bind differentiated cells; and
   c) exchanging the culture media or providing additional culture media to the segregated undifferentiated hematopoietic cells under closed conditions in the second cell culture chamber, thereby segregating growth factors from the undifferentiated hematopoietic cells and causing proliferation of the segregated undifferentiated hematopoietic cells; and
   d) freezing the segregated undifferentiated hematopoietic cells, thereby preserving the cells.

14. The method of claim 13, wherein the differentiated hematopoietic cells are segregated from the undifferentiated hematopoietic cells by affinity separation in the conduit.

15. The method of claim 13, wherein the differentiated hematopoietic cells are segregated from the undifferentiated hematopoietic cells by immunoaffinity separation in the conduit.

16. The method of claim 15, wherein the segregation is performed using the selection element in the conduit, wherein the selection element comprises an antibody or fragment thereof with affinity for at least one antigen selected from the group consisting of: CD2, CD3, CD4, CD8, CD 13, CD 14, CD 16, CD 19, CD24, CD38, CD45, CD56, CD66b, and glycophorin A.

* * * * *